United States Patent
Herz et al.

(10) Patent No.: US 7,514,460 B2
(45) Date of Patent: Apr. 7, 2009

(54) BENZAZOLE ANALOGUES AND USES THEREOF

(75) Inventors: Thomas Herz, Stockdorf (DE); Rolf Krauss, Planegg-Martinsried (DE); Michael Kubbutat, Schallstadt (DE); Martin Lang, Graefelfing (DE); Christoph Schaechtele, Freiburg (DE); Stefan Tasler, Seefeld-Hechendorf (DE); Frank Totzke, Freiburg (DE)

(73) Assignee: 4SC AG, Martinsried (DE)

( * ) Notice: Subject to any disclaimer, the term of this patent is extended or adjusted under 35 U.S.C. 154(b) by 206 days.

(21) Appl. No.: 11/303,854

(22) Filed: Dec. 15, 2005

(65) Prior Publication Data

US 2006/0135782 A1    Jun. 22, 2006

Related U.S. Application Data

(60) Provisional application No. 60/638,833, filed on Dec. 22, 2004.

(51) Int. Cl.
*A61K 31/428* (2006.01)
*A61K 31/517* (2006.01)
*A61K 31/496* (2006.01)
*C07D 417/02* (2006.01)
*C07D 403/02* (2006.01)
*C07D 403/14* (2006.01)
*C07D 401/02* (2006.01)
*C07D 401/14* (2006.01)

(52) U.S. Cl. ............ 514/367; 514/252.17; 514/266.22; 544/284; 544/359; 548/159; 548/161; 548/152

(58) Field of Classification Search .................. 514/367, 514/266.22, 252.17; 548/152, 159, 161; 544/284, 359

See application file for complete search history.

(56) References Cited

FOREIGN PATENT DOCUMENTS

| CA | 2319494 | 8/1999 |
|---|---|---|
| WO | WO 95/15758 A | 6/1995 |
| WO | WO 9924035 | 5/1999 |
| WO | WO 9940072 | 8/1999 |
| WO | WO 2000061580 | 10/2000 |
| WO | WO2004085425 | * 10/2004 |
| WO | WO 2004085425 | 10/2004 |

OTHER PUBLICATIONS

Morotti, et al. Oncogene, 2002, vol. 21, p. 4885-4893.*
Das, Jagabandhu et al. Discovery of 2-amino-heteroaryl-benzothiazole-6-anilides as potent p56lck inhibitors. Bioorganic & Medicincal Chemistry Letters, 2003, pp. 2587-2590, vol. 13, Elsevier Ltd.
Yin, Jingjun et al. Pd-catalyzed N-arylation of of heteroarylamines. Organic Letters, 2002, pp. 3481-3484, vol. 4, No. 20, American Chemical Society, USA.
Sedlak, Milos et al. Kinetics and mechanism of methanolysis and cyclization of 1-acyl-3-(2-halo-5-nitrophenyl)thioureas. Journal of Physical Organic Chemistry, 2001, pp. 187-195, vol. 14, John Wiley & Sons, Ltd., USA.
J. Adams et al., A Strategy for the Design of Multiplex Inhibitors for Kinase-Mediated Signalling in Angiogenesis. Crrent Opinion in Chemical Biology 6, 486-492, 2002.

* cited by examiner

*Primary Examiner*—Kamal A Saeed
*Assistant Examiner*—Yong Chu
(74) *Attorney, Agent, or Firm*—Baker Donelson, Bearman, Caldwell & Berkowitz; Susan E. Shaw McBee

(57) ABSTRACT

The present invention relates to $N^2$-heteroaryl-benzazole-2,(5 or 6)-diamine derivatives and compositions thereof as protein kinase inhibitors for the treatment of e.g. cancer.

17 Claims, No Drawings

BENZAZOLE ANALOGUES AND USES THEREOF

RELATED APPLICATIONS

This application claims benefit under 35 USC 119(e) to provisional application Ser. No. 60/638,833 filed on Dec. 22, 2004, which is incorporated herein by reference in its entirety

FIELD OF THE INVENTION

The present invention relates to benzazoles of the general formula (I) or a salt or a physiologically functional derivative or a stereoisomer thereof, for use as a medicament. The compounds of the invention are exceptionally useful for the treatment of diseases associated with abnormal and hyperproliferation of cells in a mammal, especially humans. In particular, they are useful for the treatment of all forms of cancer.

Furthermore a process of preparing said benzazole derivatives is disclosed.

BACKGROUND OF THE INVENTION

Protein kinases play a central role in the regulation of cellular functions. This includes processes like cell growth and division, cell differentiation and cell death, but also many other cellular activities. Protein kinases catalyze the transfer of phosphate residues from ATP on target proteins which as a consequence of this protein kinase mediated phosphorylation change their three-dimensional structure and thereby their physiological function. Depending on the amino acid which is phosphorylated by a protein kinase these enzymes are grouped in two families, the so-called serine/threonine protein kinases and the tyrosine protein kinases.

Based on the human genome project it is known that in human beings there exist 518 DNA sequences which encode for a protein kinase-like protein sequence. For several of these 518 proteins it could be shown in the last about 20 years that modifications in their related gene sequences (e.g. point mutations, deletions or gene amplifications) result in pathological changes of the cellular activities of the corresponding protein kinase. This is in particular true for protein kinases which are involved in cell proliferation and cell cycle control, in survival of cells and cell death, in tumor angiogenesis, and in formation of tumor metastases.

Several so-called oncogenes are pathologically modified genes which in their proto-oncogenic form encode for protein kinases involved in normal, physiological regulation of cell growth and division.

Since protein kinases are key regulators of cell functions and since they can show dysregulated enzymatic activity in cells they are promising targets for the development of therapeutic agents. There are many ongoing drug discovery projects in the pharmaceutical industry with the goal to identify modulators of protein kinases. The major focus is currently on protein kinases involved in inflammation and cancer, but besides this protein kinases are currently discussed as promising targets in almost every area of diseases.

In the field of tumors the first protein kinase inhibitors (Gleevec, Iressa) have already reached the market. In addition, a great number of protein kinase inhibitors are currently in various phases of clinical development. In most cases these compounds are either targeting subtypes of the EGF (Epidermal Growth Factor) receptor or of the VEGF (Vascular Endothelial Growth Factor) receptor. All these compounds have been developed with the goal to specifically inhibit one particular protein kinase, for which there is evidence that it interferes with one of the four major molecular processes of tumor progression. These four processes are (1) cell proliferation/cell cycle control, (2) regulation of programmed cell death (apoptosis) and cell survival, (3) tumor angiogenesis and (4) tumor metastasis.

The present invention relates to benzazole derivatives which may be useful for inhibition of protein kinases involved in diseases besides cancer, but which are especially useful as anti-tumor agents. This includes monospecific protein kinase inhibitors, which preferentially inhibit one protein kinase which is causatively involved in tumor progression, but also so-called multi-target protein kinase inhibitors, which inhibit at least two different protein kinases which play a role in two or more different molecular mechanism of tumor progression. As an example, such a compound could be an inhibitor of tumor angiogenesis and, in addition, also a stimulator of apoptosis.

The concept of multi-target protein kinase inhibitors is a new approach although the idea of developing "multiplex protein kinase inhibitors" has already been described by J. Adams et al., Current Opinion in Chemical Biology 6, 486-492, 2002. Therein compounds are described, which, at the same time, inhibit several protein kinases, which however all are involved in one molecular mechanism of tumor progression, namely tumor angiogenesis.

In WO 2004085425 benzazoles as kinase inhibitors are described.

In WO 9924035, 2-aminobenzothiazoles are described. These compounds have also been published in Das et al., Bioorg. Med. Chem. Lett 13, 2003, 2587-2590 and in Das et al., Bioorg. Med. Chem. Lett 13, 2003, 2145-2149.

In WO 2000061580, benzimidazolyl- and benzoxazolylacetylaminopyridylbutyrates are described as integrin antagonists.

In WO 9940072, five-membered, benzo-condensed heterocycles used as antithrombotics are described.

The object of the present invention is solved by the subject-matter of the independent claims. Further advantageous features, aspects and details of the invention are evident from the dependent claims, the description, the figures, and the examples of the present application.

Considering the lack of currently available treatment options for the majority of the conditions associated with protein kinases like ABL1, AKT1, AKT2, AKT3, Aurora-A, Aurora-B, Aurora-C, BRK, CDK1/CycB, CDK2/CycA, CDK2/CycE, CDK3/CycE, CDK4/CycD1, CDK5, CDK6/CycD1, CHK1, CK2, COT, CSK, DAPK1, EGF-R, EPHA1, EPHB1, EPHB2, EPHB3, EPHB4, ERBB2, ERBB4, FAK, FGF-R1, FGF-R3, FGF-R4, FGR, FLT3, GSK3-beta, IGF1-R, IKK-beta, INS-R, IRAK4, JAK2, JNK3, KIT, LCK, MET, MST4, MUSK, NEK2, NEK6, NLK, PAK1, PAK2, PAK4, PBK, PCTAIRE1, PDGFR-alpha, PDGFR-beta, PIM1, PKC-alpha, PKC-beta1, PKC-beta2, PKC-delta, PKC-epsilon, PKC-eta, PKC-gamma, PKC-iota, PKC-mu, PKC-theta, PKC-zeta, PLK1, PRK1, RET, S6K, SGK1, SGK3, SNK, SRC, SYK, TIE2, TSF1, TSK2, VEGF-R1, VEGF-R2, VEGF-R3, WEE1, especially with protein kinases like EGF-R (cell proliferation), ERBB2 (cell proliferation), PDGFR (cell proliferation), Aurora-A (cell cycle control), Aurora-B (cell cycle control), IGF1-R (apoptosis), VEGF-R2 (angiogenesis), VEGF-R3 (angiogenesis), Tie2 (angiogenesis), EPHB4 (angiogenesis), and SRC kinase (metastasis), there is still a great need for new therapeutic agents that inhibit these protein targets.

Benzazole derivatives described herein are a new group of protein kinase inhibitors which show differential inhibition of protein kinases, each of which can be assigned to one of the four molecular mechanisms of tumor development.

SUMMARY OF THE INVENTION

The present invention relates to compounds of the general formula (I) or a salt or a physiologically functional derivative or a stereoisomer thereof,

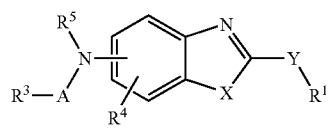

formula (I)

wherein the substituent

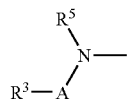

is attached to the 5- or 6-position of the benzazole;

X independently represents S, O, SO, or $SO_2$;

Y independently represents S, O, $NR^2$, SO, or $SO_2$;

A independently represents ←$CONR^8$—, ←$NR^8CO$—, ←$NR^8CONR^9$—; ←$NR^8COO$—, ←$NR^8NR^9CO$—, ←$NR^8OCO$—, ←$ONR^8CO$—, or ←$NR^8SO_2$—, where ← indicates the point of attachment to $R^3$;

$R^2$ independently represents H, alkyl, cycloalkyl, —$COR^6$, —$SOR^6$, —$SO_2R^6$, —CN, hydroxyalkyl, haloalkyl, haloalkyloxy, or alkylamino;

$R^3$ independently represents H, alkyl, cycloalkyl, aryl, or heteroaryl;

$R^4$ independently represents H, —$COR^6$, —$CO_2R^6$, —$SOR^6$, —$SO_2R^6$, —$SO_3R^6$, —$NO_2$, —CN, —$CF_3$, —$OCH_3$, —$OCF_3$, alkyl, cycloalkyl, alkoxy, —$NH_2$, alkylamino, —$NR^7COR^6$, halogen, —OH, —SH, alkylthio, haloalkyl, haloalkyloxy, aryl or heteroaryl;

$R^5$ independently represents H, alkyl, cycloalkyl, —$COR^6$, —$SOR^6$, —$SO_2R^6$, —CN, hydroxyalkyl, haloalkyl, haloalkyloxy, alkylamino, aryl, or heteroaryl;

$R^6$ independently represents H, alkyl, cycloalkyl, —$NR^8R^9$, —$NR^2NR^8R^9$, —$ONR^8R^9$, —$NR^8OR^9$, aryl or heteroaryl;

$R^7$ independently represents H, alkyl, cycloalkyl, or alkoxy;

$R^8$ independently represents H, alkyl, cycloalkyl, —$COR^6$, —$SOR^6$, —$SO_2R^6$, haloalkyl, haloalkyloxy, aryl or heteroaryl;

$R^9$ independently represents H, alkyl, cycloalkyl, —$COR^6$, —$SOR^6$, —$SO_2R^6$, hydroxyalkyl, haloalkyl, haloalkyloxy, aryl or heteroaryl;

$R^1$ independently represents one of the following groups:

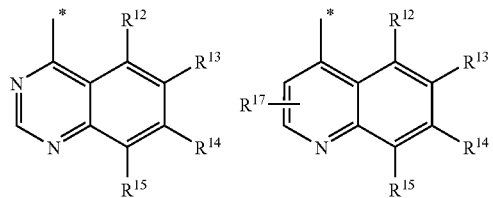

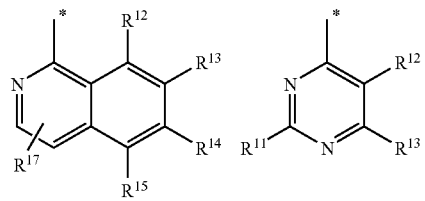

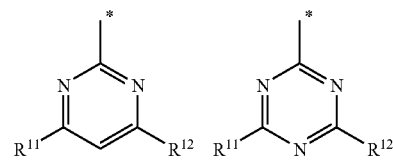

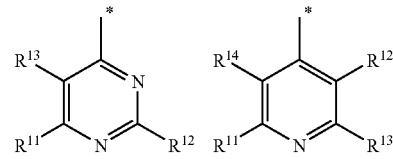

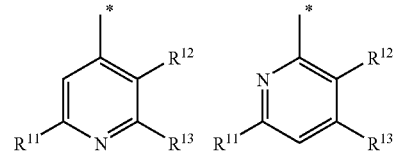

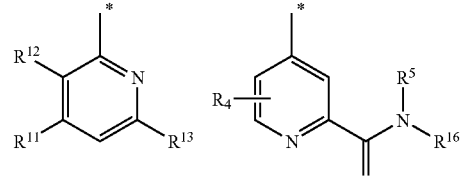

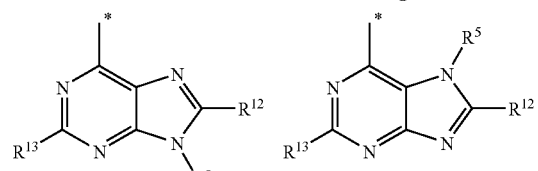

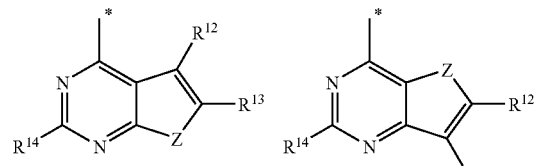

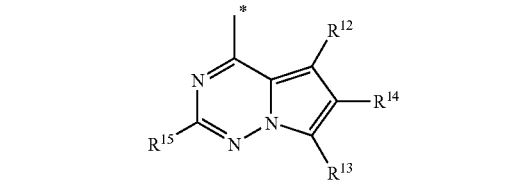

where * indicates the point of attachment

Z independently represents O, $NR^8$, or S;

$R^{11}$ independently represents H, —$NHR^8$, or one of the groups:

where * indicates the point of attachment.

$R^{12}$ independently represents H, halogen, nitro, trifluoromethyl, alkyl, aryl, heteroaryl, —$NR^8R^9$, or —$X^2R^{16}$;

$R^{13}$ independently represents H, halogen, nitro, trifluoromethyl, alkyl, aryl, heteroaryl, —$NR^8R^9$, or —$X^2R^{16}$;

$R^{14}$ independently represents H, halogen, nitro, trifluoromethyl, alkyl, aryl, heteroaryl, —$NR^8R^9$, or —$X^2R^{16}$;

$R^{15}$ independently represents H, halogen, nitro, trifluoromethyl, alkyl, aryl, heteroaryl, —$NR^8R^9$, or —$X^2R^{16}$;

$R^{17}$ independently represents H, halogen, nitro, trifluoromethyl, alkyl, aryl, heteroaryl, —$NR^8R^9$, or —$X^2R^{16}$;

$X^2$ independently represents a direct bond, —O—, —$CH_2$—, —OCO—, carbonyl, —S—, —SO—, —$SO_2$—, —$NR^8CO$—, —$CONR^8$—, —$SO_2NR^8$—, —$NR^8SO_2$— or —$NR^8$—;

$R^{16}$ independently represents H, alkyl, cycloalkyl, —$COR^6$, —$SOR^6$, —$SO_2R^6$, —$OCH_3$, —$OCF_3$, haloalkyl, haloalkyloxy, or one of the following groups:

where * indicates the point of attachment m independently represents an integer from 1-3;

L is absent or represents a divalent linkage group selected from alkylen, cycloalkylen, heterocyclylen, arylen, or heteroarylen, wherein one or more of the (—$CH_2$—) groups may be replaced by an oxygen or a $NR^8$, and wherein one or more carbon atoms may be independently substituted by one or two substituents selected from halogen, hydroxy, alkoxy, haloalkyloxy, phoshonooxy, or phoshonooxyalkyl;

$X^3$ independently represents —COOH, —COOalkyl, —$CONR^8R^9$, —OH, —$NR^8R^9$, —SH, —$SO_3H$, —$SO_2NR^8R^9$, alkyloxy, haloalkyloxy, or alkylamino;

$R^{18}$ independently represents H, phosphonooxy, or phosphonooxyalkyl;

$R^{19}$ independently represents H, alkyl, cycloalkyl, alkylamino, or alkoxy;

an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkynyl group, which can be substituted by one or more substituents R';

the $C_1$-$C_6$-alkyl, $C_2$-$C_6$-alkenyl and $C_2$-$C_6$-alkynyl residue may be selected from the group comprising —$CH_3$, —$C_2H_5$, —$CH=CH_2$, —$C\equiv CH$, —$C_3H_7$, —$CH(CH_3)_2$, —$CH_2$—$CH=CH_2$, —$C(CH_3)=CH_2$, —$CH=CH$—$CH_3$, —$C\equiv C$—$CH_3$, —$CH_2$—$C\equiv CH$, —$C_4H_9$, —$CH_2$—$CH(CH_3)_2$, —$CH(CH_3)$—$C_2H_5$, —$C(CH_3)_3$, —$C_5H_{11}$, $C_6H_{13}$, —$C(R')_3$, —$C_2(R')_5$, —$CH_2$—$C(R')_3$, —$C_3(R')_7$, —$C_2H_4$—$C(R')_3$, —$C_2H_4$—$CH=CH_2$, —$CH=CH$—$C_2H_5$, —$CH=C(CH_3)_2$, —$CH_2$—$CH=CH$—$CH_3$, —$CH=CH$—$CH=CH_2$, —$C_2H_4$—$C\equiv CH$, —$C\equiv C$—$C_2H_5$, —$CH_2$—$C\equiv C$—$CH_3$, —$C\equiv C$—$CH=CH_2$, —$CH=CH$—$C\equiv CH$, —$C\equiv C$—$C\equiv CH$, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_3H_6$—$CH=CH_2$, —$CH=CH$—$C_3H_7$, —$C_2H_4$—$CH=CH$—$CH_3$, —$CH_2$—$CH=CH$—$C_2H_5$, —$CH_2$—$CH=CH$—$CH=CH_2$, —$CH=CH$—$CH=CH$—$CH_3$, —$CH=CH$—$CH_2$—$CH=CH_2$, —$C(CH_3)=CH$—$CH=CH_2$, —$CH=C(CH_3)$—$CH=CH_2$, —$CH_2$—$CH=C(CH_3)_2$, $C(CH_3)=C(CH_3)_2$, —$C_3H_6$—$C\equiv CH$, —$C\equiv C$—$C_3H_7$, —$C_2H_4$—$C\equiv C$—$CH_3$, —$CH_2$—$C\equiv C$—$C_2H_5$, —$CH_2$—$C\equiv C$—$CH=CH_2$, —$CH_2$—$CH=CH$—$C\equiv CH$, —$CH_2$—$C\equiv C$—$C\equiv CH$, —$C\equiv C$—$CH=CH$—$CH_3$, —$CH=CH$—$C\equiv C$—$CH_3$, —$C\equiv C$—$C\equiv C$—$CH_3$, —$C\equiv C$—$CH_2$—$CH=CH_2$, —$CH=CH$—$CH_2$—$C\equiv CH$, —$C\equiv C$—$CH_2$—$C\equiv CH$, —$C(CH_3)=CH$—$CH=CH_2$, —$CH=C(CH_3)$—$CH=CH_2$, —$CH=CH$—$C(CH_3)=CH_2$, —$C(CH_3)=CH$—$C\equiv CH$, —$CH=C(CH_3)$—$C\equiv CH$, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅;

R' independently represents H, —CO₂R", —CONHR", —CR"O, —SO₂NR", —NR"—CO-haloalkyl, —NO₂, —NR"—SO₂-haloalkyl, —NR"—SO₂-alkyl, —SO₂-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" independently represents H, haloalkyl, hydroxyalkyl, alkyl, cycloalkyl, aryl, heteroaryl or aminoalkyl;

an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

a cycloalkylene group denotes a divalent non-aromatic ring system containing three to eight carbon atoms, preferably four to eight carbon atoms, wherein one or more of the carbon atoms in the ring may be substituted by a group E, E being O, S, SO, SO₂, N, or NR", R" being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group having five to fifteen carbon atoms, which may be substituted by one or more substituents R', and may be fused to another aromatic ring, where R' is as defined above;

a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring can be substituted by a group E, E being O, S, SO, SO₂, N, or NR", R" being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C($R^{10}$)₃, —C$R^{10}$($R^{10'}$)₂, —C$R^{10}$($R^{10'}$)$R^{10''}$, —C₂($R^{10}$)₅, —CH₂—C($R^{10}$)₃, —CH₂—C$R^{10}$($R^{10'}$)₂, —CH₂—C$R^{10}$($R^{10'}$)$R^{10''}$, —C₃($R^{10}$)₇, or —C₂H₄—C($R^{10}$)₃, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)₃, —OC$R^{10}$($R^{10'}$)₂, —OC$R^{10}$($R^{10'}$)$R^{10''}$, —OC₂($R^{10}$)₅, —OCH₂—C($R^{10}$)₃, —OCH₂—C$R^{10}$($R^{10'}$)₂, —OCH₂—C$R^{10}$($R^{10'}$)$R^{10''}$, —OC₃($R^{10}$)₇ or —OC₂H₄—C($R^{10}$)₃, wherein $R^{10}$, $R^{10'}$, $R^{10''}$ represent F, Cl, Br or I, preferably F;

a hydroxyalkylamino group denotes an (HO-alkyl)₂-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine an aryl group denotes an aromatic group having five to fifteen carbon atoms, which can be substituted by one or more substituents R', where R' is as defined above; the aryl group is preferably a phenyl group, -o-$C_6H_4$—R', -m-$C_6H_4$—R', -p-$C_6H_4$—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group. This heterocyclic group can be substituted by one or more substituents R', wherein R' is as defined above;

a phosphonooxy group is —O—P(=O)(OH)₂ or a salt thereof;

a phosphonooxyalkyl group denotes an -alkyl-O—P(=O)(OH)₂ group or a salt thereof, alkyl being as defined above The present invention relates to compounds of the general formula (Ia) or a salt or a physiologically functional derivative or a stereoisomer thereof,

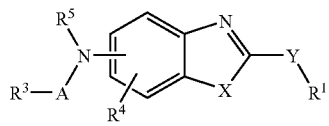

formula (Ia)

wherein the substituent

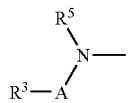

is attached to the 5- or 6-position of the benzazole;
X independently represents S, O, SO, or $SO_2$;
Y independently represents S, O, $NR^2$, SO, or $SO_2$;
A independently represents ←CO—, ←CS—, ←SO—, ←$SO_2$—, or ←$CO_2$—, where ← indicates the point of attachment to $R^3$;
$R^2$ independently represents H, alkyl, cycloalkyl, —$COR^6$, —$SOR^6$, —$SO_2R^6$, —CN, hydroxyalkyl, haloalkyl, haloalkyloxy, or alkylamino;
$R^3$ independently represents H, alkyl, cycloalkyl, aryl, or heteroaryl;
$R^4$ independently represents H, —$COR^6$, —$CO_2R^6$, —$SOR^6$, —$SO_2R^6$, —$SO_3R^6$, —$NO_2$, —CN, —$CF_3$, —$OCH_3$, —$OCF_3$, alkyl, cycloalkyl, alkoxy, —$NH_2$, alkylamino, —$NR^7COR^6$, halogen, —OH, —SH, alkylthio, haloalkyl, haloalkyloxy, aryl or heteroaryl;
$R^5$ independently represents H, alkyl, cycloalkyl, —$COR^6$, —$SOR^6$, —$SO_2R^6$, —CN, hydroxyalkyl, haloalkyl, haloalkyloxy, alkylamino, aryl, or heteroaryl;
$R^6$ independently represents H, alkyl, cycloalkyl, —$NR^8R^9$, —$NR^2NR^8R^9$, —$ONR^8R^9$, —$NR^8OR^9$, aryl or heteroaryl;
$R^7$ independently represents H, alkyl, cycloalkyl, or alkoxy;
$R^8$ independently represents H, alkyl, cycloalkyl, —$COR^6$, —$SOR^6$, —$SO_2R^6$, haloalkyl, haloalkyloxy, aryl or heteroaryl;
$R^9$ independently represents H, alkyl, cycloalkyl, —$COR^6$, —$SOR^6$, —$SO_2R^6$, hydroxyalkyl, haloalkyl, haloalkyloxy, aryl or heteroaryl;
$R^1$ independently represents one of the following groups:

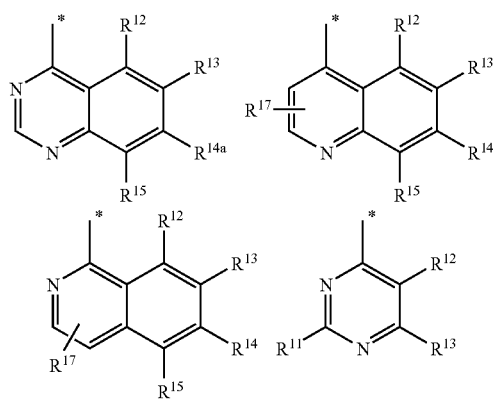

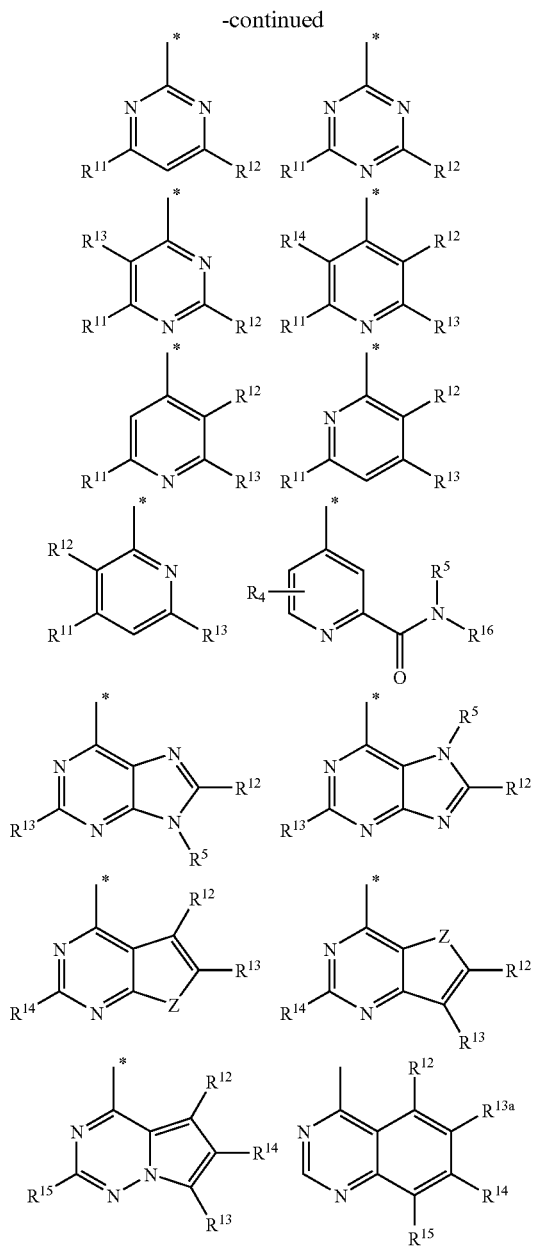

where * indicates the point of attachment
Z independently represents O, $NR^8$, or S;
$R^{11}$ independently represents H, —$NHR^8$, or one of the groups:

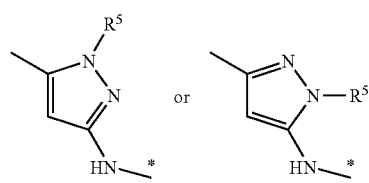

where * indicates the point of attachment.
$R^{12}$ independently represents H, halogen, nitro, trifluoromethyl, alkyl, aryl, heteroaryl, —$NR^8R^9$, or —$X^2R^{16}$;

$R^{13a}$ independently represents nitro, aryl, heteroaryl, —NR$^8$R$^9$, or —X$^2$R$^{16a}$;

$R^{14a}$ independently represents nitro, aryl, heteroaryl, —NR$^8$R$^9$, or —X$^2$R$^{16a}$;

$R^{14}$ independently represents H, halogen, nitro, trifluoromethyl, alkyl, aryl, heteroaryl, —NR$^8$R$^9$, or —X$^2$R$^{16}$;

$R^{13}$ independently represents H, halogen, nitro, trifluoromethyl, alkyl, aryl, heteroaryl, —NR$^8$R$^9$, or —X$^2$R$^{16}$;

$R^{15}$ independently represents H, halogen, nitro, trifluoromethyl, alkyl, aryl, heteroaryl, —NR$^8$R$^9$, or —X$^2$R$^{16}$;

$R^{17}$ independently represents H, halogen, nitro, trifluoromethyl, alkyl, aryl, heteroaryl, —NR$^8$R$^9$, or —X$^2$R$^{16}$;

$X^2$ independently represents a direct bond, —O—, —CH$_2$—, —OCO—, carbonyl, —S—, —SO—, —SO$_2$—, —NR$^8$CO—, —CONR$^8$—, —SO$_2$NR$^8$, —NR$^8$SO$_2$— or —NR$^8$—;

$R^{16}$ independently represents H, alkyl, cycloalkyl, —COR$^6$, —SOR$^6$, —SO$_2$R$^6$, —OCH$_3$, —OCF$_3$, haloalkyl, haloalkyloxy, or one of the following groups:

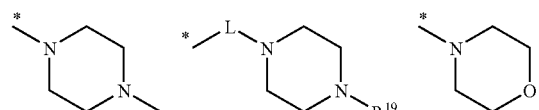
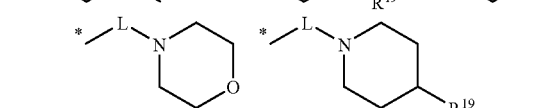
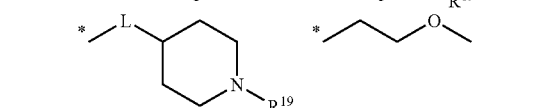
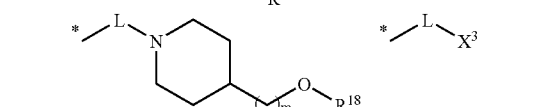
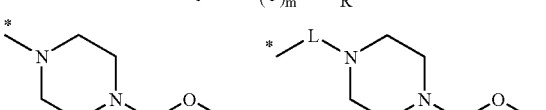
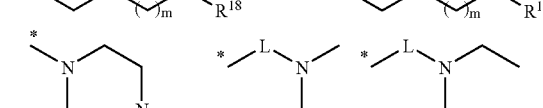
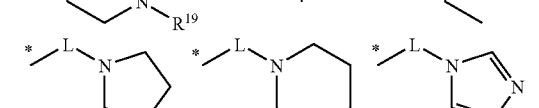
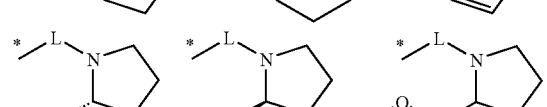
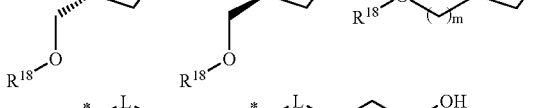
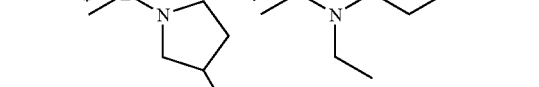
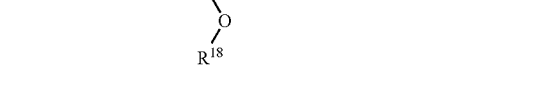

-continued

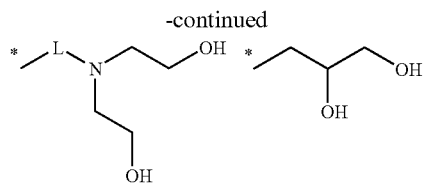

wherein * indicates the point of attachment m independently represents an integer from 1-3;

L is absent or represents a divalent linkage group selected from alkylen, cycloalkylen, heterocyclylen, arylen, or heteroarylen, wherein one or more of the (—CH$_2$—) groups may be replaced by an oxygen or a NR$^8$, and wherein one or more carbon atoms may be independently substituted by one or two substituents selected from halogen, hydroxy, alkoxy, haloalkyloxy, phoshonooxy, or phoshonooxyalkyl;

$X^3$ independently represents —COOH, —COOalkyl, —CONR$^8$R$^9$, —OH, —NR$^8$R$^9$, —SH, —SO$_3$H, —SO$_2$NR$^8$R$^9$, alkyloxy, haloalkyloxy, or alkylamino;

$R^{18}$ independently represents H, phosphonooxy, or phosphonooxyalkyl;

$R^{19}$ independently represents H, alkyl, cycloalkyl, alkylamino, or alkoxy;

$R^{16a}$ independently represents one of the following groups:

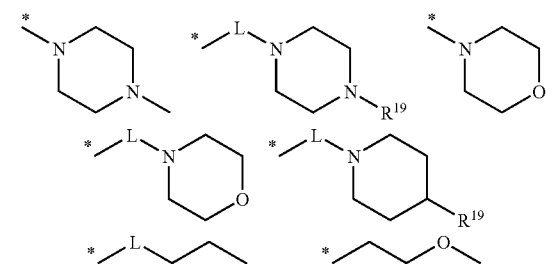
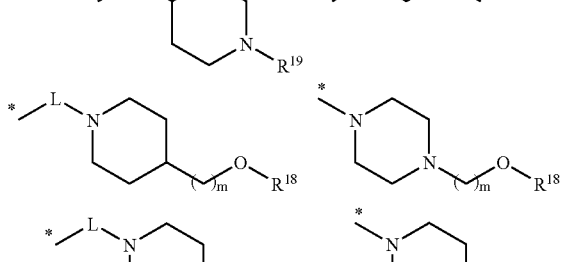
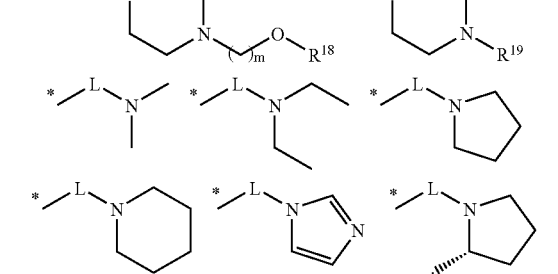

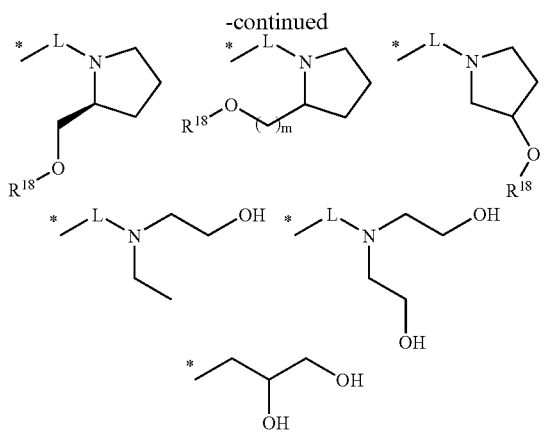

where * indicates the point of attachment an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkynyl group, which can be substituted by one or more substituents R';

the $C_1$-$C_6$-alkyl, $C_2$-$C_6$-alkenyl and $C_2$-$C_6$-alkynyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3$)$_2$, C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$CH_2$—CH=CH—CH=CH—$CH_3$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

R' independently represents H, —$CO_2$R", —CONHR", —CR"O, —$SO_2$NR", —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" independently represents H, haloalkyl, hydroxyalkyl, alkyl, cycloalkyl, aryl, heteroaryl or aminoalkyl;

an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

a cycloalkylene group denotes a divalent non-aromatic ring system containing three to eight carbon atoms, preferably four to eight carbon atoms, wherein one or more of the carbon atoms in the ring may be substituted by a group E, E being O, S, SO, $SO_2$, N, or NR", R" being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group having five to fifteen carbon atoms, which may be substituted by one or more substituents R', and may be fused to another aromatic ring, where R' is as defined above;

a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring can be substituted by a group E, E being O, S, SO, $SO_2$, N, or NR", R" being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C($R^{10}$)$_3$, —C$R^{10}$($R^{10'}$)$_2$, —C$R^{10}$($R^{10'}$)$R^{10''}$, —$C_2$($R^{10'}$)$_5$, —$CH_2$—C($R^{10}$)$_3$, —$CH_2$—C$R^{10}$($R^{10'}$)$_2$, —$CH_2$—C$R^{10}$($R^{10'}$)$R^{10''}$, —$C_3$($R^{10'}$)$_7$, or —$C_2H_4$—C($R^{10}$)$_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —OC$R^{10}$($R^{10'}$)$_2$, —OC$R^{10}$($R^{10'}$)$R^{10''}$, —O$C_2$($R^{10'}$)$_5$, —O$CH_2$—C($R^{10}$)$_3$, —O$CH_2$—C$R^{10}$($R^{10'}$)$_2$, —O$CH_2$—C$R^{10}$($R^{10'}$)$R^{10''}$, —O$C_3$($R^{10'}$)$_7$ or —O$C_2H_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R', where R' is as defined above; the aryl group is preferably a phenyl group, -o-$C_6H_4$—R', -m-$C_6H_4$—R', -p-$C_6H_4$—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group. This heterocyclic group can be substituted by one or more substituents R', wherein R' is as defined above;

a phosphonooxy group is —O—P(=O)(OH)$_2$ or a salt thereof;

a phosphonooxyalkyl group denotes an -alkyl-O—P(=O)(OH)$_2$ group or a salt thereof, alkyl being as defined above.

The present invention relates to compounds of the general formula (Ib) or a salt or a physiologically functional derivative or a stereoisomer thereof, formula (Ib)

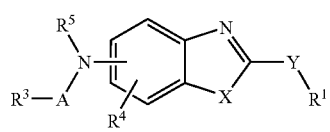

wherein the substituent

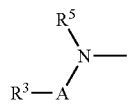

is attached to the 5- or 6-position of the benzazole;

X independently represents S, O, SO, or $SO_2$;

Y independently represents S, O, $NR^2$, SO, or $SO_2$; A independently represents ←CO—, ←CS—, ←SO—, ←$SO_2$—, or ←$CO_2$—, where ← indicates the point of attachment to $R^3$;

$R^2$ independently represents H, alkyl, cycloalkyl, —$COR^6$, —$SOR^6$, —$SO_2R^6$, —CN, hydroxyalkyl, haloalkyl, haloalkyloxy, or alkylamino;

$R^3$ independently represents aryl, or heteroaryl;

$R^4$ independently represents H, —$COR^6$, —$CO_2R^6$, —$SOR^6$, —$SO_2R^6$, —$SO_3R^6$, —$NO_2$, —CN, —$CF_3$, —$OCH_3$, —$OCF_3$, alkyl, cycloalkyl, alkoxy, —$NH_2$, alkylamino, —$NR^7COR^6$, halogen, —OH, —SH, alkylthio, haloalkyl, haloalkyloxy, aryl or heteroaryl;

$R^5$ independently represents H, alkyl, cycloalkyl, —$COR^6$, —$SOR^6$, —$SO_2R^6$, —CN, hydroxyalkyl, haloalkyl, haloalkyloxy, alkylamino, aryl, or heteroaryl;

$R^6$ independently represents H, alkyl, cycloalkyl, —$NR^8R^9$, —$NR^2NR^8R^9$, —$ONR^8R^9$, —$NR^8OR^9$, aryl or heteroaryl;

$R^7$ independently represents H, alkyl, cycloalkyl, or alkoxy;

$R^8$ independently represents H, alkyl, cycloalkyl, —$COR^6$, —$SOR^6$, —$SO_2R^6$, haloalkyl, haloalkyloxy, aryl or heteroaryl;

$R^9$ independently represents H, alkyl, cycloalkyl, —$COR^6$, —$SOR^6$, —$SO_2R^6$, hydroxyalkyl, haloalkyl, haloalkyloxy, aryl or heteroaryl;

$R^1$ independently represents one of the following groups:

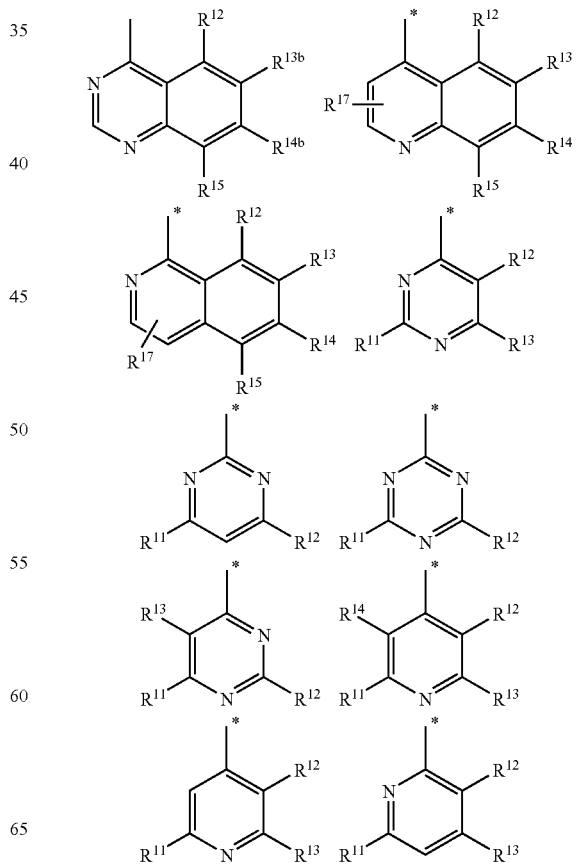

-continued

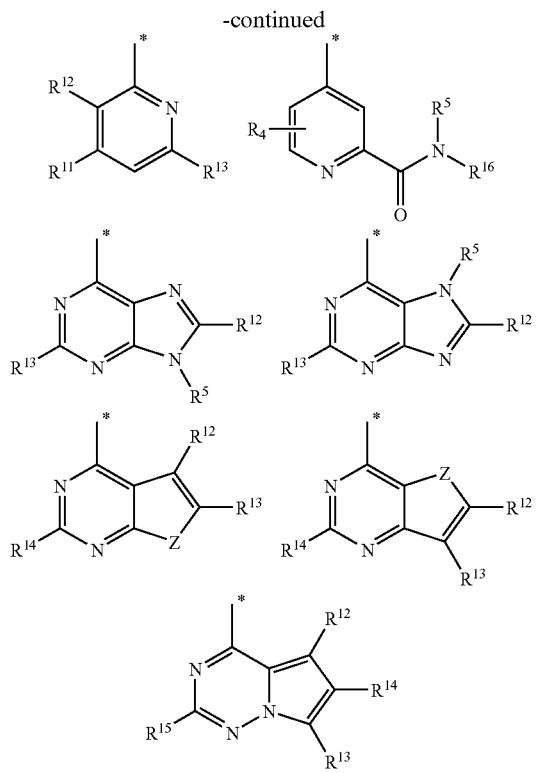

where * indicates the point of attachment

Z independently represents O, NR$^8$, or S;

R$^{11}$ independently represents H, —NHR$^8$, or one of the groups:

where * indicates the point of attachment.

R$^{12}$ independently represents H, halogen, nitro, trifluoromethyl, alkyl, aryl, heteroaryl, —NR$^8$R$^9$, or —X$^2$R$^{16}$;

R$^{13}$ independently represents H, halogen, nitro, trifluoromethyl, alkyl, aryl, heteroaryl, —NR$^8$R$^9$, or —X$^2$R$^{16}$;

R$^{13b}$ independently represents H, halogen, haloalkyloxy, alkyl, or alkoxy;

R$^{14}$ independently represents H, halogen, nitro, trifluoromethyl, alkyl, aryl, heteroaryl, —NR$^8$R$^9$, or —X$^2$R$^6$;

R$^{14b}$ independently represents H, halogen, haloalkyloxy, alkyl, or alkoxy;

R$^{15}$ independently represents H, halogen, nitro, trifluoromethyl, alkyl, aryl, heteroaryl, —NR$^8$R$^9$, or —X$^2$R$^6$;

R$^{17}$ independently represents H, halogen, nitro, trifluoromethyl, alkyl, aryl, heteroaryl, —NR$^8$R$^9$, or —X$^2$R$^6$;

X$^2$ independently represents a direct bond, —O—, —CH$_2$—, —OCO—, carbonyl, —S—, —SO—, —SO$_2$—, —NR$^8$CO—, —CONR$^8$—, —SO$_2$NR$^8$—, —NR$^8$SO$_2$— or —NR$^8$—;

R$^{16}$ independently represents H, alkyl, cycloalkyl, —COR$^6$, —SOR$^6$, —SO$_2$R$^6$, —OCH$_3$, —OCF$_3$, haloalkyl, haloalkyloxy, or one of the following groups:

where * indicates the point of attachment m independently represents an integer from 1-3;

L is absent or represents a divalent linkage group selected from alkylen, cycloalkylen, heterocyclylen, arylen, or heteroarylen, wherein one or more of the (—CH$_2$—) groups may be replaced by an oxygen or a NR$^8$, and wherein one or more carbon atoms may be independently substituted by one or two substituents selected from halogen, hydroxy, alkoxy, haloalkyloxy, phoshonooxy, or phoshonooxyalkyl;

X³ independently represents —COOH, —COOalkyl, —CONR⁸R⁹, —OH, —NR⁸R⁹, —SH, —SO₃H, —SO₂NR⁸R⁹, alkyloxy, haloalkyloxy, or alkylamino;

R¹⁸ independently represents H, phosphonooxy, or phosphonooxyalkyl;

R¹⁹ independently represents H, alkyl, cycloalkyl, alkylamino, or alkoxy;

an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkynyl group, which can be substituted by one or more substituents R';

the $C_1$-$C_6$-alkyl, $C_2$-$C_6$-alkenyl and $C_2$-$C_6$-alkynyl residue may be selected from the group comprising —CH₃, —C₂H₅, —CH=CH₂, —C≡CH, —C₃H₇, —CH(CH₃)₂, —CH₂—CH=CH₂, —C(CH₃)=CH₂, —CH=CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R')₃, —C₂(R')₅, —CH₂—C(R')₃, —C₃(R')₇, —C₂H₄—C(R')₃, —C₂H₄—CH=CH₂, —CH=CH—C₂H₅, —CH=C(CH₃)₂, —CH₂—CH=CH—CH₃, —CH=CH—CH=CH₂, —C₂H₄—C≡CH, —C≡C—C₂H₅, —CH₂—C≡C—CH₃, —C≡C—CH=CH₂, —CH=CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH=CH₂, —CH=CH—C₃H₇, —C₂H₄—CH=CH—CH₃, —CH₂—CH=CH—C₂H₅, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH=CH—CH=C(CH₃)=CH₂, —CH₂—CH=C(CH₃)₂, C(CH₃)=C(CH₃)₂, —C₃H₆—C≡CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂—C≡C—C≡CH, —C≡C—CH=CH—CH₃, —CH=CH—C≡C—CH₃, —C≡C—C≡C—CH₃, —C≡C—CH₂—CH=CH₂, —CH=CH—CH₂—C≡CH, —C≡C—CH₂—C≡CH, —C(CH₃)=CH—CH=CH₂, —CH=C(CH₃)—CH=CH₂, —CH=CH—C(CH₃)=CH₂, —C(CH₃)=CH—C≡CH, —CH=C(CH₃)—C≡CH, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, —C₂H₄—C≡C—C₂H₅;

R' independently represents H, —CO₂R'', —CONHR'', —CR''O, —SO₂NR'', —NR''—CO-haloalkyl, —NO₂, —NR''—SO₂-haloalkyl, —NR''—SO₂-alkyl, —SO₂-alkyl, —NR''—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R'' independently represents H, haloalkyl, hydroxyalkyl, alkyl, cycloalkyl, aryl, heteroaryl or aminoalkyl;

an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

a cycloalkylene group denotes a divalent non-aromatic ring system containing three to eight carbon atoms, preferably four to eight carbon atoms, wherein one or more of the carbon atoms in the ring may be substituted by a group E, E being O, S, SO, SO₂, N, or NR', R'' being as defined above;

a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

an arylene group denotes an aromatic divalent group having five to fifteen carbon atoms, which may be substituted by one or more substituents R', and may be fused to another aromatic ring, where R' is as defined above;

a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring can be substituted by a group E, E being O, S, SO, SO₂, N, or NR'', R'' being as defined above; the $C_3$-$C_8$-cycloalkyl residue may be selected from the group comprising -cyclo-C₃H₅, -cyclo-C₄H₇, -cyclo-C₅H₉, -cyclo-C₆H₁₁, -cyclo-C₇H₁₃, -cyclo-C₉H₁₅, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C(R¹⁰)₃, —CR¹⁰(R¹⁰')₂, —CR¹⁰(R¹⁰')R¹⁰'', —C₂(R¹⁰)₅, —CH₂—C(R¹⁰)₃, —CH₂—CR¹⁰(R¹⁰')₂, —CH₂—CR¹⁰(R¹⁰')R¹⁰'', —C₃(R¹⁰)₇, or —C₂H₄—C(R¹⁰)₃, wherein R¹⁰, R¹⁰', R¹⁰'' represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R¹⁰)₃, —OCR¹⁰(R¹⁰')₂, —OCR¹⁰(R¹⁰')R¹⁰'', —OC₂(R¹⁰)₅, —OCH₂—C(R¹⁰)₃, —OCH₂—CR¹⁰(R¹⁰')₂, —OCH₂—CR¹⁰(R¹⁰')R¹⁰'', —OC₃(R¹⁰)₇ or —OC₂H₄—C(R¹⁰)₃, wherein R¹⁰, R¹⁰', R¹⁰'' represent F, Cl, Br or I, preferably F;

a hydroxyalkylamino group denotes an (HO-alkyl)₂-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R', where R' is as defined above; the aryl group is preferably a phenyl group, -o-C₆H₄—R', -m-C₆H₄—R', -p-C₆H₄—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, 1,2,5-oxadiazol-4-yl, 1,2,4-thiadiazol-3-yl, 1,2,4-thiadiazol-5-yl, isothiazol-3-yl, isothiazol-4-yl, isothiazol-5-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, triazolopyridazine group. This heterocyclic group can be substituted by one or more substituents R', wherein R' is as defined above;

a phosphonooxy group is —O—P(=O)(OH)$_2$ or a salt thereof;

a phosphonooxyalkyl group denotes an -alkyl-O—P(=O)(OH)$_2$ group or a salt thereof, alkyl being as defined above.

The invention also provides a pharmaceutical composition comprising a compound of formula (I), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

Prodrugs of the compounds of the present invention include but are not limited to: esters, which are transformed in vivo into the corresponding active alcohol, esters, which are transformed in vivo into the corresponding active acid, imines, which are transformed in vivo into the corresponding amines, imines which are metabolized in vivo into the corresponding active carbonyl derivative (e.g. aldehyde or ketone), 1-carboxy-amines, which are decarboxylated in vivo into the active amine, phosphoryloxy-compounds, which are dephosporylated in vivo by phosphateases into the active alcohols, and amides which are metabolized into the corresponding active amine or acid respectively.

The term "stereoisomer" as used herein refers to compound with at least one stereogenic center, which can be R- or S-configurated. It has to be understood, that in compounds with more than one stereogenic center each of which independently from each other can be R- or S-configurated. The term "stereoisomer" as used herein also refers to salts of the compounds herein described with optically active acids or bases.

In addition, the present invention provides methods for preparing the compounds of the invention.

DETAILED DESCRIPTION OF THE PREFERRED EMBODIMENTS

The compounds of the present invention may be obtained via various methods. One possibility for the synthesis of compounds of the present invention comprises the step of reacting a compound of formula (VII), wherein $R^3$, $R^4$, $R^5$, A, X, and Y are as defined above, with a compound of formula (VIII), wherein R' is as defined above and LG comprises a leaving group such as Cl, Br, and I. Either nucleophilic substitution or palladium-catalyzed cross-coupling may be applied. Palladium-catalyzed heteroarylation of 2-aminobenzothiazoles is for example described in J. Yin, M. M. Zhao, M. A. Huffman, J. M. McNamara, *Org. Lett.* 2002, 4, 3481-3484. If Y=NR$^2$, R$^2$ may be added before or after addition of R$^1$.

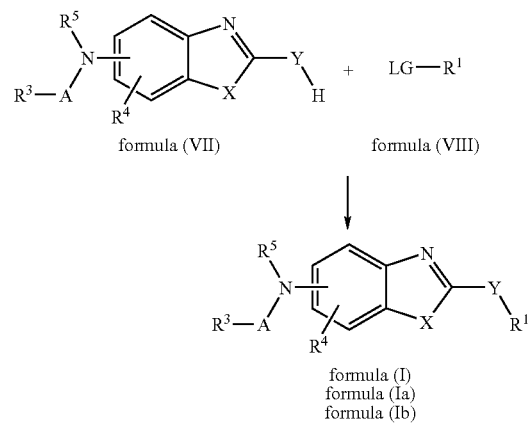

Another way to synthesize compounds of the present invention comprises the step of adding a R$^5$ to a compound of formula (IX), wherein R$^1$, R$^4$, R$^8$, X, and Y are as defined above, followed by reaction with an acid chloride, a carboxylic acid, a sulfonic acid chloride, or an isocyanate or vice versa.

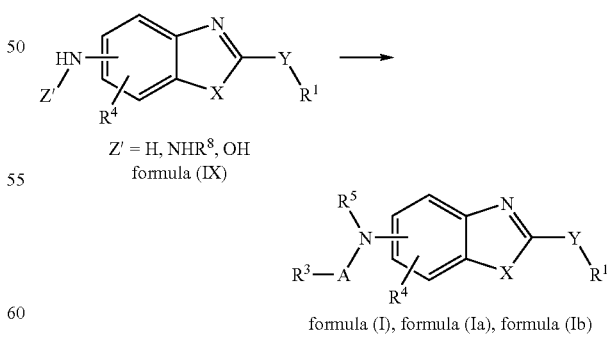

Compounds of the formula (VII) can be synthesized by addition of R$^5$ to a compound of formula (X), wherein R$^4$, R$^8$, X, and Y are as defined above, followed by reaction with an acid chloride, a carboxylic acid, a sulfonic acid chloride, or an isocyanate or vice versa, followed by contingent addition of $R^2$ if $Y=NR^2$. In some cases protection of Y will be necessary (e.g. Boc protection if $Y=NR^2$). This protection group has to be removed before compounds of formula (VII) are converted into compounds of formula (I).

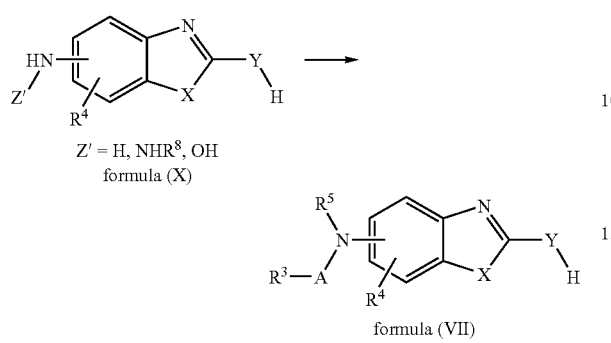

The compounds of formula (IX), wherein $Z'=H$, OH can be obtained by addition of compounds of formula (VIII), wherein R' is as defined above and LG comprises a leaving group such as Cl, Br, and I, to compounds of formula (XI), wherein $R^4$, X, and Y are as defined above, followed by addition of $R^2$ or vice versa and subsequent reduction of the nitro group. With respect to later stages in the synthesis, protection of Y might be necessary before reduction of the nitro group (e.g. Boc protection if $Y=NR^2$).

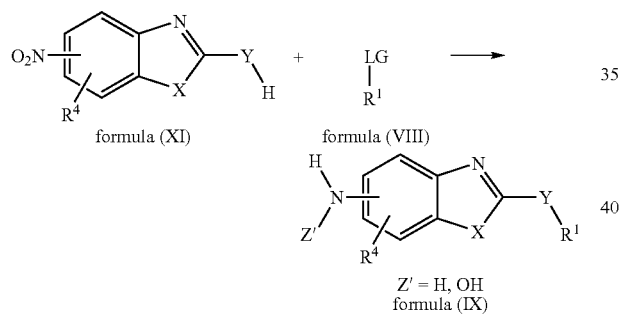

The compounds of formula (IX), wherein $Z'=NHR^8$ can be obtained by the reduction of adequate diazonium salts and subsequent addition of $R^8$.

The compounds of formula (X), wherein $Z'=H$, OH can be obtained by reduction of compounds of formula (XI), wherein $R^4$, X, and Y are as defined above.

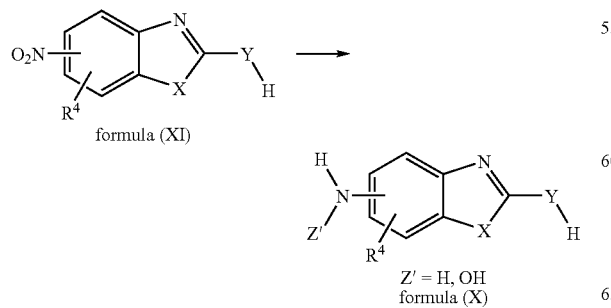

The compounds of formula (X), wherein $Z'=NHR^8$ can be obtained by reduction of compounds of formula (XII), wherein $R^4$, X, and Y are as defined above, and subsequent addition of $R^8$.

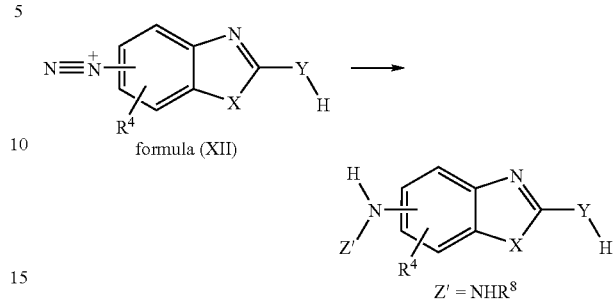

A preferred embodiment of the invention, are compounds of the formula (II)

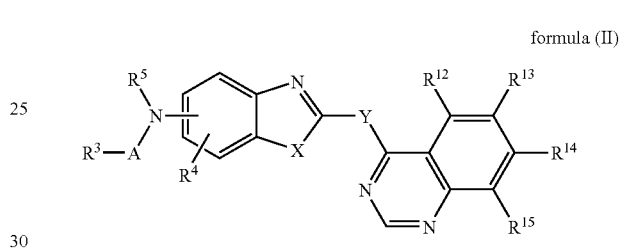

wherein.

the substituent

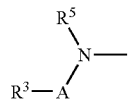

is attached to the 5- or 6-position of the benzazole;

A, X, Y, $R^3$, $R^4$, $R^5$, $R^{12}$, $R^{13}$, $R^{14}$, and $R^{15}$ are as defined above for formula (I).

A preferred embodiment of the invention, are compounds of the formula (II) wherein $R^3$ is an optionally substituted aryl group.

A more preferred embodiment of the invention, are compounds of the formula (II) wherein $R^3$ is an optionally substituted phenyl group.

Another preferred embodiment of the invention, are compounds of the formula (III)

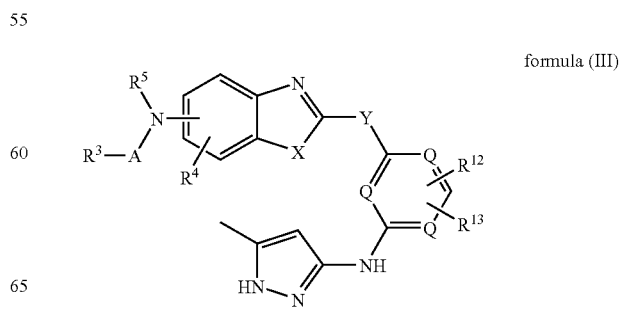

wherein
the substituent

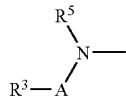

is attached to the 5- or 6-position of the benzazole;
Q independently represents C, N, CH and at least one Q is N;
A, X, Y, $R^3$, $R^4$, $R^5$, $R^{12}$, and $R^{13}$ are as defined above for formula (I);

A more preferred embodiment of the invention, are compounds of the formula (IIIa)

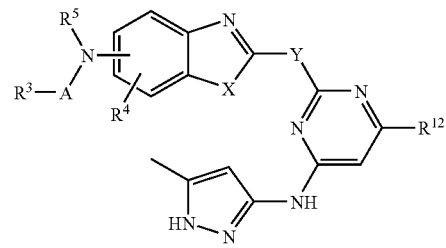

formula (IIIa)

wherein
the substituent

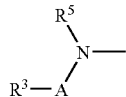

is attached to the 5- or 6-position of the benzazole;
A, X, Y, $R^3$, $R^4$, $R^5$, and $R^{12}$ are as defined above for formula (I).

Another preferred embodiment of the invention, are compounds of the formula (IV)

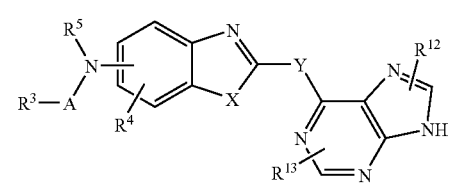

formula (IV)

wherein
the substituent

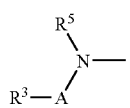

is attached to the 5- or 6-position of the benzazole;
A, X, Y, $R^3$, $R^4$, $R^5$, $R^{12}$, and $R^{13}$ are as defined above for formula (I);

Another preferred embodiment of the invention, are compounds of the formula (V)

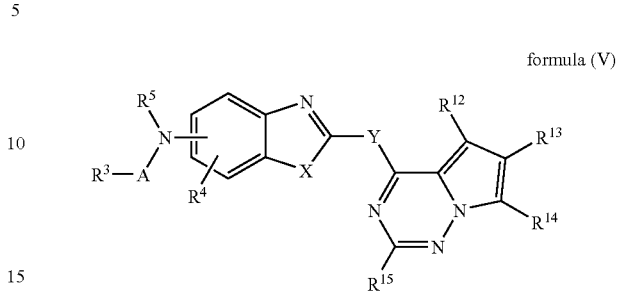

formula (V)

wherein
the substituent

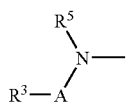

is attached to the 5- or 6-position of the benzazole;
A, X, Y, $R^3$, $R^4$, $R^5$, $R^{12}$, $R^{13}$, $R^{14}$, and $R^{15}$ are as defined above for fomula (I).

Another preferred embodiment of the invention, are compounds of the formula (VI)

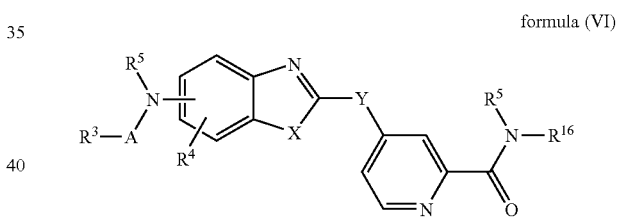

formula (VI)

wherein
the substituent

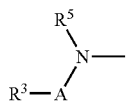

is attached to the 5- or 6-position of the benzazole;
A, X, Y, $R^3$, $R^4$, $R^5$, and $R^{16}$ are as defined above for formula (I).

Another preferred embodiment of the invention, are compounds of formula (I), where
X represents S; Y represents NH; A represents ←NHCO—, where ← indicates the point of attachment to $R^3$; $R^5$ represents H.

Another preferred embodiment of the invention, are compounds of formula (I), where
X represents S; Y represents NH; A represents ←NHCO—, where ← indicates the point of attachment to $R^3$; $R^3$ is an optionally substituted aryl group, $R^5$ represents H.

Another preferred embodiment of the invention, are compounds of formula (I), where X represents S; Y represents NH; A represents ←NHCO—, where ← indicates the point of attachment to $R^3$; $R^3$ is an optionally substituted phenyl group, $R^5$ represents H.

Another preferred embodiment of the invention, are compounds of formula (I), where the

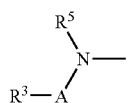

substituent is attached to the 5-position of the benzazole.

Another preferred embodiment of the invention, are compounds of formula (I), where the

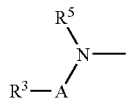

substituent is attached to the 6-position of the benzazole.

Another preferred embodiment of the invention, are compounds of formula (II), where the

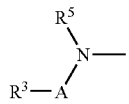

substituent is attached to the 5-position of the benzazole.

Another preferred embodiment of the invention, are compounds of formula (II), where the

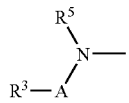

substituent is attached to the 6-position of the benzazole.

Another preferred embodiment of the invention, are compounds of formula (II), where the

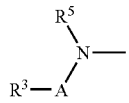

substituent is attached to the 5-position of the benzazole, X represents S; Y represents NH; A represents ←NHCO—, where ← indicates the point of attachment to $R^3$; $R^3$ is an optionally substituted aryl group, $R^5$ represents H.

Another preferred embodiment of the invention, are compounds of formula (II), where the

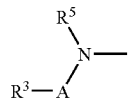

substituent is attached to the 5-position of the benzazole, X represents S; Y represents NH; A represents ←NHCO—, where ← indicates the point of attachment to $R^3$; $R^3$ is an optionally substituted phenyl group, $R^5$ represents H.

Another preferred embodiment of the invention, are compounds of formula (II), where the

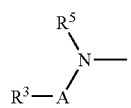

substituent is attached to the 6-position of the benzazole, X represents S; Y represents NH; A represents ←NHCO—, where ← indicates the point of attachment to $R^3$; $R^3$ is an optionally substituted aryl group, $R^5$ represents H.

Another preferred embodiment of the invention, are compounds of formula (II), where the

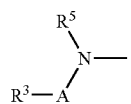

substituent is attached to the 6-position of the benzazole, X represents S; Y represents NH; A represents ←NHCO—, where ← indicates the point of attachment to $R^3$; $R^3$ is an optionally substituted phenyl group, $R^5$ represents H.

Another preferred embodiment of the invention, are compounds of formula (II), where the

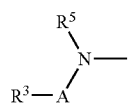

substituent is attached to the 5-position of the benzazole, X represents S; Y represents NH; A represents ←NHCO—, where ← indicates the point of attachment to $R^3$; $R^3$ is an optionally substituted aryl group, $R^5$, $R^{12}$ and $R^{15}$ are H; $R^{13}$ and $R^{14}$ are alkoxy.

Another preferred embodiment of the invention, are compounds of formula (II), where the

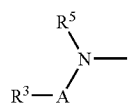

substituent is attached to the 6-position of the benzazole, X represents S; Y represents NH; A represents ←NHCO—, where ← indicates the point of attachment to $R^3$; $R^3$ is an optionally substituted aryl group, $R^5$, $R^{12}$ and $R^{15}$ are H; $R^{13}$ and $R^{14}$ are alkoxy.

Another preferred embodiment of the invention, are compounds of formula (II), where the

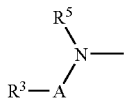

substituent is attached to the 5-position of the benzazole, X represents S; Y represents NH; A represents ←NHCO—, where ← indicates the point of attachment to $R^3$; $R^3$ is an optionally substituted aryl group, $R^5$, $R^{12}$ and $R^{15}$ are H; $R^{13}$ is methoxy.

Another preferred embodiment of the invention, are compounds of formula (II), where the

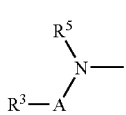

substituent is attached to the 6-position of the benzazole, X represents S; Y represents NH; A represents ←NHCO—, where ← indicates the point of attachment to $R^3$; $R^3$ is an optionally substituted aryl group, $R^5$, $R^{12}$ and $R^{15}$ are H; $R^{13}$ is methoxy.

Another preferred embodiment of the invention, are compounds of formula (II), where the

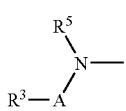

substituent is attached to the 5-position of the benzazole, X represents S; Y represents NH; A represents ←NHCO—, where * indicates the point of attachment to $R^3$; $R^3$ is an optionally substituted aryl group, $R^5$, $R^{12}$ and $R^{15}$ are H; $R^{14}$ is methoxy.

Another preferred embodiment of the invention, are compounds of formula (II), where the

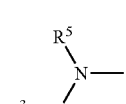

substituent is attached to the 6-position of the benzazole, X represents S; Y represents NH; A represents ←NHCO—, where ← indicates the point of attachment to $R^3$; $R^3$ is an optionally substituted aryl group, $R^5$, $R^{12}$ and $R^{15}$ are H; $R^{14}$ is methoxy.

Another preferred embodiment of the invention, are compounds of formula (IIIa), where the

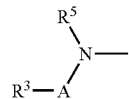

substituent is attached to the 5-position of the benzazole.

Another preferred embodiment of the invention, are compounds of formula (IIIa), where the

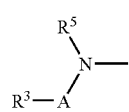

substituent is attached to the 6-position of the benzazole.

A preferred embodiment of the invention, are compounds of formula (I), where $R^1$ is

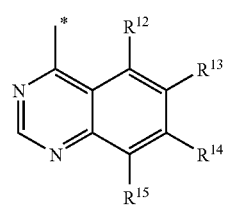

wherein $R^{12}$ and $R^{15}$ are H; $R^{13}$ is methoxy; $R^{14}$ is as defined above;
X represents S; Y represents NH; $R^5$ represents H.

A preferred embodiment of the invention, are compounds of formula (I), where $R^1$ is

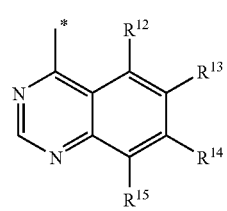

wherein $R^{12}$ and $R^{15}$ are H; $R^{14}$ is methoxy; $R^{13}$ is as defined above;
X represents S; Y represents NH; $R^5$ represents H.

A preferred embodiment of the invention, are compounds of formula (I), where $R^1$ is

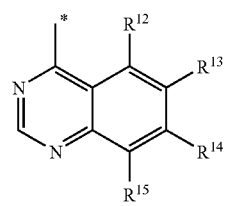

wherein $R^{12}$ and $R^{15}$ are H; $R^{13}$ and $R^{14}$ are alkoxy;
X represents S; Y represents NH; $R^5$ represents H.

A preferred embodiment of the invention, are compounds of formula (Ia), where $R^1$ is

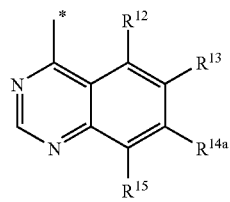

wherein $R^{12}$, $R^{13}$, $R^{14a}$ and $R^{15}$ are as defined above, and where * indicates the point of attachment.

A preferred embodiment of the invention, are compounds of formula (Ia), where $R^1$ is

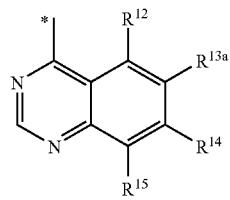

wherein $R^{12}$, $R^{13a}$, $R^{14}$ and $R^{15}$ are as defined above, and where * indicates the point of attachment.

Another preferred embodiment of the invention, are compounds of the formula (IIIb)

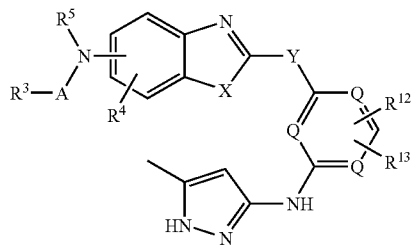

formula (IIIb)

wherein the substituent

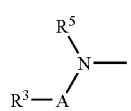

is attached to the 5- or 6-position of the benzazole;
Q independently represents C, N, CH and at least one Q is N;
A, X, Y, $R^3$, $R^4$, $R^5$, $R^{12}$, and $R^{13}$ are as defined above for formula (Ia).

A more preferred embodiment of the invention, are compounds of the formula (IIIc)

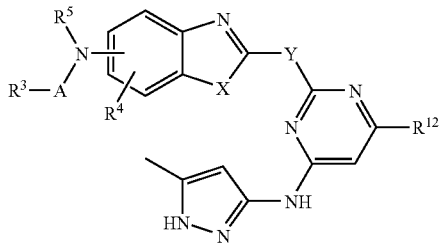

formula (IIIc)

wherein the substituent

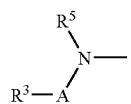

is attached to the 5- or 6-position of the benzazole;
A, X, Y, $R^3$, $R^4$, $R^5$, and $R^{12}$ are as defined above for formula (Ia).

Another preferred embodiment of the invention, are compounds of the formula (IVa)

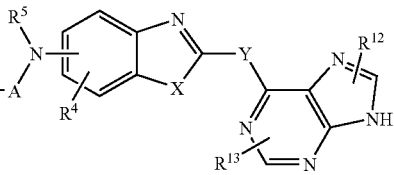

formula (IVa)

wherein the substituent

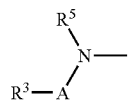

is attached to the 5- or 6-position of the benzazole;
A, X, Y, $R^3$, $R^4$, R', $R^2$, and $R^{13}$ are as defined above for formula (Ia).

Another preferred embodiment of the invention, are compounds of formula (Ia), where
X represents S; Y represents NH; A represents —CO—; $R^5$ represents H.

Another preferred embodiment of the invention, are compounds of formula (Ia), where the

substituent is attached to the 5-position of the benzazole.

Another preferred embodiment of the invention, are compounds of formula (Ia), where the

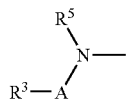

substituent is attached to the 6-position of the benzazole.

A preferred embodiment of the invention, are compounds of formula (Ia), where $R^1$ is

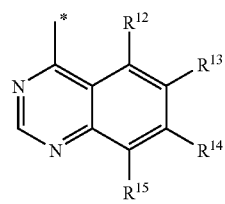

wherein $R^{12}$ and $R^{15}$ are H; $R^{13}$ and $R^{14}$ are alkoxy;
X represents S; Y represents NH; $R^{15}$ represents H.

Another preferred embodiment are compositions containing one ore more compounds of the present invention and a pharmaceutical acceptable carrier or diluent.

The compounds of the present invention to be used according to the invention can form salts with inorganic or organic acids or bases. Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluenesulfonic acid and others.

Salts of phosphonoxy- and phosphonoxyalkyl groups may be those formed with alkali metal ions e.g. sodium or potassium, or those formed with alkaline earth metal ions e.g. calcium or magnesium, or those formed with zinc ions.

Such salts of the compounds of the present invention may be anhydrous or solvated. Such salts can be produced by methods known to someone of skill in the art and described in the prior art.

Other salts like oxalate derived from oxalic acid, which is not considered as pharmaceutically acceptable can be appropriate as intermediates for the production of compounds of the present invention or a pharmaceutically acceptable salt thereof or physiologically functional derivative or a stereoisomer thereof.

The compounds according to the invention and medicaments prepared therewith are generally useful for the treatment of cell proliferation disorders, for the treatment or prophylaxis of immunological diseases and conditions (as for instance inflammatory diseases, neuroimmunological diseases, autoimmune diseases or other).

The compounds of the present invention are useful for the treatment of diseases which are caused by malignant cell proliferation, such as all forms of solid tumors, leukemias and lymphomas. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, myeloma) or lymphomas (e.g. Hodgkin's and non-Hodgkin's lymphomas), or solid tumors (for example breast, prostate, liver, bladder, lung, esophageal, stomach, colorectal, genitourinary, gastrointestinal, skin, pancreatic, brain, uterine, colon, head and neck, cervical, and ovarian, melanoma, astrocytoma, small cell lung cancer, glioma, basal and squameous cell carcinoma, sarcomas as Kaposi's sarcoma and osteosarcoma).

Other aspects of the present invention relate to benzazole derivatives as new pharmaceutically active agents, especially for the preparation of a pharmaceutical composition for the treatment of diseases which are cured or relieved by the inhibition of one or several kinases.

In a preferred embodiment the compounds of the present invention, or compositions thereof, may be used for treating and/or preventing cancer.

In another more preferred embodiment the compounds of the present invention, or compositions thereof, may be used for treating and/or preventing diseases by inhibition of one ore more kinases like: Aurora-A, Aurora-B, EGF-R, ERBB2, PDGFR, FLT3, IGF1-R, VEGF-R2, VEGF-R3, EPHB4, Tie2, FAK and SRC.

The compounds according to the present invention or a pharmaceutically acceptable salt or physiologically functional derivative or a stereoisomer thereof if desired with appropriate adjuvants and additives for the production of a medicament for the treatment or prevention of a disease characterized by hyperproliferation of keratinocytes and/or T cells, especially inflammatory disorders and immune disorders, preferably selected from the group consisting of Addison's disease, alopecia greata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harmman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as *Leishmania*, and immunesuppressed disease states such as viral infections following allograft transplantations, AIDS, cancer, chronic active hepatitis diabetes, toxic chock syndrome and food poisoning.

"Treatment" according to the present invention is intended to mean complete or partial healing of a disease, prevention of a disease, or alleviation of a disease or stop of progression of a given disease.

The compounds of the present invention can further be used for diseases that are caused by protozoal infestations in humans and animals.

The compounds of the present invention can further be used for viral infections or other infections caused for instance by *Pneumocystis carinii*.

Furthermore, the invention relates to a method of treatment or prevention of diseases which comprises the administration of an effective amount of compounds of the formula (I) or a pharmaceutically acceptable salt or physiologically functional derivative or a stereoisomer thereof.

The compounds of the according invention and their pharmacologically acceptable salts can be administered to animals, preferably to mammals, and in particular to humans, as therapeutics per se, as mixtures with one another or in the form of pharmaceutical preparations which allow enteral or parenteral use and which as active constituent contain an effective dose of at least one compound of the present invention or a salt thereof, in addition to customary pharmaceutically innocuous excipients and additives.

The production of medicaments containing the compounds of the present invention and their application can be performed according to well-known pharmaceutical methods.

While the compounds according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds may be anhydrous or solvated.

In a preferred embodiment, the invention provides medicaments comprising compounds according to the present invention, or a pharmaceutically acceptable salt or physiologically functional derivative or a stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

For preparing a medicament from a compounds of the present invention pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In a preferred embodiment of the present invention the medicament is applied topically. This reduces possible side effects and limits the necessary treatment to those areas affected.

Preferably the medicament is prepared in form of an ointment, a gel, a plaster, an emulsion, a lotion, a foam, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Pharmaceutical compositions can also contain two or more compounds of the formula (I) or their pharmacologically acceptable salts and also other therapeutically active substances.

Thus, the compounds of the present invention can be used in the form of one compound alone or in combination with other active compounds—for example with medicaments already known for the treatment of the aforementioned diseases, whereby in the latter case a favorable additive, amplifying effect is noticed.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice. However, those of skill in the art should, in light of the present disclosure, appreciate that many changes can be made in the specific embodiments that are disclosed without departing from the spirit and scope of the invention as set out in the appended claims. All references cited are incorporated herein by reference.

EXAMPLES

Abbreviations: min, minute(s); h, hour(s); r.t., room temperature; $R_t$, retention time; $\Psi$, pseudo; s, singlet; t, triplet, quint, quintet; br., broad; J, coupling constant; pTLC, preparative thin layer chromatography; DMAP, 4-dimethylaminopyridine; GP, general procedure, IM, intermediate.

NMR spectra: Bruker Avance 300 MHz. The $^1$H NMR spectra were recorded at 300 MHz using the residual solvent peak as an internal standard (CDCl$_3$, $\delta_H$=7.26).

Analytical LC/ESI-MS: 2× Waters 600 Multisolvent Delivery System. 50 µl Sample loop. Column, Chromolith Speed ROD RP18e (Merck, Darmstadt), 50×4.6 mm, with 2 µm prefilter (Merck). Eluent A, H$_2$O+0.1% HCO$_2$H; eluent B, MeCN. Gradient, 5% B to 100% B within 5 min; flow, 3 m/min. Waters LCZ single quadrupol mass spectrometer with electrospray source. MS method, MS8minPM-80-800-20V; positive/negative ion mode scanning, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

Preparative HPLC-MS: Waters 600 Multisolvent Delivery System with peparative pump heads. 2000 µl or 5000 µl Sample loop. Column, Waters X-Terra RP18, 7 µm, 19×150 mm with X-Terra RP18 guard cartridge 7 µm, 19×10 mm; used at flow rate 20 ml/min or YMC ODS-A, 120 Å, 40×150 mm with X-Terra RP18 guard cartridge 7 µm, 19×10 mm; used at flow rate 50 ml/min. Make-up solvent: MeCN—H$_2$O—HCO$_2$H 80:20:0.05 (v:v:v). Eluent A, H$_2$O+0.1% HCO$_2$H; eluent B, MeCN. Different linear gradients from 5-100% eluent B, adapted to sample. Injection volume: 500 µl-2000 µl depending on sample. Waters ZQ single quadrupol mass spectrometer with electrospray source. Positive or negative ion mode scanning m/z 80-800 in 1 s; capillary, 3.5 kV or 3.0 kV; cone voltage, 20 V; multiplier voltage, 400 V; probe and desolvation gas temperature, 120° C. and 350° C., respectively. Waters Fraction Collector II with mass-triggered fraction collection. Waters 996 photo diode array detector.

General Procedure 1: Palladium-Catalyzed Cross-Coupling of 2-Amino-benzazole Derivatives and 4-Chloroquinazolines In a Schlenk flask under an argon atmosphere, finely ground water-free potassium phosphate (1.1 equiv) is added to a mixture of the appropriate 2-aminobenzazole (0.2 mmol) and the appropriate 4-chloroquinazoline (0.2 mmol) followed by dry dioxane (1 mL). After addition of 4,5-bis(diphenylphosphino)-9,9-dimethylxanthene (xantphos, 12 µmol) and tris(dibenzylideneacetone)dipalladium (4 µmol, 4 mol-% of Pd), the flask is sealed and heated to 100° C. overnight with stirring. The mixture is allowed to cool to r.t. and the product is obtained by filtration and by chromatography respectively.

Syntheses of 4-chloroquinazolines with Alkylamino Sidechains

Step 1. To a solution of methyl vanillate or methyl isovanillate (7.29 g, 40 mmol) in dimethylformamide (25 mL), potassium carbonate (8.29 g, 60 mmol) and benzyl bromide (5.26 mL, 44 mmol) were added. The mixture was heated to 100° C. for 3 h. After cooling to r.t., water was added and the product was extracted several times with ethyl acetate. The combined organic phases were washed with water and brine. After drying over Na$_2$SO$_4$, the solvent was removed to yield methyl 4-benzyloxy-3-methoxybenzoate or methyl 3-benzyloxy-4-methoxybenzoate, respectively, quantitatively, which was used without further purification.

Step 2. Crude material of step 1 (40.0 mmol) was converted into methyl 4-benzyloxy-5-methoxy-2-nitrobenzoate or methyl 5-benzyloxy-4-methoxy-2-nitrobenzoate, respectively, in 91-94% yield as described in US 02/0026052 A1, page 51, reference example 15.

Step 3. In a 1 l Schlenk flask filled with argon, product of step 2 (36.6 mmol) and palladium on charcoal (1.17 g, 10% Pd, 1.1 mmol Pd) were combined and tetrahydrofuran (250 mL) was added. The argon was replaced with hydrogen (1 bar), and the mixture was vigorously stirred at r.t. until completion of the reaction. The palladium was separated by filtration through a pad of celite and the solvent was removed to obtain methyl 2-amino-4-hydroxy-5-methoxybenzoate or methyl 2-amino-5-hydroxy-4-methoxybenzoate, respectively, quantitatively, which, again, was used without further purification.

Step 4. A mixture of formamide (29 mL), ammonium formate (3.41 g, 54 mmol) and crude material of step 3 (36.0 mmol) was heated to 140° C. for 4 h. After cooling to r.t., water (75 mL) was added. After stirring for 1 h, the precipitated 7-hydroxy-6-methoxy-3,4-dihydroquinazolin-4-one or 6-hydroxy-7-methoxy-3,4-dihydroquinazolin-4-one, respectively, was filtered off, washed with water and dried (76-85%).

Step 5. A mixture of product step 4 (30.5 mmol), acetic anhydride (21.5 mL, 229 mmol) and pyridine (4.9 mL, 61 mmol) was heated to 100° C. for 4 h. After cooling to r.t., ice water (200 mL) was added and the mixture was vigorously stirred for 1 h. The precipitated 7-acetoxy-6-methoxy-3,4-dihydroquinazolin-4-one or 6-acetoxy-7-methoxy-3,4-dihydro-quinazolin-4-one, respectively, was filtered off, washed with water and dried (93-96%).

Step 6. Product step 5 (8.54 mmol) was converted into 4-chloro-7-hydroxy-6-methoxy-quinazoline or 4-chloro-6-hydroxy-7-methoxyquinazoline, respectively, (58-95%) by reacting them with thionylchloride (12 mL) and DMF (0.3 mL) at 85° C. for 1.5 h. Excess thionylchloride was removed by distillation. Traces of thionylchloride were removed by aceotropic distillation wit toluene (two times). Alternatively the products step 5 can be converted into the chlorides by reacting them with a mixture of POCl$_3$ and PCl$_5$. The acetyl groups were removed by hydrolysis with ammonium hydroxide (5 mL, 28-30 wt %) in dioxane/water (100 mL/20 mL) at 0° C. to r.t.

Step 7.

General procedure 4: Mitsunobu reaction

Di-tert-butyl azodicarboxylate (0.478 g, 2.08 mmol) was added portionwise to a mixture of product step 6 (1.66 mmol), the appropriate alcohol (1.74 mmol), and triphenyl-phosphine (0.544 g, 2.08 mmol) in dichloromethane (20 mL) at r.t. If necessary, further alcohol was added. After stirring for 2 h, the solution was concentrated to 10 mL, mounted on silica and chromatographed (gradient, dichloromethane to dichloromethane:methanol=3:2) to obtain the desired ethers (~73%).

General Procedure 2: Reaction of N²-(quinazolin-4-yl)benzazole diamines with acid chlorides The appropriate N²-(quinazolin-4-yl)benzazole diamine (0.113 mmol) is dissolved in pyridine (1 mL). After addition of the appropriate acid chloride (0.113 mmol), the mixture is stirred at 60° C. If necessary, additional acid chloride is added. After completion of the reaction, the mixture is poured into water (20 mL) and the desired product is obtained by filtration.

General Procedure 3: Reaction of N²-(quinazolin-4-yl)benzazole diamines with isocyanates The appropriate N²-(quinazolin-4-yl)benzazole diamine (0.113 mmol) is suspended in dichloromethane (2 mL), and dimethylformamide (1 mL) is added to achieve reasonable dissolution. The appropriate isocyanate (0.113 mmol) is added and the mixture is stirred overnight at r.t.

Syntheses of Intermediates

Intermediate 6: 4-chloro-6-methoxy-7-[3-(4-methylpiperazin-1-yl)propoxy]-quinazoline The compound was synthesised according to GP 4 from 4-chloro-7-hydroxy-6-methoxy-quinazoline and 3-(4-methylpiperazin-1-yl)-propan-1-ol. LC/ESI-MS: m/z=351 [M+H].

Intermediate 8: 4-chloro-7-methoxy-6-[3-(4-methylpiperazin-1-yl)propoxy]-quinazoline The compound was synthesised according to GP 4 from 4-chloro-6-hydroxy-7-methoxy-quinazoline and 3-(4-methylpiperazin-1-yl)-propan-1-ol. LC/ESI-MS: m/z=351 [M+H].

Intermediate 9: 4-chloro-6-methoxy-7-(3-pyrrolidin-1-yl-propoxy)-quinazoline

The compound was synthesised according to GP 4 from 4-chloro-7-hydroxy-6-methoxy-quinazoline and 3-Pyrrolidin-1-yl-propan-1-ol. LC/ESI-MS: m/z=322 [M+H].

Intermediate 10: 4-Chloro-7-methoxy-6-(3-pyrrolidin-1-yl-propoxy)-quinazoline

The compound was synthesised according to GP 4 from 4-chloro-6-hydroxy-7-methoxy-quinazoline and 3-Pyrrolidin-1-yl-propan-1-ol. LC/ESI-MS: m/z=322 [M+H].

Intermediate 11: 4-Chloro-6-methoxy-7-(3-morpholin-4-yl-propoxy)-quinazoline

The compound was synthesised according to GP 4 from 4-chloro-7-hydroxy-6-methoxy-quinazoline. LC/ESI-MS: m/z=338 [M+H].

Intermediate 12: 4-Chloro-7-methoxy-6-(3-morpholin-4-yl-propoxy)-quinazoline

The compound was synthesised according to GP 4 from 4-chloro-6-hydroxy-7-methoxy-quinazoline and 3-Morpholin-4-yl-propan-1-ol. LC/ESI-MS: m/z=338 [M+H].

Intermediate 13: 4-Chloro-6-methoxy-7-[2-(4-methyl-piperazin-1-yl)-ethoxy]-quinazoline The compound was synthesised according to GP 4 from 4-chloro-7-hydroxy-6-methoxy-quinazoline and 2-(4-Methyl-piperazin-1-yl)-ethanol. LC/ESI-MS: m/z=337 [M+H].

Intermediate 14: 4-Chloro-7-methoxy-6-[2-(4-methyl-piperazin-1-yl)-ethoxy]-quinazoline The compound was synthesised according to GP 4 from 4-chloro-6-hydroxy-7-methoxy-quinazoline and 2-(4-Methyl-piperazin-1-yl)-ethanol. LC/ESI-MS: m/z=337 [M+H].

Intermediate 15: 4-Chloro-6-methoxy-7-(2-morpholin-4-yl-ethoxy)-quinazoline

The compound was synthesised according to GP 4 from 4-chloro-7-hydroxy-6-methoxy-quinazoline and 2-Morpholin-4-yl-ethanol. LC/ESI-MS: m/z=324 [M+H].

Intermediate 16: 4-Chloro-7-methoxy-6-(2-morpholin-4-yl-ethoxy)-quinazoline

The compound was synthesised according to GP 4 from 4-chloro-6-hydroxy-7-methoxy-quinazoline and 2-Morpholin-4-yl-ethanol. LC/ESI-MS: m/z=324 [M+H].

Intermediate 17: [3-(4-Chloro-6-methoxy-quinazolin-7-yloxy)-propyl]-dimethyl-amine The compound was synthesised according to GP 4 from 4-chloro-7-hydroxy-6-methoxy-quinazoline and 3-Dimethylamino-propan-1-ol. LC/ESI-MS: m/z=296 [M+H].

Intermediate 18: [2-(4-Chloro-6-methoxy-quinazolin-7-yloxy)-ethyl]-dimethyl-amine The compound was synthesised according to GP 4 from 4-chloro-7-hydroxy-6-methoxy-quinazoline and 2-Dimethylamino-ethanol. LC/ESI-MS: m/z=282 [M+H].

Intermediate 19: 4-Chloro-6-methoxy-7-(1-methyl-piperidin-4-ylmethoxy)-quinazoline The compound was synthesised according to GP 4 from 4-chloro-7-hydroxy-6-methoxy-quinazoline and (1-Methyl-piperidin-4-yl)-methanol. LC/ESI-MS: m/z=322 [M+H].

Intermediate 1: N²-(6,7-dimethoxyquinazolin-4-yl) benzothiazole-2,6-diamine

Step 1. (6,7-Dimethoxyquinazolin-4-yl)-(6-nitrobenzothiazol-2-yl)amine was prepared from 2-amino-6-nitrobenzothiazole (Sigma-Aldrich, 976 mg, 5 mmol) and 4-chloro-6,7-di-methoxyquinazoline (Fluorochem, 1.12 g, 5 mmol) according to GP 1. After filtration, the residue was washed thoroughly with dioxane, water and methanol. After drying in vacuo, crude (6,7-dimethoxy-quinazolin-4-yl)-(6-nitrobenzothiazol-2-yl)amine was obtained as an ochre solid (2.25 g) which was used without further purification. LC/ESI-MS: m/z=384 [M+H]$^+$; m/z=382 [M−H]$^−$; R$_t$=3.67 min.

Step 2. The crude (6,7-dimethoxyquinazolin-4-yl)-(6-nitrobenzothiazol-2-yl)amine (383 mg, 1 mmol) was dissolved in dimethylformamide (100 mL). Palladium on charcoal (106 mg, 10% Pd, 0.1 mmol Pd) was added and the air was replaced with hydrogen (1 bar). The mixture was vigorously stirred for 5 h at 80° C. and then filtered through Celite. After removal of the solvent in vacuo and subsequent drying, pure N$^2$-(6,7-dimethoxyquinazolin-4-yl)benzothiazole-2,6-diamine was obtained as a tawny powder (202 mg, 0.57 mmol, 57%). LC/ESI-MS: m/z=354 [M+H]$^+$; m/z=352 [M−H]$^−$; R$_t$=2.15 mm.

Intermediate 20: N$^2$-{6-Methoxy-7-[3-(4-methyl-piperazin-1-yl)-propoxy]-quinazolin-4-yl}-benzothiazole-2,6-diamine The compound was synthesized according to the procedure described for IM 1 from 4-chloro-6-methoxy-7-[3-(4-methylpiperazin-1-yl)propoxy]quinazoline. LC/ESI-MS: m/z=480 [M+H]$^+$.

Intermediate 21: N$^2$-{6-Methoxy-7-[3-(4-methyl-piperazin-1-yl)-propoxy]-quinazolin-4-yl}-benzooxazole-2,6-diamine The compound was synthesized according to the procedure described for IM 1 from 4-chloro-6-methoxy-7-[3-(4-methylpiperazin-1-yl)propoxy]quinazoline. LC/ESI-MS: m/z=464 [M+H]$^+$.

Intermediate 22: N$^2$-[7-(2-Dimethylamino-ethoxy)-6-methoxy-quinazolin-4-yl]-benzothiazole-2,6-diamine The compound was synthesized according to the procedure described for IM 1 from [2-(4-Chloro-6-methoxy-quinazolin-7-yloxy)-ethyl]-dimethyl-amine. LC/ESI-MS: m/z=411 [M+H]$^+$.

Intermediate 23: N$^2$-[7-(2-Dimethylamino-ethoxy)-6-methoxy-quinazolin-4-yl]-benzooxazole-2,6-diamine The compound was synthesized according to the procedure described for IM 1 from [2-(4-Chloro-6-methoxy-quinazolin-7-yloxy)-ethyl]-dimethyl-amine. LC/ESI-MS: m/z=395 [M+H]$^+$.

Intermediate 26: N$^2$-[6-Methoxy-7-(3-pyrrolidin-1-yl-propoxy)-quinazolin-4-yl]-benzothiazole-2,6-diamine The compound was prepared according to the procedure described for IM 1 starting from IM 9. LC/ESI-MS: m/z=451 [M+H]$^+$.

Intermediate 2: N-(2-Aminobenzothiazol-6-yl)-4-trifluoromethoxybenzamide

To a solution of 6-aminobenzothiazol-2-yl tert-butyl carbamate (Intermediate 4, 0.900 g, 3.39 mmol) in pyridine (8 mL), 4-trifluoromethoxybenzoyl chloride (0.535 mL, 3.39 mmol) was added. After stirring for 2 h at 60° C., the solution was poured into water (100 mL). The resulting precipitate was filtered off, washed with water and dried. The so obtained solid was dissolved in dichloromethane (20 mL) and trifluoroacetic acid (20 mL) was added. After stirring for 3 h at r.t., the volatiles were removed in vacuo and dimethyl-formamide (100 mL) was added to the residue. The solution was neutralised by adding saturated sodium hydrogencarbonate solution. Water (400 mL) was added and the mixture was stirred overnight. The precipitated N-(2-aminobenzothiazol-6-yl)-4-trifluoromethoxy-benzamide was filtered off, washed with water and dried (grey solid, 1.16 g, 3.27 mmol, 84%). LC/ESI-MS: m/z=354 [M+H]$^+$; m/z=352 [M−H]$^−$; R$_t$=3.20 min.

Intermediate 3: 1-(2-Aminobenzothiazol-6-yl)-3-(4-chloro-3-trifluoromethylphenyl) urea A mixture of 6-aminobenzothiazol-2-yl tert-butyl carbamate (Intermediate 4, 0.796 g, 3.0 mmol), 4-chloro-3-(trifluoromethyl)phenyl isocyanate (0.731 g, 3.3 mmol) and dimethylformamide (80 mL) was stirred overnight at r.t. Water was added, the resulting precipitate was filtered off, washed thoroughly with water and dried. The so obtained material was suspended in dichloromethane (15 mL) and trifluoroacetic acid (15 mL) was added. After stirring for 1.5 h at r.t., the volatiles were removed in vacuo and dimethylformamide (20 mL) was added to the residue. The solution was neutralised by adding saturated sodium hydrogencarbonate solution. Water was added and the resulting precipitate was filtered off, washed with water and dried (grey solid, 0.999 g, 2.58 mmol, 86%). LC/ESI-MS: m/z=387 [M($^{35}$Cl)+H]$^+$; m/z=385 [M($^{35}$Cl)−H]$^−$; R$_t$=3.54 min.

Intermediate 4: 6-Aminobenzothiazol-2-yl tert-butyl carbamate

Step 1. To a solution of 2-amino-6-nitrobenzothiazole (Sigma Aldrich, 3.90 g, 20 mmol) and a few mgs of DMAP in dimethylformamide (60 mL), di-tert-butyl dicarbonate (6.55 g, 30 mmol) was added. The mixture was stirred at 90° C. until completion of the reaction. Water (100 mL) and methanol (60 mL) were added. After stirring for 5 min, more water (100 mL) was added. The resulting precipitate was filtered off and washed thoroughly with water and methanol. There was thus obtained 6-nitrobenzothiazol-2-yl tert-butyl carbamate (4.78 g, 16.2 mmol, 81%). LC/ESI-MS: m/z=294 [M−H]$^−$; R$_t$=4.15 min.

Step 2. 6-Nitrobenzothiazol-2-yl tert-butyl carbamate (4.68 g, 15.8 mmol) was dissolved in dimethylformamide (120 mL) and palladium on charcoal (841 mg, 10% Pd, 0.79 mmol Pd) was added. The air was replaced with hydrogen (1 bar) and the mixture was vigorously stirred at 60° C. until completion of the reaction (2 h). The palladium was removed by filtration through a pad of celite and the solution was concentrated to 20 mL. Water (200 mL) was added. After stirring for 1 h, the precipitated 6-aminobenzothiazol-2-yl tert-butyl carbamate was filtered off and washed with water. Additional product was obtained by repeated filtration of the mother liquor. A total of 3.24 g (12.2 mmol, 77%) of a grey solid was obtained. LC/ESI-MS: m/z=266 [M+H]$^+$; m/z=264 [M−H]$^−$; R$_t$=2.54 min.

Intermediate 5: 1-(2-Aminobenzothiazol-5-yl)-3-(4-chloro-3-trifluoromethylphenyl) urea Step 1. Ammonium thiocyanate (8.55 g, 112.5 mmol) was dissolved in acetone (80 mL). Acetyl chloride (8.83 g, 112.5 mmol) was added dropwise. After stirring for 1 h at r.t., the solid was filtered off, and the filtrate was added to a solution of 2-fluoro-5-nitroaniline in acetone (45 mL). The mixture was refluxed for 6 h, then the solution was concentrated and stored overnight at r.t. The precipitated 1-acetyl-3-(2-fluoro-5-nitrophenyl)thiourea was filtered off, washed with acetone and dried. The mother liquor was concentrated and recrystallized from acetone to yield another batch of the product. A total of 12.55 g (48.8 mmol, 43%) of a grey solid was obtained. LC/ESI-MS: m/z=258 [M+H]$^+$; R$_t$=3.42 min. Cf. M. Sedlák, J. Hanusek, M. Holčapek, V. Štěrba, *J. Phys. Org. Chem.* 2001, 14, 187-195.

Step 2. A solution of 1-acetyl-3-(2-fluoro-5-nitrophenyl) thiourea (9.63 g, 37.4 mmol) in methanol (400 mL) was poured quickly into a solution of sodium methanolate (concentration, 0.5 mol/L) in methanol (100 mL). The solution was stored overnight without stirring. The precipitated 2-amino-5-nitrobenzothiazole was filtered off, washed with methanol and dried (yellow crystals, 6.87 g, 35.2 mmol, 94%). LC/ESI-MS: m/z=196 [M+H]$^+$; m/z=194 [M−H]$^-$; R$_t$=2.71 min. Cf. M. Sedlák, J. Hanusek, M. Holčapek, V. Štěrba, *J. Phys. Org. Chem.* 2001, 14, 187-195.

Step 3. To a solution of 2-amino-5-nitrobenzothiazole (3.90 g, 20 mmol) and a few mgs of DMAP in dimethylformamide (150 mL), di-tert-butyl dicarbonate (6.55 g, 30 mmol) was added. The mixture was stirred at 60° C. until completion. Water (30 mL) and methanol (40 mL) were added. After stirring for 5 min, additional water (100 mL) was added, the resulting precipitate was filtered off and washed with water. The solid was redissolved in dimethylformamide with heating, then methanol (40 mL) and water (100 mL) were added and the mixture was stored overnight at r.t. without stirring. After filtration, 5-nitrobenzothiazol-2-yl tert-butyl carbamate was obtained (3.23 g, 10.9 mmol, 55%). LC/ESI-MS: m/z=294 [M−H]$^-$; R$_t$=4.12 min.

Step 4. In a Schlenk flask filled with argon, 5-nitrobenzothiazol-2-yl tert-butyl carbamate (3.23 g, 10.9 mmol) was dissolved in dimethylformamide (120 mL) and ethyl acetate (30 mL). Palladium on charcoal (0.58 g, 10% Pd, 0.55 mmol Pd) was added. The argon was replaced with hydrogen (1 bar) and the mixture was vigorously stirred at 60° C. for 2 h. The palladium was removed by filtration through a pad of celite and the solution was concentrated to 20 mL. Water (200 mL) was added. After stirring for 1 h, the precipitated 5-aminobenzothiazol-2-yl tert-butyl carbamate was filtered off, washed with water and dried (1.45 g, 5.46 mmol, 50%). LC/ESI-MS: m/z=266 [M+H]$^+$; m/z=264 [M−H]$^-$; R$_t$=2.90 min.

Step 5. A mixture of 5-aminobenzothiazol-2-yl tert-butyl carbamate (0.796 g, 3.0 mmol), 4-chloro-3-(trifluoromethyl) phenyl isocyanate (0.731 g, 3.3 mmol) and dimethyl-formamide (50 mL) was stirred for 3 h at r.t. Water was added, the resulting precipitate was filtered off, washed thoroughly with water and dried. The so obtained material was suspended in dichloromethane (15 mL), and trifluoroacetic acid (15 mL) was added. After stirring for 1.5 h at r.t., the volatiles were removed in vacuo and dimethylformamide (20 mL) was added to the residue. The solution was neutralised by adding saturated sodium hydrogencarbonate solution. Water was added and the resulting precipitate was filtered off and washed with water. The solid was redissolved in dimethylformamide and precipitated by addition of water to obtain 1-(2-aminobenzothiazol-5-yl)-3-(4-chloro-3-trifluoromethylphenyl)urea (0.756 g, 1.95 mmol, 65%). LC/ESI-MS: m/z=387 [M($^{35}$Cl)+H]$^+$; m/z=385 [M($^{35}$Cl)−H]$^-$; R$_t$=3.65 min.

Intermediate 24: 1-(2-Amino-benzothiazol-6-yl)-3-(2-methoxy-5-methyl-phenyl)-urea The compound was prepared according to the synthesis of IM 3 with the exception that 2-isocyanato-1-methoxy-4-methyl-benzene was used. LC/ESI-MS: m/z=329 [M+H]$^+$.

Intermediate 25: 1-(2-Amino-benzothiazol-6-yl)-3-(3-methoxy-phenyl)-urea

The compound was prepared according to the synthesis of IM 3 with the exception that 1 Isocyanato-3-methoxy-benzene was used. LC/ESI-MS: m/z=315 [M+H]$^+$.

Intermediate 27: 1-(2-Amino-benzothiazol-6-yl)-3-(2,5-difluoro-phenyl)-urea

The compound was prepared according to the synthesis of IM 3 with the exception that 1,4-Difluoro-2-isocyanato-benzene was used. LC/ESI-MS: m/z=321 [M+H]$^+$.

Intermediate 27: 1-(2-Amino-benzothiazol-6-yl)-3-(3-fluoro-phenyl)-urea

The compound was prepared according to the synthesis of IM 3 with the exception that 1-Fluoro-3-isocyanato-benzene was used. LC/ESI-MS: m/z=303 [M+H]$^+$.

Intermediate 7: 3-(4-Methylpiperazin-1-yl)-propan-1-ol. 1-Methylpiperazine (6.99 mL, 63 mol) was dissolved in toluene (30 mL). 3-Bromopropanol (2.62 mL, 30 mmol) was added slowly and the mixture was stirred overnight. After heating to 80° C. for 2 h and cooling to r.t., the mixture was filtered and the filter cake was washed thoroughly with toluene. After removal of the toluene, the residue was subjected to Kugelrohr distillation (b.p., 180° C./2 mbar) to obtain a colourless oil (4.08 g, 25.8 mmol, 86%). $^1$H NMR (CDCl$_3$): δ=1.70 (Ψ-quint, J≈5.8 Hz, 2 H), 2.26 (s, 3 H), 2.35-2.6 (m, 8 H), 2.60 (Ψ-t, J=5.8 Hz, 2 H), 3.77 (Ψ-t, J=5.3 Hz, 2 H), 4.09 (s, br., 1 H).

Syntheses of the Examples

Example 1

N-[2-(6,7-Dimethoxyquinazolin-4-ylamino)benzothiazol-6-yl]benzamide was prepared from benzoyl chloride (14 μL, 0.113 mmol) and N$^2$-(6,7-dimethoxyquinazolin-4-yl) benzothiazole-2,6-diamine (40 mg, 0.113 mmol) according to GP 2 (yellowish solid, 40 mg, 87 mmol, 77%). LC/ESI-MS: m/z=458 [M+H]$^+$; m/z=456 [M−H]$^-$; R$_t$=3.13 min.

Example 2

N-[2-(6,7-Dimethoxyquinazolin-4-ylamino)benzothiazol-6-yl]-4-methylbenzamide was prepared from p-toluoyl chloride (17.5 mg, 0.113 mmol) and N$^2$-(6,7-dimethoxyquinazolin-4-yl)benzothiazole-2,6-diamine (40 mg, 0.113 mmol) according to GP 2 (yellowish solid, 44 mg, 93 μmol, 82%). LC/ESI-MS: m/z=472 [M+H]$^+$; m/z=470 [M−H]$^-$; R', =3.32 min.

Example 3

N-[2-(6,7-Dimethoxyquinazolin-4-ylamino)-benzothiazol-6-yl]-4-methoxybenzamide was prepared from p-anisoyl chloride (16 μL, 0.113 mmol) and N$^2$-(6,7-dimethoxyquinazolin-4-yl)benzothiazole-2,6-diamine (40 mg, 0.113 mmol) according to GP 2 (yellowish solid, 46 mg, 94 μmol, 83%). LC/ESI-MS: m/z=488 [M+H]$^+$; m/z=486 [M−H]$^-$; R', =3.17 min.

Example 4

N-[2-(6,7-Dimethoxyquinazolin-4-ylamino)benzothiazol-6-yl]-3-methoxybenzamide was prepared from

Example 5

N-[2-(6,7-Dimethoxyquinazolin-4-ylamino)benzothiazol-6-yl]-2-methoxybenzamide was prepared from o-anisoyl chloride (17 μL, 0.113 mmol) and N$^2$-(6,7-dimethoxyquinazolin-4-yl)benzothiazole-2,6-diamine (40 mg, 0.113 mmol) according to GP 2 (yellowish solid, 42 mg, 86 μmol, 76%). LC/ESI-MS: m/z=488 [M+H]$^+$; m/z=486 [M−H]$^-$; R$_t$=3.27 min.

Example 6

4-Chloro-N-[2-(6,7-dimethoxyquinazolin-4-ylamino)benzothiazol-6-yl]benzamide was prepared from p-chlorobenzoyl chloride (15 μL, 0.113 mmol) and N$^2$-(6,7-dimethoxyquinazolin-4-yl)benzothiazole-2,6-diamine (40 mg, 0.113 mmol) according to GP 2 (yellowish solid, 41 mg, 83 μmol, 74%). LC/ESI-MS: m/z=492 [M($^{35}$Cl)+H]$^+$; m/z=490 [M($^{35}$Cl)−H]$^-$; R$_t$=3.45 min.

Example 7

3-Chloro-N-[2-(6,7-dimethoxyquinazolin-4-ylamino)benzothiazol-6-yl]benzamide was prepared from nm-chlorobenzoyl chloride (15 μL, 0.113 mmol) and N$^2$-(6,7-dimethoxyquinazolin-4-yl)benzothiazole-2,6-diamine (40 mg, 0.113 mmol) according to GP 2 (yellowish solid, 42 mg, 85 μmol, 75%). LC/ESI-MS: m/z=492 [M($^{35}$Cl)+H]$^+$; m/z=490 [M($^{35}$Cl)−H]$^-$; R$_t$=3.47 min.

Example 8

3,4-Dichloro-N-[2-(6,7-dimethoxyquinazolin-4-ylamino)benzo-thiazol-6-yl]benzamide was prepared from 3,4-dichlorobenzoyl chloride (24 mg, 0.113 mmol) and N$^2$-(6,7-dimethoxyquinazolin-4-yl)benzothiazole-2,6-diamine (40 mg, 0.113 mmol) according to GP 2 (yellowish solid, 49 mg, 92 μmol, 82%). LC/ESI-MS: m/z=526 [M($^{35}$Cl$_2$)+H]$^+$; m/z=524 [M($^{35}$Cl$_2$)−H]$^-$; R$_t$=3.82 min.

Example 9

N-[2-(6,7-Dimethoxyquinazolin-4-ylamino)benzothiazol-6-yl]-4-trifluoromethylbenzamide was prepared from p-trifluoromethylbenzoyl chloride (17 μL, 0.113 mmol) and N$^2$-(6,7-dimethoxyquinazolin-4-yl)benzothiazole-2,6-diamine (40 mg, 0.113 mmol) according to GP 2 (yellowish solid, 44 mg, 83 μmol, 73%). LC/ESI-MS: m/z=526 [M+H]$^+$; m/z=524 [M−H]$^-$; R$_t$=3.67 min.

Example 10

N-[2-(6,7-Dimethoxyquinazolin-4-ylamino)-benzothiazol-6-yl]-4-trifluoromethoxybenzamide was prepared from 4-chloro-6,7-dimethoxyquinazoline (44.9 mg, 0.2 mmol) and N-(2-aminobenzothiazol-6-yl)-4-trifluoromethoxybenzamide (Intermediate 2, 71 mg, 0.2 mmol) according to GP 1. Dimethylformamide was used as a solvent instead of dioxane. After removal of the solvent in vacuo, the residue was subjected to silica gel chromatography applying a dichloromethane-methanol gradient. The product was then further purified by recrystallisation from dichloromethane (3 mL) to obtain a yellow solid (10 mg, 19 μmol, 9%). LC/ESI-MS: m/z=542 [M+H]$^+$; m/z=540 [M−H]$^-$; R$_t$=3.87 min.

Example 11

N-[2-(6,7-Dimethoxyquinazolin-4-ylamino)-benzothiazol-6-yl]-3-trifluoromethoxybenzamide was prepared from 3-trifluoromethoxybenzoyl chloride (19 μL, 0.113 mmol) and N$^2$-(6,7-dimethoxyquinazolin-4-yl)benzothiazole-2,6-diamine (40 mg, 0.113 mmol) according to GP 2 (yellowish solid, 48 mg, 88 μmol, 78%). LC/ESI-MS: m/z=542 [M+H]$^+$; m/z=540 [M−H]$^-$; R$_t$=3.72 min.

Example 12

1-[2-(6,7-Dimethoxyquinazolin-4-ylamino)benzothiazol-6-yl]-3-phenylurea was prepared from phenyl isocyanate (13 μL, 0.113 mmol) and N$^2$-(6,7-di-methoxyquinazolin-4-yl)benzothiazole-2,6-diamine (40 mg, 0.113 mmol) according to GP 3. The mixture was poured into water (20 mL) and the resulting precipitate was purified by preparative HPLC to obtain a yellow solid (10 mg, 21 μmol, 19%). LC/ESI-MS: m/z=473 [M+H]$^+$; m/z=471 [M−H]$^-$; R$_t$=3.10 min.

Example 13

1-[2-(6,7-Dimethoxyquinazolin-4-ylamino)benzothiazol-6-yl]-3-(3-methoxyphenyl)urea was prepared from 3-methoxyphenyl isocyanate (15 μL, 0.113 mmol) and N$^2$-(6,7-dimethoxyquinazolin-4-yl)benzothiazole-2,6-diamine (40 mg, 0.113 mmol) according to GP 3. The mixture was poured into water (20 mL) and the resulting precipitate was purified by pTLC (dichloromethane:methanol=9:1) to obtain a yellow solid (26 mg, 53 μmol, 46%). LC/ESI-MS: m/z=503 [M+H]$^+$; m/z=501 [M−H]$^-$; R$_t$=3.12 min.

Example 14

1-[2-(6,7-Dimethoxyquinazolin-4-ylamino)benzothiazol-6-yl]-3-(3-fluorophenyl)urea was prepared from 3-fluorophenyl isocyanate (13 μL, 0.113 mmol) and N$^2$-(6,7-dimethoxyquinazolin-4-yl)benzothiazole-2,6-diamine (40 mg, 0.113 mmol) according to GP 3. The mixture was poured into water (20 mL) and the resulting precipitate was purified by pTLC (dichloromethane:methanol=9:1) to obtain a yellow solid (14 mg, 29 μmol, 26%). LC/ESI-MS: m/z=491 [M+H]$^+$; m/z=489 [M−H]$^-$; R$_t$=3.27 min.

Example 15

1-[2-(6,7-Dimethoxyquinazolin-4-ylamino)benzothiazol-6-yl]-3-(3-trifluoromethylphenyl)urea was prepared from 3-trifluoromethylphenyl isocyanate (16 μL, 0.113 mmol) and N$^2$-(6,7-dimethoxyquinazolin-4-yl)benzothiazole-2,6-diamine (40 mg, 0.113 mmol) according to GP 3. The mixture was poured into water (20 mL) and the resulting precipitate was purified by pTLC (dichloromethane:methanol=9:1) to obtain a yellow solid (44 mg, 81 μmol, 72%). LC/ESI-MS: m/z=541 [M+H]$^+$; m/z=539 [M−H]$^-$; R$_t$=3.59 min.

Example 16

1-(4-Chlorophenyl)-3-[2-(6,7-dimethoxyquinazolin-4-ylamino)benzothiazol-6-yl]urea was prepared from 4-chlorophenyl isocyanate (17.4 mg, 0.113 mmol) and N$^2$-(6,7-dimethoxyquinazolin-4-yl)benzothiazole-2,6-diamine (40 mg, 0.113 mmol) according to GP 3. Preparative TLC of the reaction mixture (dichloromethane:methanol=9:1) furnished a yellowish solid (33.9 mg, 67 µmol, 59%). LC/ESI-MS: m/z=507 [M($^{35}$Cl)+H]$^+$; m/z=505 [M($^{35}$Cl)–H]$^-$; R', =3.50 min.

Example 17

1-(4-Chloro-2-trifluoromethylphenyl)-3-[2-(6,7-dimethoxyquinazolin-4-ylamino)benzothiazol-6-yl]urea was prepared from 4-chloro-2-(trifluoromethyl)phenyl isocyanate (17 µL, 0.113 mmol) and N$^2$-(6,7-dimethoxyquinazolin-4-yl)benzothiazole-2,6-diamine (40 mg, 0.113 mmol) according to GP 3. The solid was filtered off and washed thoroughly with dichloromethane to obtain a yellow solid (27 mg, 48 µmol, 42%). LC/ESI-MS: m/z=575 [M($^{35}$Cl)+H]$^+$; m/z=573 [M($^{35}$Cl)–H]$^-$; R$_t$=3.79 min.

Example 18

1-(4-Chloro-3-trifluoromethylphenyl)-3-[2-(6,7-dimethoxyquinazolin-4-ylamino)benzothiazol-6-yl]urea was prepared from 4-chloro-6,7-dimethoxyquinazoline (Fluorochem, 29 mg, 0.13 mmol) and 1-(2-aminobenzothiazol-6-yl)-3-(4-chloro-3-trifluoromethylphenyl)urea (Intermediate 3, 50 mg, 0.13 mmol) according to GP 1. Dimethylformamide was used as a solvent instead of dioxane. After removal of the solvent in vacuo, the residue was subjected to silica gel chromatography applying a dichloromethane-methanol gradient. The crude product was dissolved in dimethylformamide (2 mL) and water was added (2 mL). After storage at 4° C. overnight, the resulting precipitate was filtered off, washed with water and dried to obtain a yellow solid (27 mg, 48 µmol, 37%). LC/ESI-MS: m/z=575 [M($^{35}$Cl)+H]$^+$; m/z=573 [M($^{35}$Cl)–H]$^-$; R$_t$=4.14 min.

Example 19

1-(4-Chloro-3-trifluoromethylphenyl)-3-(2-{6-methoxy-7-[3-(4-methylpiperazin-1-yl)-propoxy]quinazolin-4-ylamino}benzothiazol-6-yl)urea was prepared from 4-chloro-6-methoxy-7-[3-(4-methylpiperazin-1-yl)-propoxy]quinazoline (Intermediate 6, 38.6 mg, 0.11 mmol) and 1-(2-aminobenzothiazol-6-yl)-3-(4-chloro-3-tri-fluoromethylphenyl)urea (Intermediate 3, 42.5 mg, 0.11 mmol) according to GP 1. The crude product was isolated by centrifugation and washed thoroughly with dioxane, methanol, water, and finally methanol. After drying, tetrahydrofuran was added (0.5 mL) and the mixture was filtered through glass wool to obtain pure product (pale yellow solid, 36 mg, 52 µmol, 47%). LC/ESI-MS: m/z=701 [M($^{35}$Cl)+H]$^+$; m/z=699 [M($^{35}$Cl)–H]$^-$; R$_t$=2.88 min.

Example 20

1-(4-Chloro-3-trifluoromethylphenyl)-3-[2-(6,7-dimethoxyquinazolin-4-ylamino)benzothiazol-5-yl]urea was prepared from 4-chloro-6,7-dimethoxyquinazoline (Fluorochem, 29 mg, 0.13 mmol) and 1-(2-aminobenzothiazol-5-yl)-3-(4-chloro-3-trifluoromethylphenyl)urea (Intermediate 5, 50 mg, 0.13 mmol) according to GP 1. Dimethylformamide was used as a solvent instead of dioxane. After removal of the solvent in vacuo, the residue was subjected to silica gel chromatography applying a dichloromethane-methanol gradient. The crude product was dissolved in dimethylformamide (2 mL) and water was added (2 mL). After storing in the fridge overnight, the resulting precipitate was filtered off, washed with water and dried (yellow solid, 7 mg, 12 µmol, 9%). LC/ESI-MS: m/z=575 [M($^{35}$Cl)+H]$^+$; m/z=573 [M($^{35}$Cl)–H]$^-$; R$_t$=4.17 min.

Example 21

1-(4-Chloro-3-trifluoromethylphenyl)-3-[2-(9H-purin-6-ylamino)-benzothiazol-6-yl]urea was prepared from 6-chloropurine (17 mg, 0.11 mmol) and 1-(2-aminobenzothiazol-6-yl)-3-(4-chloro-3-trifluoromethylphenyl)urea (Intermediate 3, 42.5 mg, 0.11 mmol) according to GP 1. The reaction mixture was purified by pTLC (dichloromethane:methanol=9:1) to yield a yellow solid (35.4 mg, 70 µmol, 64%). LC/ESI-MS: m/z=505 [M($^{35}$Cl)+H]$^+$; m/z=503 [M($^{35}$Cl)–H]$^-$; R$_t$=3.87 min.

Example 22

1-[2-(6,7-Dimethoxy-quinazolin-4-ylamino)-benzothiazol-6-yl]-3-(2-methoxy-phenyl)-urea was prepared according to GP 3 starting from intermediate 1.

Example 23

1-[2-(6,7-Dimethoxy-quinazolin-4-ylamino)-benzothiazol-6-yl]-3-(2-methoxy-5-methyl-phenyl)-urea was prepared according to GP 3 starting from intermediate 1.

Example 24

1-(4-Chloro-3-trifluoromethyl-phenyl)-3-[2-(7-hydroxy-6-methoxy-quinazolin-4-ylamino)-benzothiazol-6-yl]-urea was prepared according to GP 1 starting from 4-Chloro-6-methoxy-quinazolin-7-ol and intermediate 3.

Example 25

2-Methoxy-N-(2-{6-methoxy-7-[3-(4-methyl-piperazin-1-yl)-propoxy]-quinazolin-4-ylamino}-benzothiazol-6-yl)-benzamide was prepared according to GP 2 starting from intermediate 20.

Example 26

N-(2-{6-Methoxy-7-[3-(4-methyl-piperazin-1-yl)-propoxy]-quinazolin-4-ylamino}-benzothiazol-6-yl)-benzamide was prepared according to GP 2 starting from intermediate 20.

Example 27

3-Chloro-N-(2-{6-methoxy-7-[3-(4-methyl-piperazin-1-yl)-propoxy]-quinazolin-4-ylamino}-benzothiazol-6-yl)-benzamide was prepared according to GP 2 starting from intermediate 20.

Example 28

4-Methoxy-N-(2-{6-methoxy-7-[3-(4-methyl-piperazin-1-yl)-propoxy]-quinazolin-4-ylamino}-benzothiazol-6-yl)-benzamide was prepared according to GP 2 starting from intermediate 20.

Example 29

N-(2-{6-Methoxy-7-[3-(4-methyl-piperazin-1-yl)-propoxy]-quinazolin-4-ylamino}-benzothiazol-6-yl)-4-methyl-benzamide was prepared according to GP 2 starting from intermediate 20.

Example 30

1-(4-Chloro-3-trifluoromethyl-phenyl)-3-{2-[6-methoxy-7-(3-morpholin-4-yl-propoxy)-quinazolin-4-ylamino]-benzothiazol-6-yl}-urea was prepared according to GP 1 starting from intermediate 11 and intermediate 3.

Example 31

1-(2-Methoxy-5-methyl-phenyl)-3-(2-{6-methoxy-7-[3-(4-methyl-piperazin-1-yl)-propoxy]-quinazolin-4-ylamino}-benzothiazol-6-yl)-urea was prepared according to GP 3 starting from intermediate 20.

Example 32

1-(2-{6-Methoxy-7-[3-(4-methyl-piperazin-1-yl)-propoxy]-quinazolin-4-ylamino}-benzothiazol-6-yl)-3-(2-methoxy-phenyl)-urea was prepared according to GP 3 starting from intermediate 20.

Example 33

1-(2-{6-Methoxy-7-[3-(4-methyl-piperazin-1-yl)-propoxy]-quinazolin-4-ylamino}-benzothiazol-6-yl)-3-(3-methoxy-phenyl)-urea was prepared according to GP 3 starting from intermediate 20.

Example 34

1-(4-Chloro-3-trifluoromethyl-phenyl)-3-(2-{7-methoxy-6-[3-(4-methyl-piperazin-1-yl)-propoxy]-quinazolin-4-ylamino}-benzothiazol-6-yl)-urea was prepared according to GP 1 starting from intermediate 8 and intermediate 3.

Example 35

1-(4-Chloro-3-trifluoromethyl-phenyl)-3-{2-[7-methoxy-6-(3-morpholin-4-yl-propoxy)-quinazolin-4-ylamino]-benzothiazol-6-yl}-urea was prepared according to GP 1 starting from intermediate 12 and intermediate 3.

Example 36

1-(4-Chloro-3-trifluoromethyl-phenyl)-3-{2-[7-methoxy-6-(2-morpholin-4-yl-ethoxy)-quinazolin-4-ylamino]-benzothiazol-6-yl}-urea was prepared according to GP 1 starting from intermediate 16 and intermediate 3.

Example 37

1-(4-Chloro-3-trifluoromethyl-phenyl)-3-{2-[6-methoxy-7-(3-pyrrolidin-1-yl-propoxy)-quinazolin-4-ylamino]-benzothiazol-6-yl}-urea was prepared according to general procedure 1 starting from intermediate 9 and intermediate 3.

Example 38

1-(4-Chloro-3-trifluoromethyl-phenyl)-3-(2-{6-methoxy-7-[2-(4-methyl-piperazin-1-yl)-ethoxy]-quinazolin-4-ylamino}-benzothiazol-6-yl)-urea was prepared according to general procedure 1 starting from intermediate 13 and intermediate 3.

Example 39

1-(4-Chloro-3-trifluoromethyl-phenyl)-3-{2-[6-methoxy-7-(2-morpholin-4-yl-ethoxy)-quinazolin-4-ylamino]-benzothiazol-6-yl}-urea was prepared according to general procedure 1 starting from intermediate 15 and intermediate 3.

Example 40

1-(4-Chloro-3-trifluoromethyl-phenyl)-3-{2-[7-methoxy-6-(3-pyrrolidin-1-yl-propoxy)-quinazolin-4-ylamino]-benzothiazol-6-yl}-urea was synthesized according to general procedure 1 starting from intermediate 10 and intermediate 3.

Example 41

1-(4-Chloro-3-trifluoromethyl-phenyl)-3-(2-{7-methoxy-6-[2-(4-methyl-piperazin-1-yl)-ethoxy]-quinazolin-4-ylamino}-benzothiazol-6-yl)-urea was synthesized according to general procedure 1 starting from intermediate 14 and intermediate 3.

Example 42

1-(2-Methoxy-5-methyl-phenyl)-3-{2-[6-methoxy-7-(3-morpholin-4-yl-propoxy)-quinazolin-4-ylamino]-benzothiazol-6-yl}-urea was synthesized according to general procedure 1 starting from intermediate 11 and intermediate 24.

Example 43

1-(2-Methoxy-5-methyl-phenyl)-3-{2-[6-methoxy-7-(2-morpholin-4-yl-ethoxy)-quinazolin-4-ylamino]-benzothiazol-6-yl}-urea was synthesized according to general procedure 1 starting from intermediate 15 and intermediate 24.

Example 44

1-(2-Methoxy-5-methyl-phenyl)-3-{2-[6-methoxy-7-(3-pyrrolidin-1-yl-propoxy)-quinazolin-4-ylamino]-benzothiazol-6-yl}-urea was synthesized according to general procedure 1 starting from intermediate 9 and intermediate 24.

Example 45

1-(2-Methoxy-5-methyl-phenyl)-3-(2-{6-methoxy-7-[2-(4-methyl-piperazin-1-yl)-ethoxy]-quinazolin-4-ylamino}-benzothiazol-6-yl)-urea was synthesized according to general procedure 1 starting from intermediate 13 and intermediate 24.

Example 46

1-(2,4-Difluoro-phenyl)-3-(2-{6-methoxy-7-[3-(4-methyl-piperazin-1-yl)-propoxy]-quinazolin-4-ylamino}-benzothiazol-6-yl)-urea was synthesized according to general procedure 3 starting from intermediate 20.

Example 47

1-(2-Fluoro-5-trifluoromethyl-phenyl)-3-(2-{6-methoxy-7-[3-(4-methyl-piperazin-1-yl)-propoxy]-quinazolin-4-ylamino}-benzothiazol-6-yl)-urea was synthesized according to general procedure 3 starting from intermediate 20.

Example 48

1-(4-Dimethylamino-phenyl)-3-(2-{6-methoxy-7-[3-(4-methyl-piperazin-1-yl)-propoxy]-quinazolin-4-ylamino}- benzothiazol-6-yl)-urea was synthesized according to general procedure 3 starting from intermediate 20.

Example 49

1-(2-Methoxy-5-methyl-phenyl)-3-{2-[6-methoxy-7-(1-methyl-piperidin-4-ylmethoxy)-quinazolin-4-ylamino]-benzothiazol-6-yl}-urea was prepared according to the general procedure 1 starting from intermediate 19 and intermediate 24.

Example 50

1-(2,5-Difluoro-phenyl)-3-(2-{6-methoxy-7-[3-(4-methyl-piperazin-1-yl)-propoxy]-quinazolin-4-ylamino}-benzothiazol-6-yl) was synthesized according to general procedure 3 starting from intermediate 20.

Example 51

1-(2-Fluoro-5-methyl-phenyl)-3-(2-{6-methoxy-7-[3-(4-methyl-piperazin-1-yl)-propoxy]-quinazolin-4-ylamino}-benzothiazol-6-yl)-urea was synthesized according to general procedure 3 starting from intermediate 20.

Example 52

1-(4-Chloro-3-trifluoromethyl-phenyl)-3-{2-[7-(3-dimethylamino-propoxy)-6-methoxy-quinazolin-4-ylamino]-benzothiazol-6-yl}-urea was prepared according to the general procedure 1 starting from intermediate 17 and intermediate 3.

Example 53

1-{2-[7-(3-Dimethylamino-propoxy)-6-methoxy-quinazolin-4-ylamino]-benzothiazol-6-yl}-3-(2-methoxy-5-methyl-phenyl)-urea was prepared according to the general procedure 1 starting from intermediate 17 and intermediate 24.

Example 54

1-(2-Chloro-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 55

1-(2-{6-Methoxy-7-[3-(4-methyl-piperazin-1-yl)-propoxy]-quinazolin-4-ylamino}-benzothiazol-6-yl)-3-o-tolyl-urea was prepared according to general procedure 3 starting from intermediate 20.

Example 56

1-(2,5-Dimethoxy-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 57

1-(2,4-Dimethoxy-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 58

1-(2-{6-Methoxy-7-[3-(4-methyl-piperazin-1-yl)-propoxy]-quinazolin-4-ylamino}-benzothiazol-6-yl)-3-(2-trifluoromethoxy-phenyl)-urea was prepared according to general procedure 3 starting from intermediate 20.

Example 59

3-Methoxy-N-(2-{6-methoxy-7-[3-(4-methyl-piperazin-1-yl)-propoxy]-quinazolin-4-ylamino}-benzothiazol-6-yl)-benzamide was prepared according to general procedure 2 starting from intermediate 20.

Example 60

Cyclopropanecarboxylic acid (2-{6-methoxy-7-[3-(4-methyl-piperazin-1-yl)-propoxy]-quinazolin-4-ylamino}-benzothiazol-6-yl)-amide was prepared according to general procedure 2 starting from intermediate 20.

Example 61

1-(5-Chloro-2-methoxy-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 62

1-(2-Chloro-5-trifluoromethyl-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 63

1-(2-Methoxy-5-methyl-phenyl)-3-(2-{6-methoxy-7-[3-(4-methyl-piperazin-1-yl)-propoxy]-quinazolin-4-ylamino}-benzooxazol-6-yl)-urea was prepared according to general procedure 3 starting from intermediate 21.

Example 64

1-(4-Chloro-3-trifluoromethyl-phenyl)-3-(2-{6-methoxy-7-[3-(4-methyl-piperazin-1-yl)-propoxy]-quinazolin-4-ylamino}-benzooxazol-6-yl)-urea was prepared according to general procedure 3 starting from intermediate 21.

Example 65

1-(2-{6-Methoxy-7-[3-(4-methyl-piperazin-1-yl)-propoxy]-quinazolin-4-ylamino}-benzothiazol-6-yl)-3-phenyl-urea was prepared according to GP 3 starting from intermediate 20.

Example 66

1-(4-Chloro-3-trifluoromethyl-phenyl)-3-{2-[7-(2-dimethylamino-ethoxy)-6-methoxy-quinazolin-4-ylamino]-benzothiazol-6-yl}-urea was prepared according to general procedure 3 starting from intermediate 22.

Example 67

1-{2-[7-(2-Dimethylamino-ethoxy)-6-methoxy-quinazolin-4-ylamino]-benzothiazol-6-yl}-3-(2-methoxy-5-methyl-phenyl)-urea was prepared according to general procedure 3 starting from intermediate 22.

Example 68

1-(2,5-Difluoro-phenyl)-3-{2-[7-(2-dimethylamino-ethoxy)-6-methoxy-quinazolin-4-ylamino]-benzothiazol-6-yl}-urea was prepared according to general procedure 3 starting from intermediate 22.

Example 69

1-{2-[7-(2-Dimethylamino-ethoxy)-6-methoxy-quinazolin-4-ylamino]-benzothiazol-6-yl}-3-(2-fluoro-5-trifluoromethyl-phenyl)-urea was prepared according to general procedure 3 starting from intermediate 22.

Example 70

1-{2-[7-(2-Dimethylamino-ethoxy)-6-methoxy-quinazolin-4-ylamino]-benzothiazol-6-yl}-3-(3-methoxy-phenyl)-urea was prepared according to general procedure 3 starting from intermediate 22.

Example 71

1-{2-[7-(3-Dimethylamino-propoxy)-6-methoxy-quinazolin-4-ylamino]-benzothiazol-6-yl}-3-(3-methoxy-phenyl)-urea was prepared according to general procedure 1 starting from intermediate 17 and intermediate 25.

Example 72

1-(3-Methoxy-phenyl)-3-{2-[6-methoxy-7-(3-pyrrolidin-1-yl-propoxy)-quinazolin-4-ylamino]-benzothiazol-6-yl}-urea was prepared according to the general procedure 1 starting from intermediate 9 and intermediate 25.

Example 73

1-(4-Fluoro-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 74

1-(2,4-Difluoro-phenyl)-3-{2-[6-methoxy-7-(3-pyrrolidin-1-yl-propoxy)-quinazolin-4-ylamino]-benzothiazol-6-yl}-urea was prepared according to general procedure 3 starting from intermediate 26.

Example 75

1-(2,5-Difluoro-phenyl)-3-{2-[6-methoxy-7-(3-pyrrolidin-1-yl-propoxy)-quinazolin-4-ylamino]-benzothiazol-6-yl}-urea was prepared according to general procedure 1 starting from intermediate 9 and intermediate 27.

Example 76

1-(3-Cyano-phenyl)-3-{2-[6-methoxy-7-(3-pyrrolidin-1-yl-propoxy)-quinazolin-4-ylamino]-benzothiazol-6-yl}-urea was prepared according to general procedure 3 starting from intermediate 26.

Example 77

1-{2-[6-Methoxy-7-(3-morpholin-4-yl-propoxy)-quinazolin-4-ylamino]-benzothiazol-6-yl}-3-(3-methoxy-phenyl)-urea was prepared according to general procedure 1 starting from intermediate 11 and intermediate 25.

Example 78

1-(4-Fluoro-phenyl)-3-{2-[6-methoxy-7-(3-pyrrolidin-1-yl-propoxy)-quinazolin-4-ylamino]-benzothiazol-6-yl}-urea was prepared according to general procedure 3 starting from intermediate 26.

Example 79

1-(3-Fluoro-phenyl)-3-(2-{6-methoxy-7-[3-(4-methyl-piperazin 1-yl)-propoxy]-quinazolin-4-ylamino}-benzothiazol-6-yl)-urea was prepared according to general procedure 3 starting from intermediate 20.

Example 80

1-(4-Cyano-phenyl)-3-(2-{6-methoxy-7-[3-(4-methyl-piperazin-1-yl)-propoxy]-quinazolin-4-ylamino}-benzothiazol-6-yl)-urea was prepared according to general procedure 3 starting from intermediate 20.

Example 81

1-(3-Fluoro-phenyl)-3-{2-[6-methoxy-7-(3-pyrrolidin-1-yl-propoxy)-quinazolin-4-ylamino]-benzothiazol-6-yl}-urea was prepared according to general procedure 1 starting from intermediate 9 and intermediate 28.

Analytical data of compounds of the present invention of formula (I):

| Example | Compound Structure | LC/ESI-MS: [M + H] m/z = | Rt |
|---|---|---|---|
| 12 | 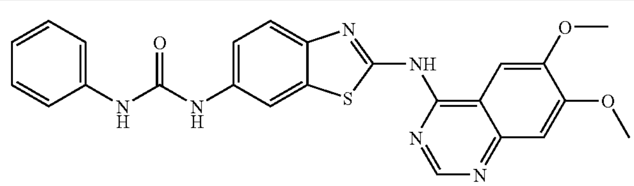 | 473 | 3.10 |

| Example | Compound Structure | LC/ESI-MS: [M + H] m/z = | Rt |
|---|---|---|---|
| 13 | 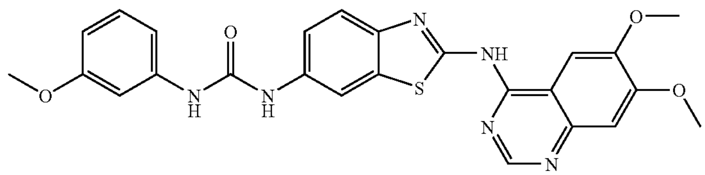 | 503 | 3.12 |
| 14 | 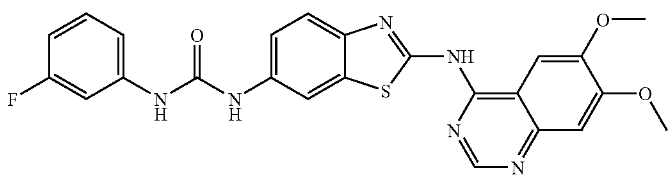 | 491 | 3.27 |
| 15 | 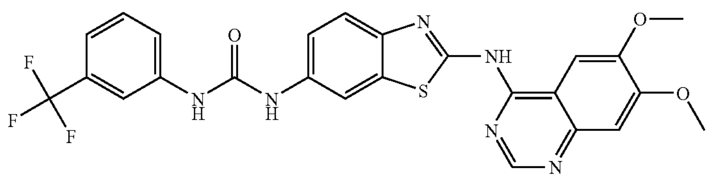 | 541 | 3.55 |
| 16 | 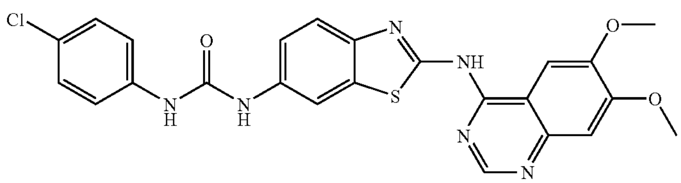 | 507 | 3.50 |
| 17 | 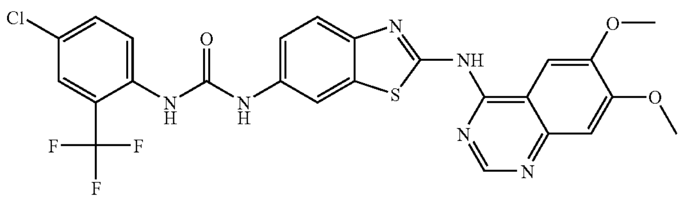 | 575 | 3.70 |
| 18 | 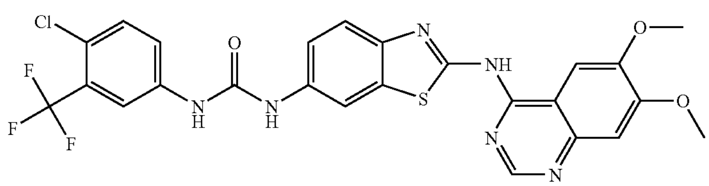 | 575 | 4.18 |

-continued

| Example | Compound Structure | LC/ESI-MS: [M + H] m/z = | Rt |
|---|---|---|---|
| 19 | 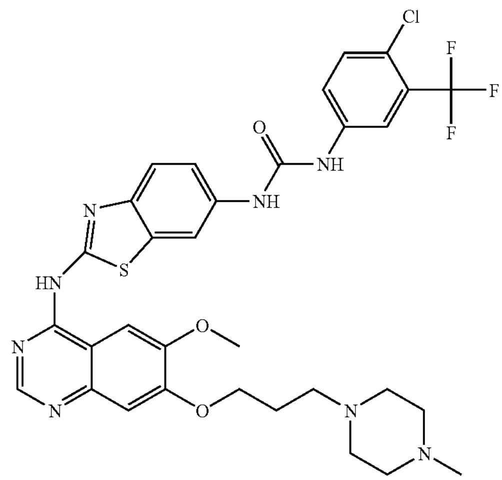 | 701 | 2.95 |
| 20 | 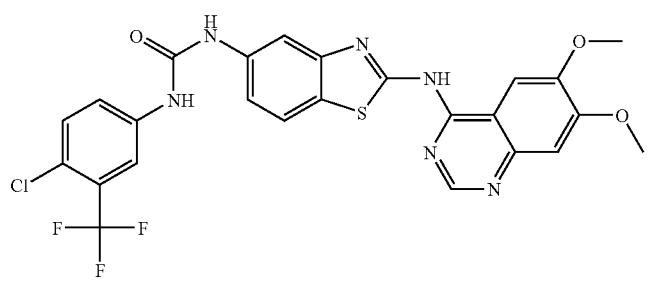 | 575 | 4.17 |
| 21 | 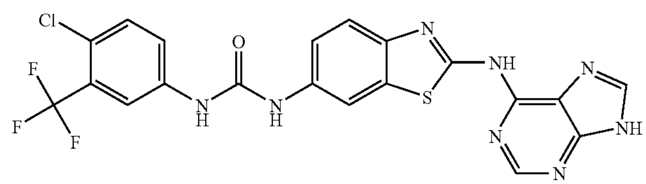 | 505 | 3.90 |
| 22 | 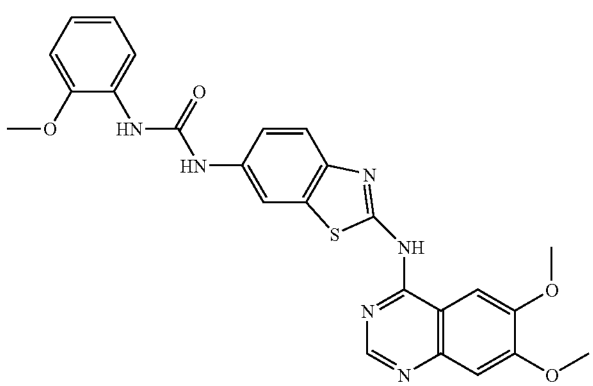 | 503 | 3.17 |

-continued

| Example | Compound Structure | LC/ESI-MS: [M + H] m/z = | Rt |
|---|---|---|---|
| 23 | 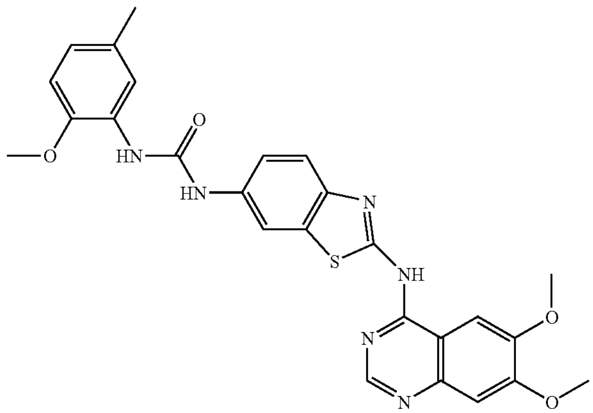 | 517 | 3.38 |
| 24 | 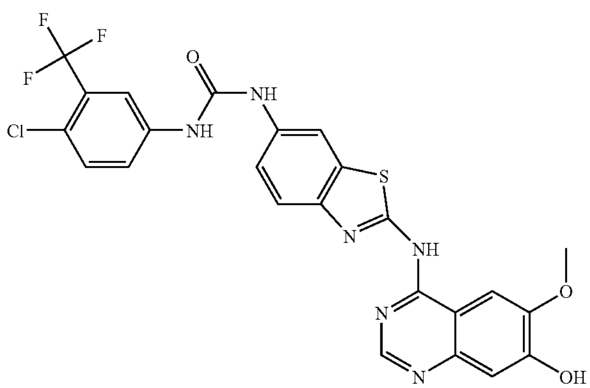 | 561 | 3.48 |
| 30 | 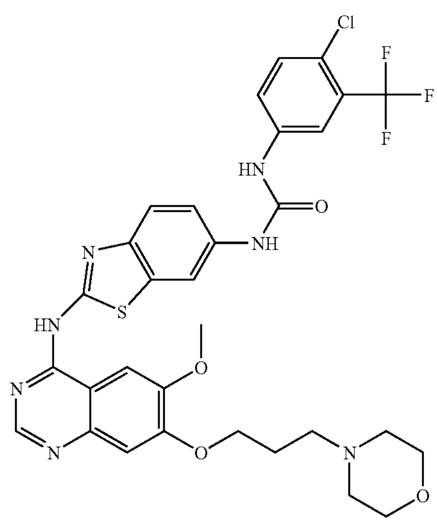 | 688 | 3.37 |

US 7,514,460 B2
-continued
| Example | Compound Structure | LC/ESI-MS: [M + H] m/z = | Rt |
|---|---|---|---|
| 31 | 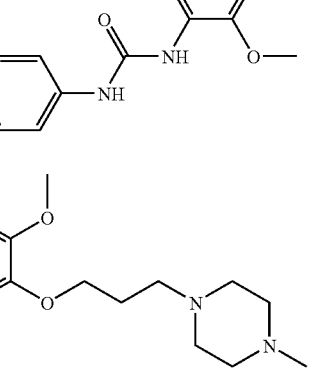 | 643 | 2.75 |
| 32 | 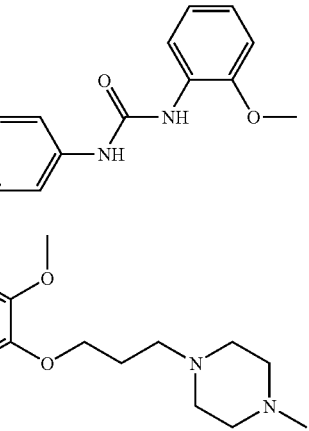 | 629 | 2.68 |
| 33 | 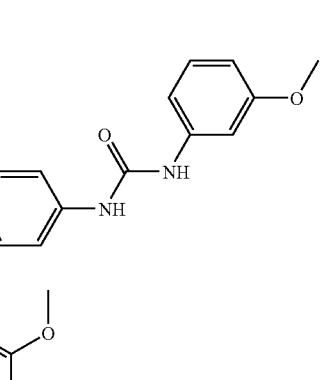 | 629 | 2.57 |

-continued

| Example | Compound Structure | LC/ESI-MS: [M + H] m/z = | Rt |
|---|---|---|---|
| 34 | 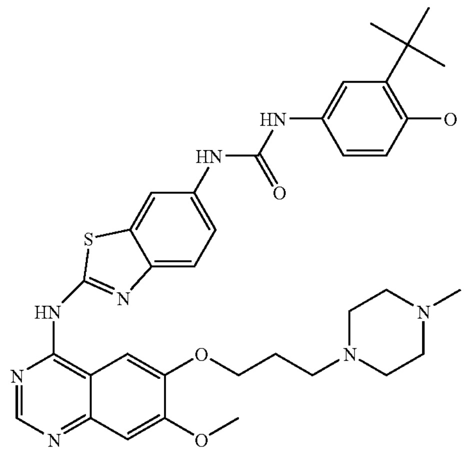 | 701 | 3.23 |
| 35 | 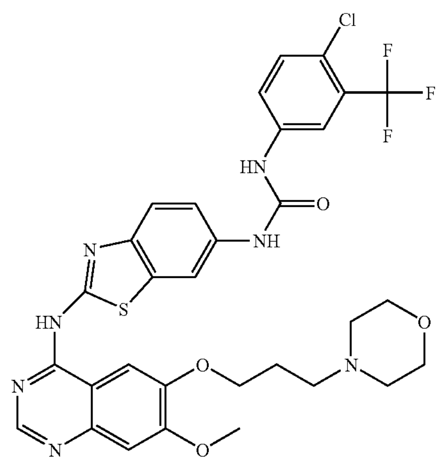 | 688 | 3.59 |
| 36 | 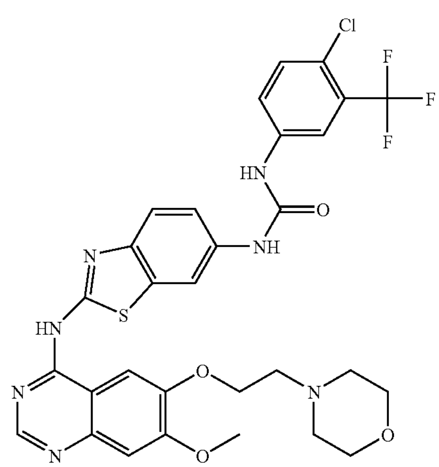 | 674 | 3.38 |

-continued

| Example | Compound Structure | LC/ESI-MS: [M + H] m/z = | Rt |
|---|---|---|---|
| 37 | 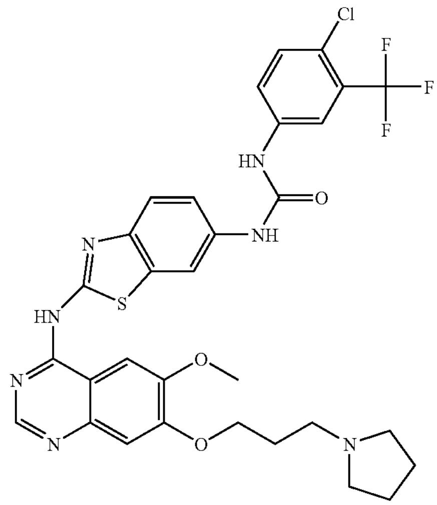 | 672 | 3.35 |
| 38 | 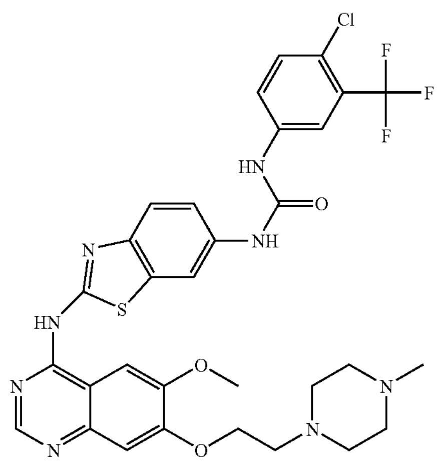 | 687 | 3.13 |
| 39 | 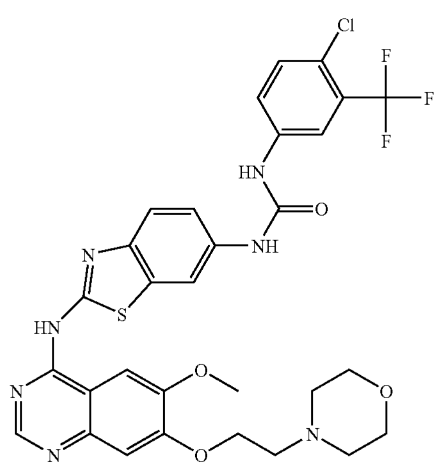 | 674 | 3.37 |

-continued
| Example | Compound Structure | LC/ESI-MS: [M + H] m/z = | Rt |
|---|---|---|---|
| 40 | 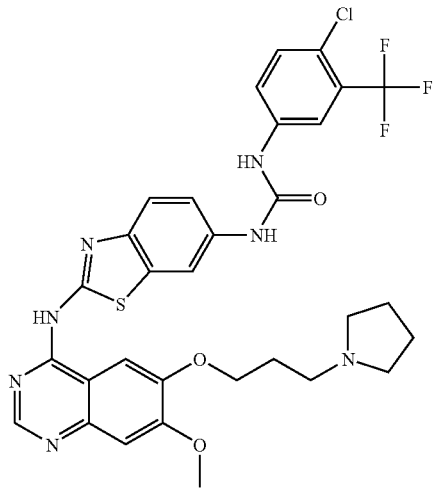 | 672 | 3.45 |
| 41 | 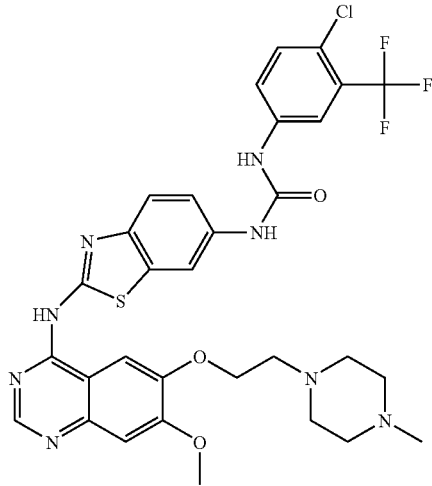 | 687 | 3.15 |
| 42 | 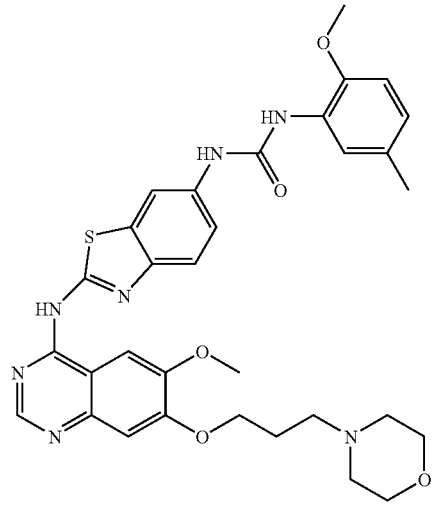 | 630 | 2.84 |

-continued

| Example | Compound Structure | LC/ESI-MS: [M + H] m/z = | Rt |
|---|---|---|---|
| 43 | 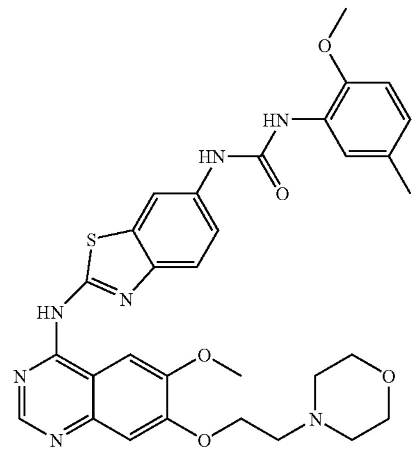 | 616 | 2.95 |
| 44 | 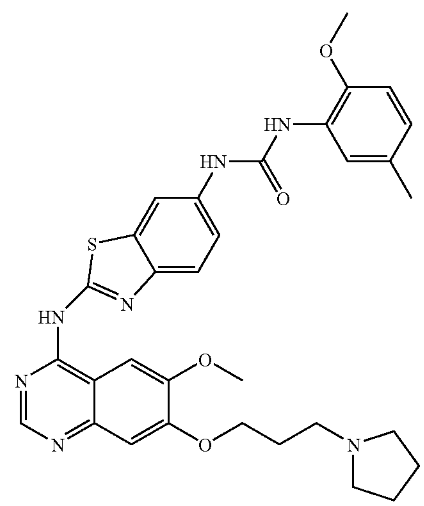 | 614 | 2.98 |
| 45 | 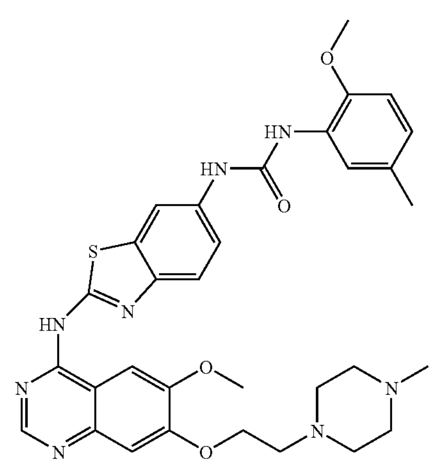 | 629 | 2.84 |

-continued

| Example | Compound Structure | LC/ESI-MS: [M + H] m/z = | Rt |
|---|---|---|---|
| 46 | 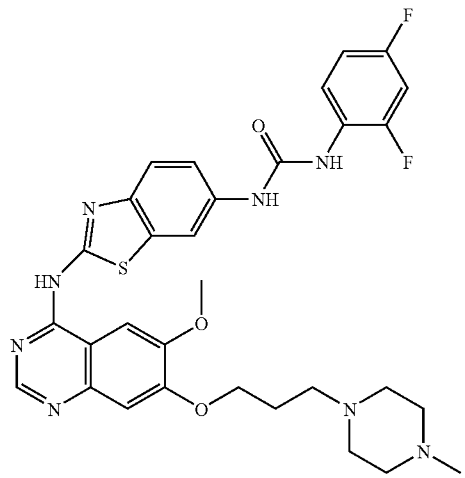 | 635 | 2.87 |
| 47 | 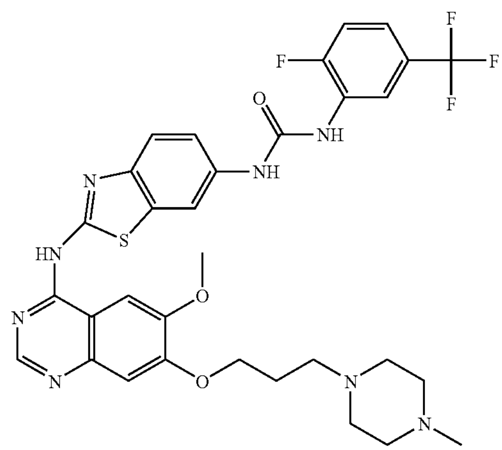 | 685 | 3.32 |
| 48 | 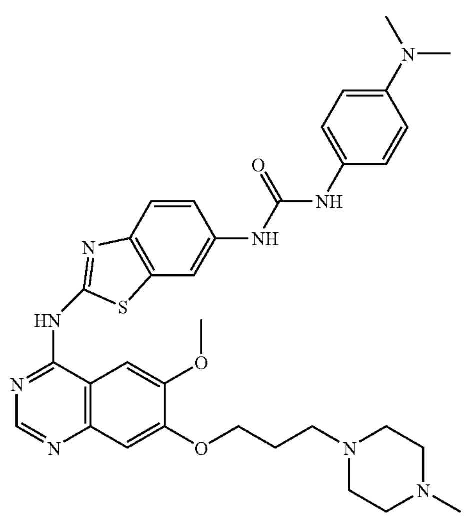 | 642 | 2.25 |

-continued

| Example | Compound Structure | LC/ESI-MS: [M + H] m/z = | Rt |
|---|---|---|---|
| 49 | 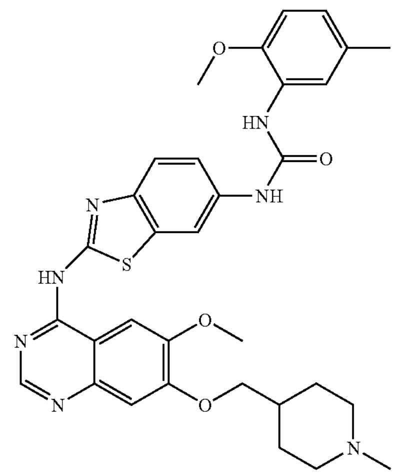 | 614 | 3.35 |
| 50 | 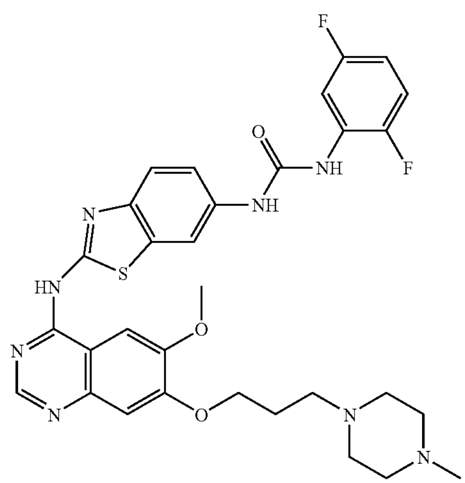 | 635 | 3.04 |
| 51 | 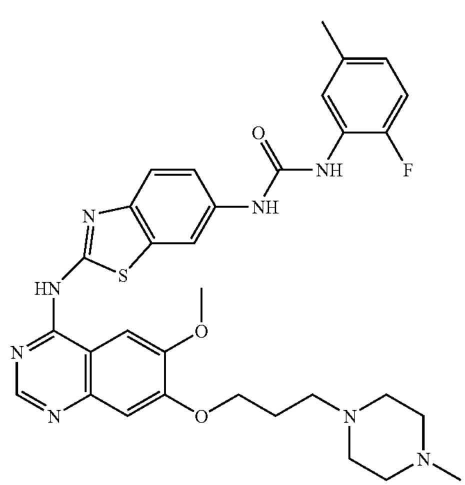 | 631 | 2.95 |

-continued
| Example | Compound Structure | LC/ESI-MS: [M + H] m/z = | Rt |
|---|---|---|---|
| 52 | 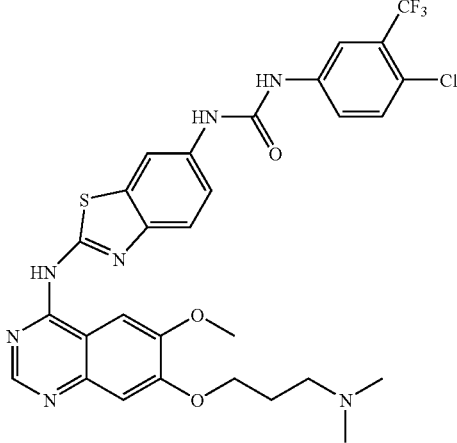 | 646 | 3.38 |
| 53 | 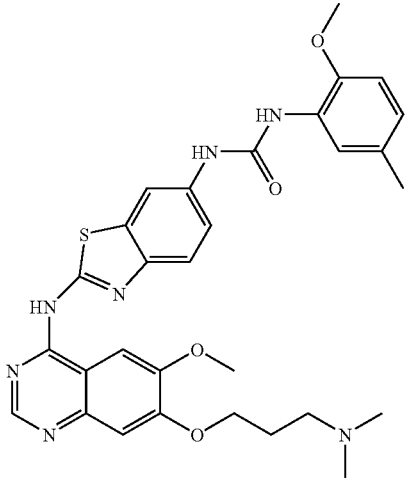 | 588 | 2.90 |
| 54 | 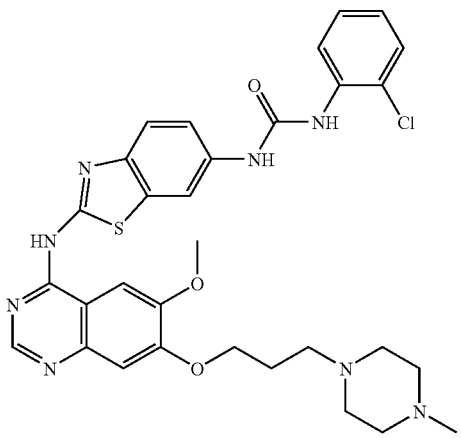 | 633 | 2.87 |

| Example | Compound Structure | LC/ESI-MS: [M + H] m/z = | Rt |
| --- | --- | --- | --- |
| 55 | 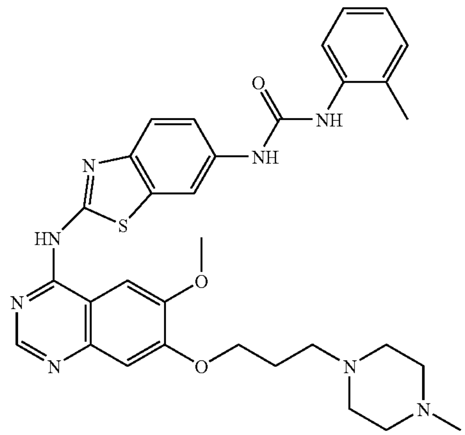 | 613 | 2.77 |
| 56 | 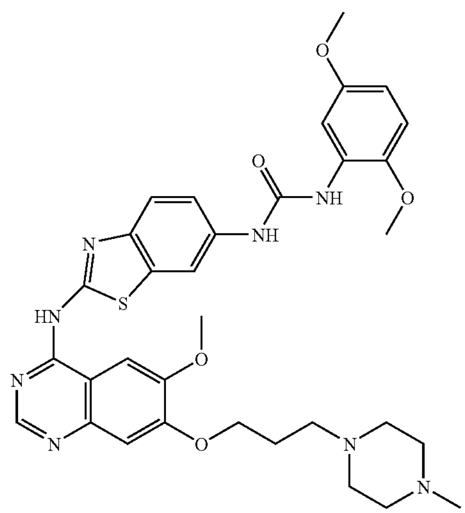 | 659 | 2.77 |
| 57 | 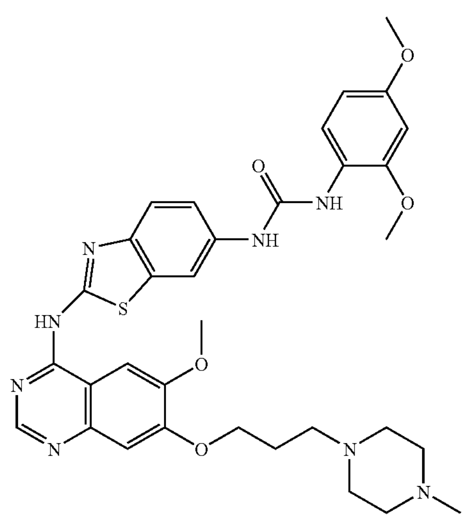 | 659 | 2.72 |

| Example | Compound Structure | LC/ESI-MS: [M + H] m/z = | Rt |
|---|---|---|---|
| 58 | 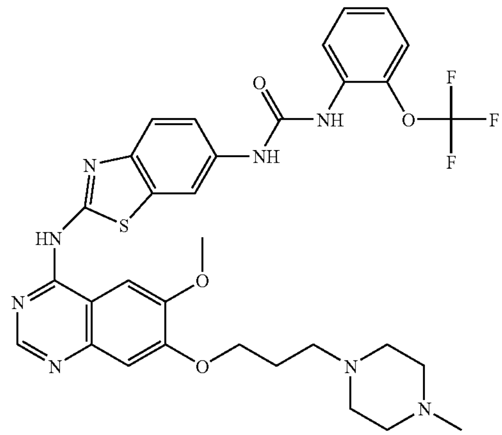 | 683 | 3.09 |
| 61 | 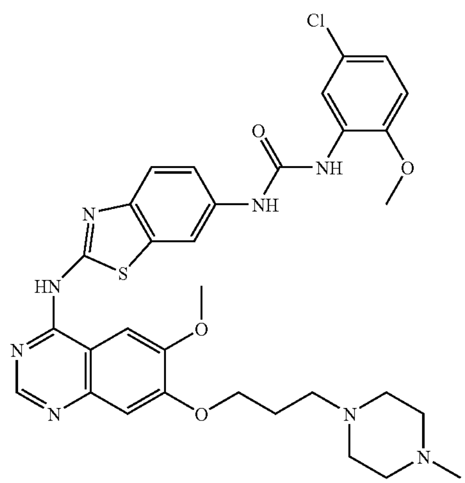 | 663 | 3.12 |
| 62 | 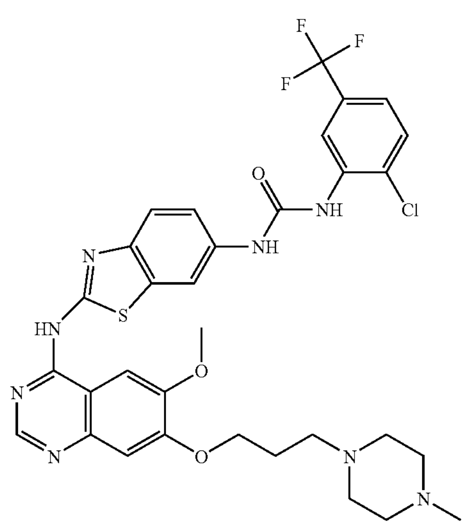 | 701 | 3.20 |

-continued

| Example | Compound Structure | LC/ESI-MS: [M + H] m/z = | Rt |
|---|---|---|---|
| 63 | 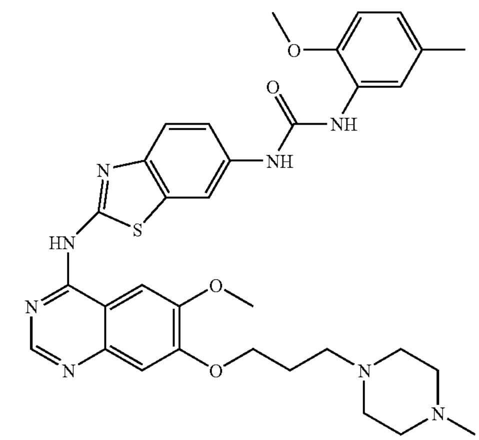 | 627 | 3.15 |
| 64 | 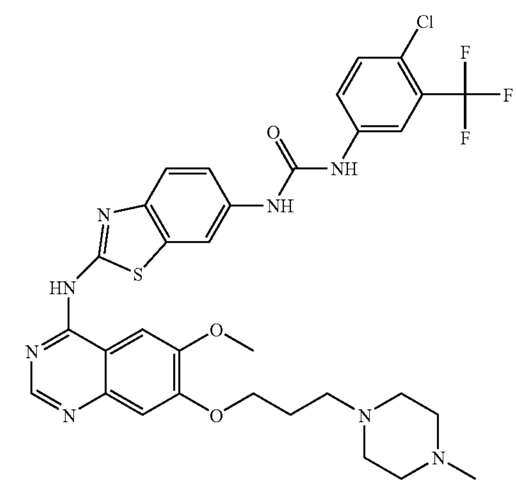 | 685 | 3.50 |
| 65 | 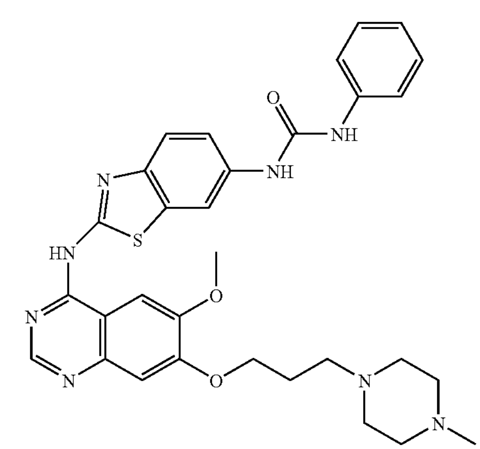 | 599 | 2.82 |

-continued

| Example | Compound Structure | LC/ESI-MS: [M + H] m/z = | Rt |
|---|---|---|---|
| 66 | 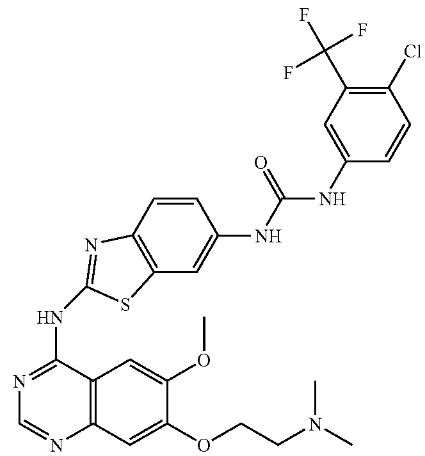 | 632 | 3.27 |
| 67 | 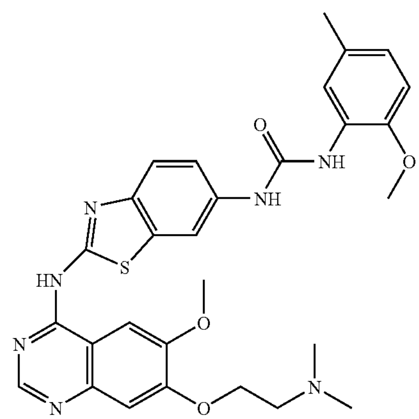 | 574 | 3.09 |
| 68 | 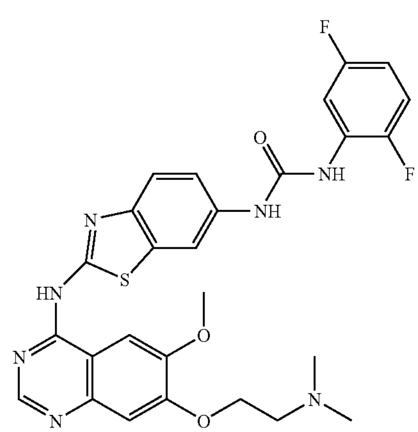 | 566 | 3.12 |

-continued

| Example | Compound Structure | LC/ESI-MS: [M + H] m/z = | Rt |
|---|---|---|---|
| 69 | 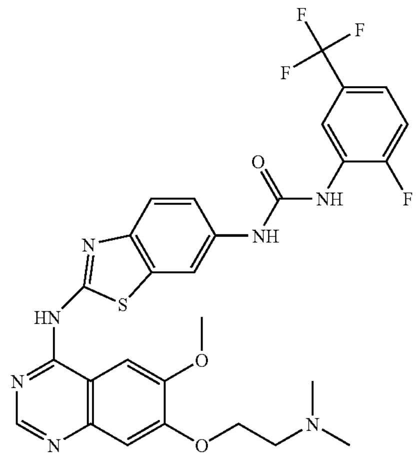 | 616 | 3.22 |
| 70 | 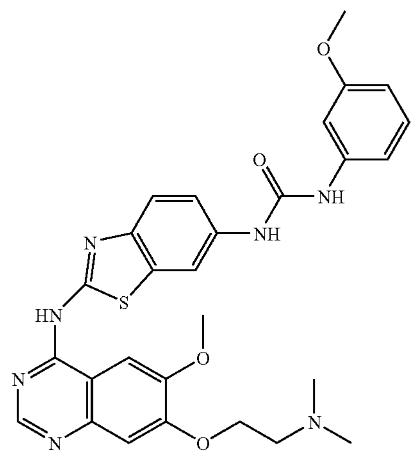 | 560 | 2.80 |
| 71 | 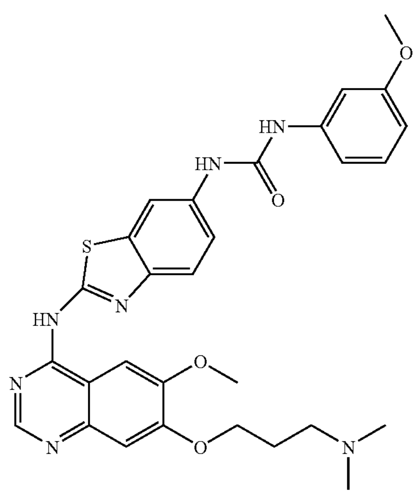 | 574 | 2.85 |

-continued

| Example | Compound Structure | LC/ESI-MS: [M + H] m/z = | Rt |
|---|---|---|---|
| 72 | 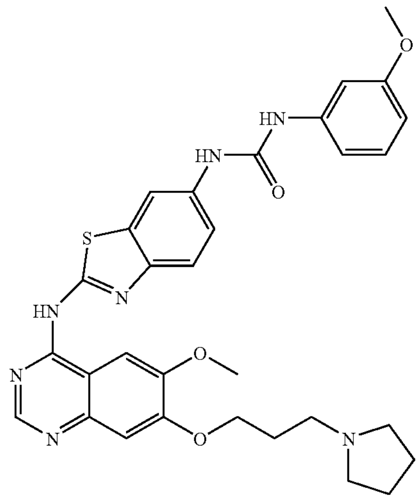 | 600 | 3.55 |
| 73 | 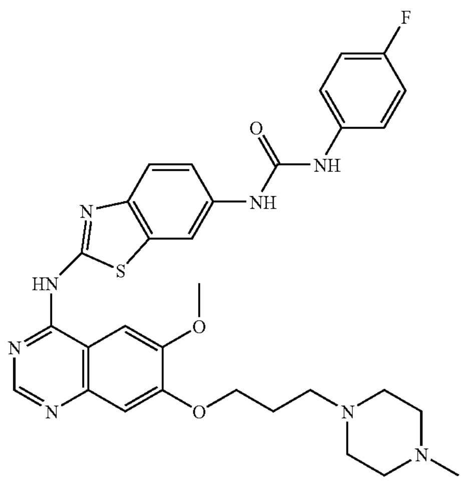 | 617 | 2.90 |
| 74 | 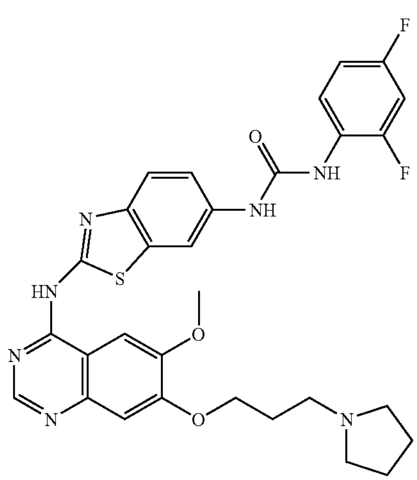 | 606 | 3.29 |

| Example | Compound Structure | LC/ESI-MS: [M + H] m/z = | Rt |
|---|---|---|---|
| 75 | 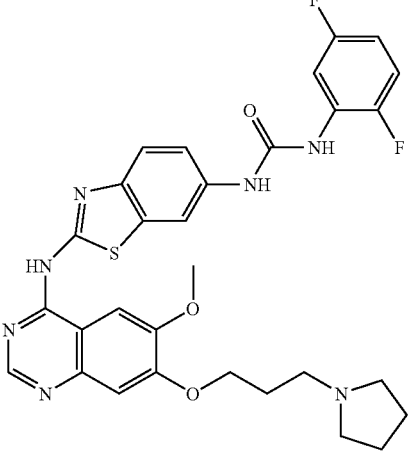 | 606 | 3.59 |
| 76 | 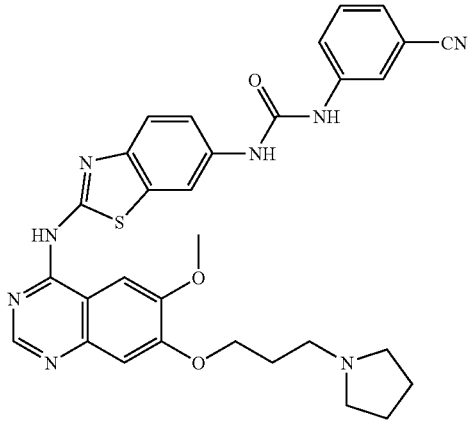 | 595 | 3.13 |
| 77 | 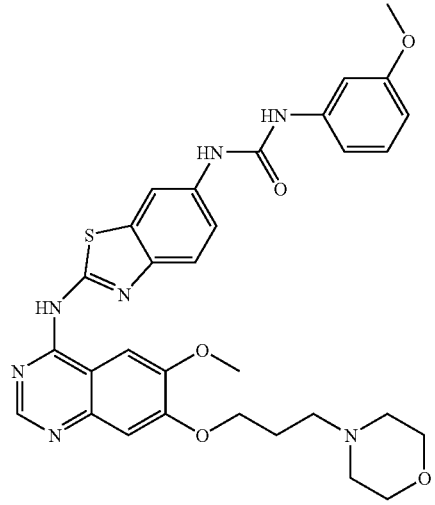 | 616 | 3.04 |

-continued

| Example | Compound Structure | LC/ESI-MS: [M + H] m/z = | Rt |
|---|---|---|---|
| 78 | 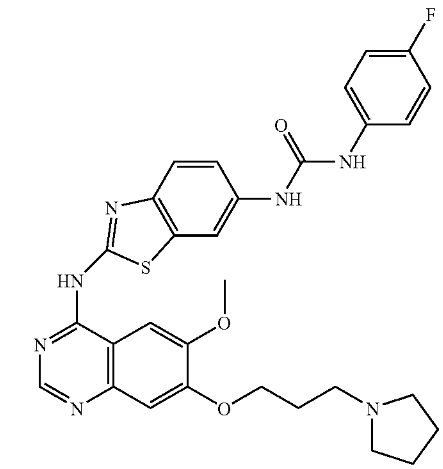 | 588 | 3.42 |
| 79 | 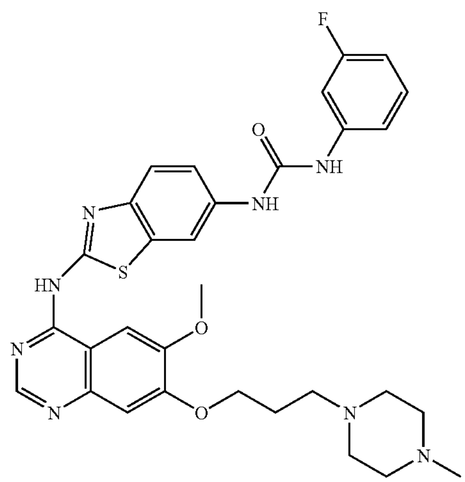 | 617 | 3.15 |
| 80 | 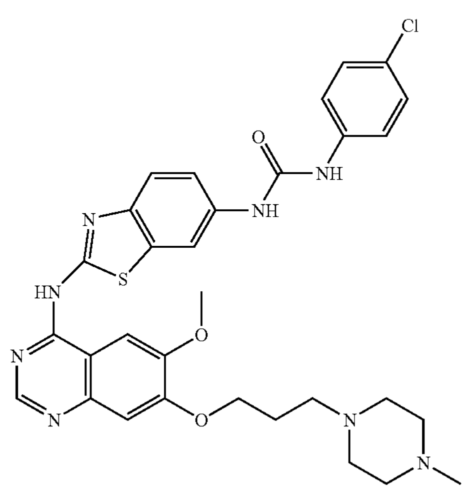 | 624 | 3.07 |

| Example | Compound Structure | LC/ESI-MS: [M + H] m/z = | Rt |
|---|---|---|---|
| 81 | 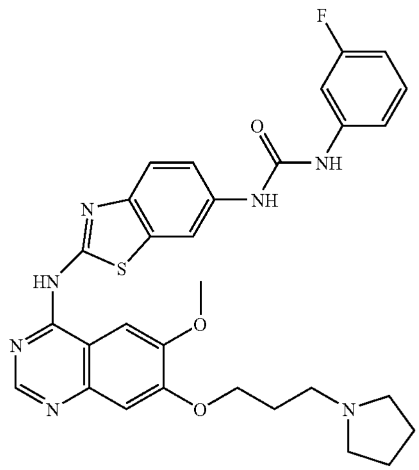 | 588 | 3.25 |

Analytical data of compounds of the present invention of formula (Ia):

| Example | Compound Structure | LC/ESI-MS: [M + H] m/z = | Rt |
|---|---|---|---|
| 25 | 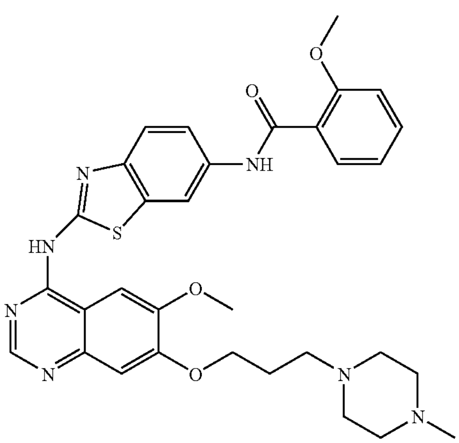 | 614 | 2.85 |
| 26 | 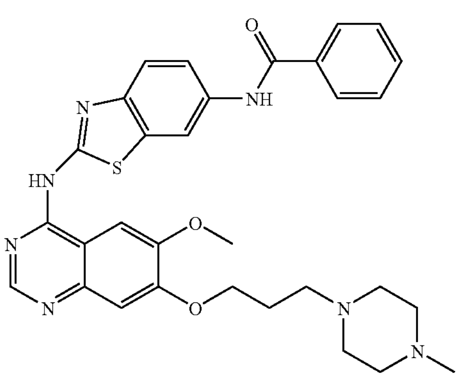 | 584 | 2.73 |

-continued

| Example | Compound Structure | LC/ESI-MS: [M + H] m/z = | Rt |
|---|---|---|---|
| 27 | 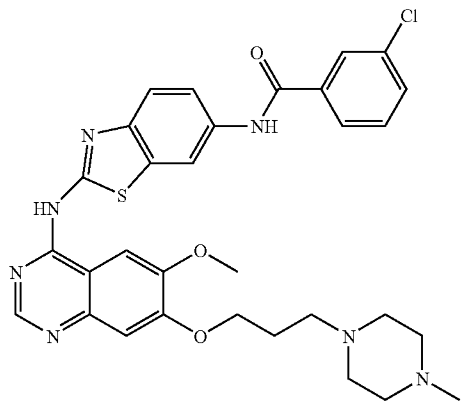 | 618 | 2.79 |
| 28 | 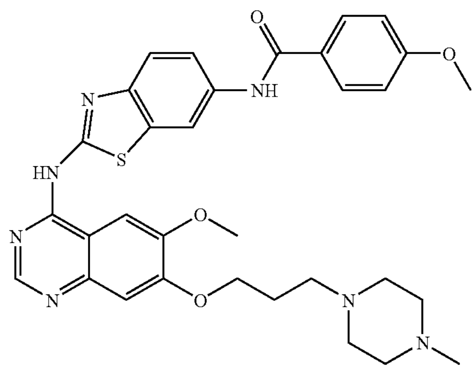 | 614 | 2.63 |
| 29 | 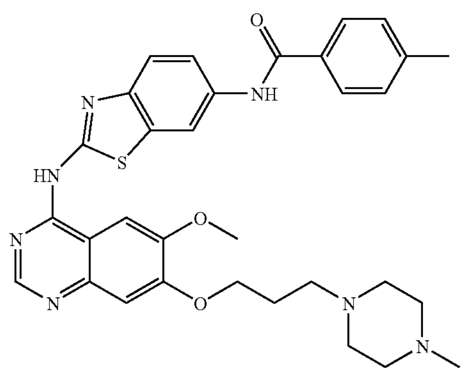 | 598 | 2.72 |
| 59 | 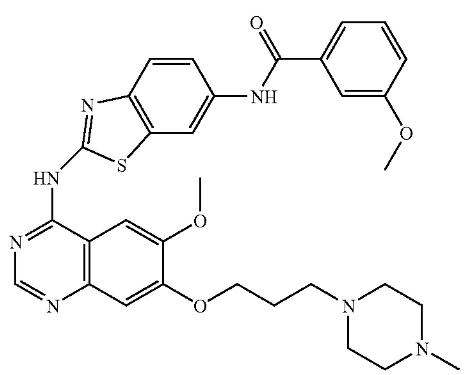 | 614 | 2.77 |

-continued
| Example | Compound Structure | LC/ESI-MS: [M + H] m/z = | Rt |
|---------|-------------------|--------------------------|-----|
| 60 | 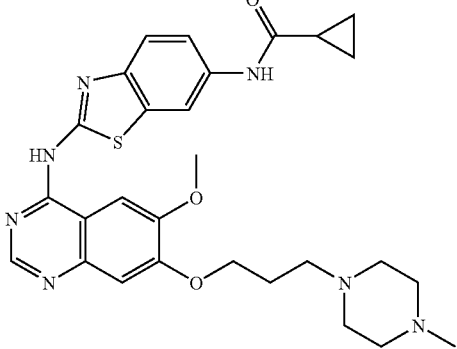 | 548 | 2.40 |
Analytical data of compounds of the present invention of formula (Ib):
| Example | Compound Structure | LC/ESI-MS: [M + H] m/z = | Rt |
|---------|-------------------|--------------------------|-----|
| 1 | 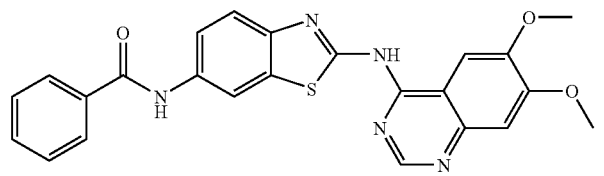 | 458 | 3.05 |
| 2 | 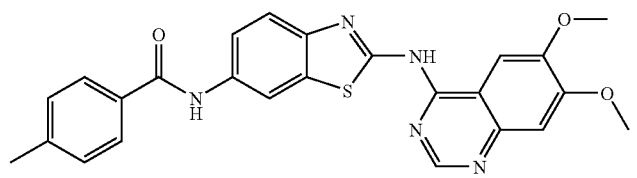 | 472 | 3.30 |
| 3 | 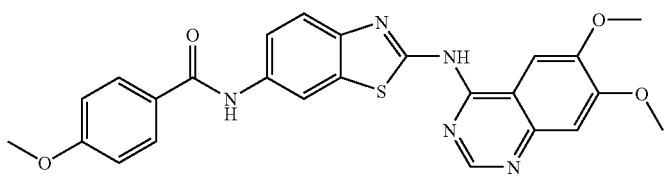 | 488 | 3.10 |
| 4 | 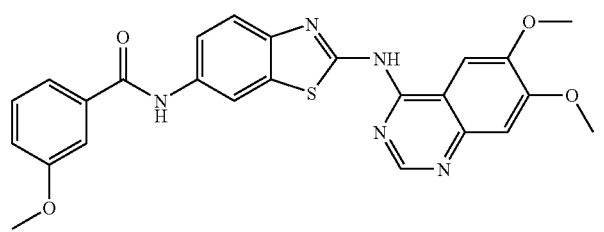 | 488 | 3.15 |

-continued

| Example | Compound Structure | LC/ESI-MS: [M + H] m/z = | Rt |
|---|---|---|---|
| 5 | 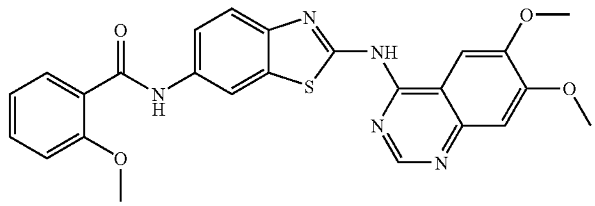 | 488 | 3.25 |
| 6 | 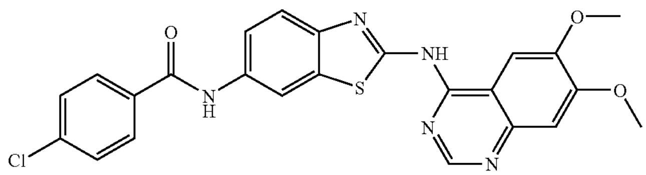 | 492 | 3.47 |
| 7 | 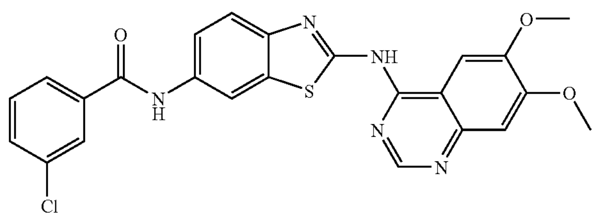 | 492 | 3.43 |
| 8 | 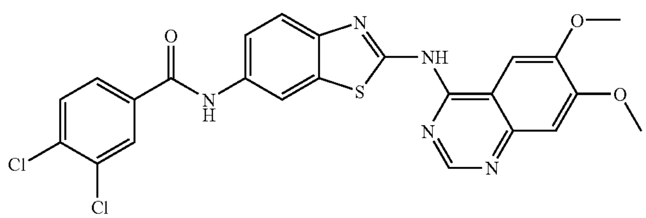 | 526 | 3.77 |
| 9 | 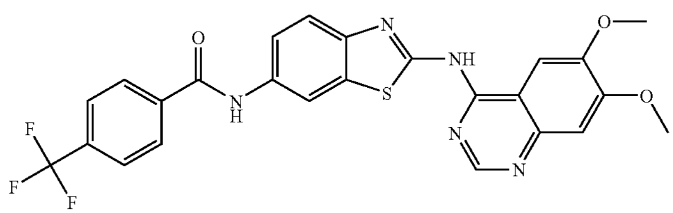 | 526 | 3.65 |
| 10 | 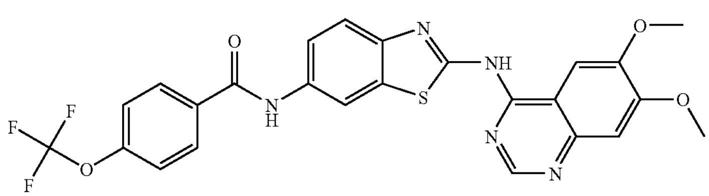 | 542 | 3.87 |
| 11 | 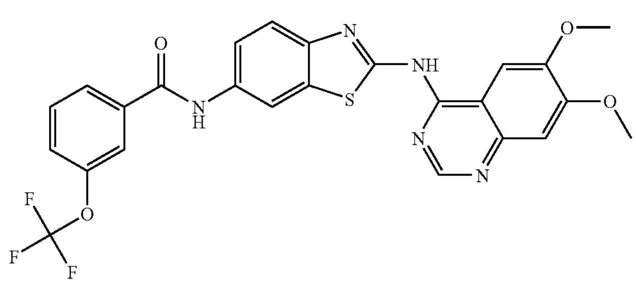 | 542 | 3.85 |

MATERIALS AND METHODS

In Vitro Protein Kinase Assay

The effect of the thiazole derivatives was tested on recombinant, human protein kinases. All protein kinases were expressed in Sf9 insect cells as human recombinant GST-fusion proteins or as His-tagged proteins by means of the baculovirus expression system. Protein kinases were purified by affinity chromatography using either GSH-agarose or Ni-NTH-agarose. The purity and identity of each was checked by SDS-PAGE/silver staining and by western blot analysis with specific antibodies.

A proprietary protein kinase assay ($^{33}$PanQinase® Activity Assay) was used for measuring the kinase activity. All kinase assays were performed in 96-well FlashPlates™ in a 50 µl reaction volume. The assay for all enzymes contained 60 mM HEPES-NaOH, pH 7.5, 3 mM $MgCl_2$, 3 mM $MnCl_2$, 3 µM Na-orthovanadate, 1.2 mM DTT, 50 µg/ml $PEG_{20000}$ and 1 µM [γ-$^{33}$P]-ATP (approx. 5×10$^5$ cpm per well).

The reaction cocktails were incubated at 30° C. for 80 minutes. The reaction was stopped with 50 µl of 2% (v/v) $H_3PO_4$, plates were aspirated and washed two times with 200 µl of 0.9% (w/v) NaCl. Incorporation of $^{33}P_i$ was determined with a microplate scintillation counter. All assays were performed with a BeckmanCoulter/Sagian robotic system.

Cellular Receptor Tyrosine Kinase Assay

The effect of thiazole derivatives was tested in cellular assays by determining the inhibition of the receptor tyrosine kinases (RTKs) of the growth factor receptors EGF-R, PDGF-R, TIE2, IGF-1R, EPHB4, and VEGF-R2. To this end different cell lines expressing the respective growth factor receptor in appropriate amounts were used. 35,000 cells per well were plated in medium containing 10% fetal calf serum (FCS) in 48-well cell culture dishes. After 24 h the FCS-containing medium was exchanged against medium without FCS, and subsequently cells were starved in this medium overnight. On the next day test compounds at different concentrations in 100% DMSO were added to the cell culture medium in a 1:100 dilution step resulting in a final DMSO assay concentration of 1%. After 90 min preincubation with test compounds at 37° C., cells were stimulated at room temperature for several min with receptor-specific ligands. Receptor stimulation was followed by cell lysis using a lysis buffer complemented with standard protease and phosphatase inhibitors.

The phosphorylation status of the various RTKs was quantified in 96-well plates via a sandwich ELISA using receptor-specific capture antibodies and a generic biotinylated anti-phosphotyrosine detection antibody. Finally optical density was measured at 450 nm after addition of avidin-labelled horseradish peroxidase and Tetramethylbenzidine (TMB) as a substrate.

For each particular concentration of a test compound inhibition was calculated percentagewise relative to maximal phosphorylation in stimulated, untreated cells ("high control"). $IC_{50}$ values were calculated based on sigmoidal inhibitor curves covering a concentration range of 9 concentrations of each test compound in half-logarithmic steps.

Cellular Aurora-B Kinase Assay

The effect of thiazole derivatives was tested in a cellular Aurora-B assay by measuring the effect of the test compounds on the endoreduplication of genomic DNA. Inhibition of Aurora-B results in endoreduplication of genomic DNA, which is detectable in cells as DNA-content higher then 4 n. Intercalation of fluorescent Propidium Iodine (PI) into DNA was used to quantify the DNA content by using a fluorescence activated cell sorter (FACS).

HT29 colon-carcinoma cells were seeded on day 1 of the experiment at 100,000 cells per well in 6-well cell culture dishes in 3 ml of DMEM medium containing 10% (v/v) FCS, 100 units/ml Penicillin, 100 mg/ml Streptomycin at 37° C., 10% $CO_2$. On day 2 test compounds at different concentrations in 100% DMSO were added to the medium in a 1:1000 dilution step resulting in a final DMSO assay concentration of 0.1%. Cells were incubated with test compounds for 3 days. On day 5 the cells were harvested by trypsinization, combined with corresponding supernatants, centrifuged, and resuspended in 80% (v/v) methanol for fixation and permeabilization at 4° C. overnight. On day 6 fixed cells were centrifuged, rehydrated in PBS/1% (v/v) FCS for 1 h, and subsequently incubated with RNAse A and PI for 30 min at room temperature.

Stained cells were analyzed for DNA-content by FACS as follows. For analyses of the cell cycle distribution of the cell population, 5000 single-cell-events of the differently treated cells were aquired by FACS. DNA-intercalated PI was detected by measuring fluorescence emission using a 650 nm pass filter (FL3) upon excitation at 488 nm with an argon laser. Single cell events were plotted in a histogram according to their FL3-A signal. Signal amplification for the first peak of the FL-3 amplitude (FL3-A) was set to about 200 arbitrary units (AU). Using an untreated cell population, gates were defined for each of the different cell cycle phases. The area containing the gaussian-curve-shaped first peak at 200 AU was defined as "cells in G1-phase" containing the double set of chromosomes (2n). The area around the peak at 400 AU was defined as "cells in G2/M-phase" containing the quadruple set of chromosomes (4n). Events in between G1 and G2/M was defined as "cells in S-phase", those below G1 (subG1) as "apoptotic". Importantly, all events beyond the G2/M-gate were defined as "endoreduplicated cells" (EndoR). For each concentration of a test compound the percentage of EndoR-population as compared to the whole cell population was determined. For estimation of $IC_{50}$ values of Aurora-B inhibition the percentages of EndoR-populations were plotted versus compound concentrations.

Cellular Aurora-B Kinase Histone H3 Phosphorylation Assay

The effect of compounds was tested in a cellular Aurora-B assay measuring phosphorylation of the Aurora B-substrate protein Histone H3 at Serine 10 (H is H3-pS10). Inhibition of Aurora B results in reduction of H is H3-pS10 which was detected in a specific immuno-assay.

HT-29 colon-carcinoma cells were seeded on day 1 of the experiment at 100,000 cells per well in 48-well cell culture dishes in 500 µL of DMEM medium containing 10% v/v fetal calf serum, 100 units/mL Penicillin and 100 mg/mL Streptomycin. Cells were held at 37° C. and 10% $CO_2$. On day 2 test compounds at different concentrations in 100% DMSO were added in duplicates to the medium in a 1:100 dilution step resulting in a final DMSO assay concentration of 1%. As "low control" representing maximal inhibition, Aurora B-reference inhibitor VX-680 (Vertex) was tested in six replicates at a concentration of 1E-06 M. As "high control", cells were not inhibited but just treated in six replicates with 1% DMSO. Cells were incubated with test compounds for 1 hour. Subsequently, 100 µL of 600 nM phosphatase inhibitor Calyculin A were added yielding a final concentration of 100 nM. After 30 min of further incubation, cells were harvested. For that purpose, dishes were centrifuged at 770×g, 5 min, 4° C., supernatant was aspirated, cells were washed with 500 µL PBS containing 1 mM sodium orthovanadate, and dishes centrifuged again. After aspiration of the supernatants, 100 µL lysis-buffer containing 100 mM sodium-carbonate pH 9.6 with 0.01% Triton X-100, 1 mM sodium-orthovanadate and 100 µM PMSF, were added to each well. The 48-well dish was sealed, incubated for 5 min, heated at 60° C. for 10 min and then sonicated in an ultrasound bath for 2 min. 80 µL of cell lysate from each well were then transferred to a 96-well microtiterplate (MTP, Nunc F96 Maxisorb, Cat.# 442404).

Upon binding of lysate proteins for at least 2.5 hours at 37° C., lysates were discarded and the MTP coated with 5% bovine serum albumin in DELFIA®D-assay buffer (Perkin Elmer, Cat.# 4002-0010). Upon 3fold washing with DELFIA®-wash buffer (Perkin Elmer, Cat.# 1244-114), 100 µl of the detecting antibody directed against H is H3-pS10 (rabbit monoclonal antibody clone MC463; Upstate, Cat.# 05-817) were added in a dilution of 1:400 in DELFIA®-assay buffer. After 1 h incubation at 37 C. and 3fold washing, 100 µL of Europium-labeled secondary anti-rabbit-IgG-antibody (Perkin Elmer, Cat.# AD0105) at a concentration of 5 nM in DELFIA®-assay buffer were added. Upon 30 min incubation at 37° C. and 3fold washing, 150 µL DELFIA®-enhancer solution (Perkin-Elmer, Cat.# 1244-105) were added and the emission at 615 nm in each single well was measured in a fluorometer using time-resolved fluorometry with excitation at 340 nm. For data analysis, the average emission of the six "low control" replicates was determined and subtracted from all measurements. Values were then transformed into percentage, based on the mean of "low control"-replicates representing 0% and of "high control"-replicates representing 100% of measurable phosphorylation of HisH3 at Serine 10. The duplicate values of each compound concentration were then averaged, and these mean values of H is H3-pS10 percentage were plotted versus the compound concentration for calculation of $IC_{50}$-values.

RESULTS

In Vitro Protein Kinase Assay

The compounds of the present invention show $IC_{50}$ values lower than 500 nM on at least one kinase selected from Aurora-A, Aurora-B, EGF-R, ERBB2, PDGFR, FLT3, IGF1-R, VEGF-R2, VEGF-R3, EPHB4, TIE2, FAK, and SRC or display a beneficial activity profile by inhibiting at least two kinases from at least two different molecular mechanisms of tumor progression with $IC_{50}$ values lower than 500 nM.

The compounds of the present invention show $IC_{50}$ values lower than 10 µM in the Cellular Receptor Tyrosine Kinase Assay and/or the Cellular Aurora-B Kinase Assay.

The invention claimed is:

1. A compound of the general formula (I), or a pharmaceutically acceptable salt thereof,

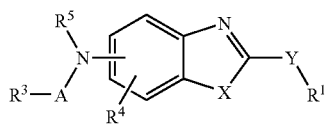

formula (I)

wherein the substituent

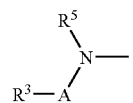

is attached to the 5- or 6-position of the benzazole;

X independently represents S, SO, or $SO_2$;
Y independently represents S, O, $NR^2$, SO, or $SO_2$;
A independently represents ←$CONR^8$—, ←$NR^8CO$—, ←$NR^8CONR^9$—, ←$NR^8COO$—, ←$NR^8NR^9CO$—, ←$NR^8OCO$—, ←$ONR^8CO$—, or ←$NR^8SO_2$—, where ← indicates the point of attachment to $R^3$;

$R^2$ independently represents H, alkyl, cycloalkyl, —$COR^6$, —$SOR^6$, —$SO_2R'$, —CN, hydroxyalkyl, haloalkyl, haloalkyloxy, or alkylamino;

$R^3$ independently represents H, alkyl, cycloalkyl, aryl, or heteroaryl;

$R^4$ represents H, —$COR^6$, —$CO_2R^6$, —$SOR^6$, —$SO_2R^6$, —$SO_3R^6$, —$NO_2$, —CN, —$CF_3$, —$OCH_3$, —$OCF_3$, alkyl, cycloalkyl, alkoxy, —$NH_2$, alkylamino, —$NR^7COR^6$, halogen, —OH, —SH, alkylthio, haloalkyl, haloalkyloxy, aryl or heteroaryl;

$R^5$ independently represents H, alkyl, cycloalkyl, —$COR^6$, —$SOR^6$, —$SO_2R^6$, —CN, hydroxyalkyl, haloalkyl, haloalkyloxy, alkylamino, aryl, or heteroaryl;

$R^6$ independently represents H, alkyl, cycloalkyl, —$NR^8R^9$, —$NR^2NR^8R^9$, —$ONR^8R^9$, —$NR^8OR^9$, aryl or heteroaryl;

$R^7$ independently represents H, alkyl, cycloalkyl, or alkoxy;

$R^8$ independently represents H, alkyl, cycloalkyl, —$COR^6$, —$SOR^6$, —$SO_2R^6$, haloalkyl, haloalkyloxy, aryl or heteroaryl;

$R^9$ independently represents H, alkyl, cycloalkyl, —$COR^6$, —$SOR^6$, —$SO_2R^6$, hydroxyalkyl, haloalkyl, haloalkyloxy, aryl or heteroaryl;

$R^1$ independently represents one of the following groups:

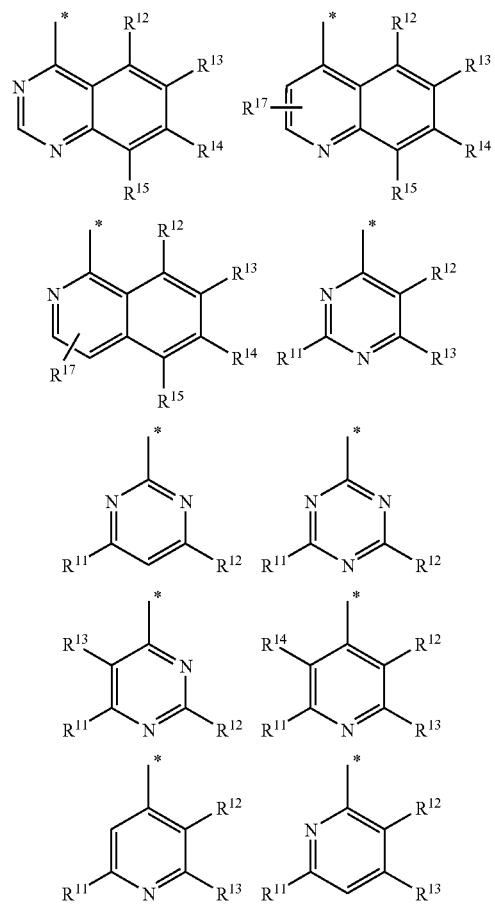

-continued

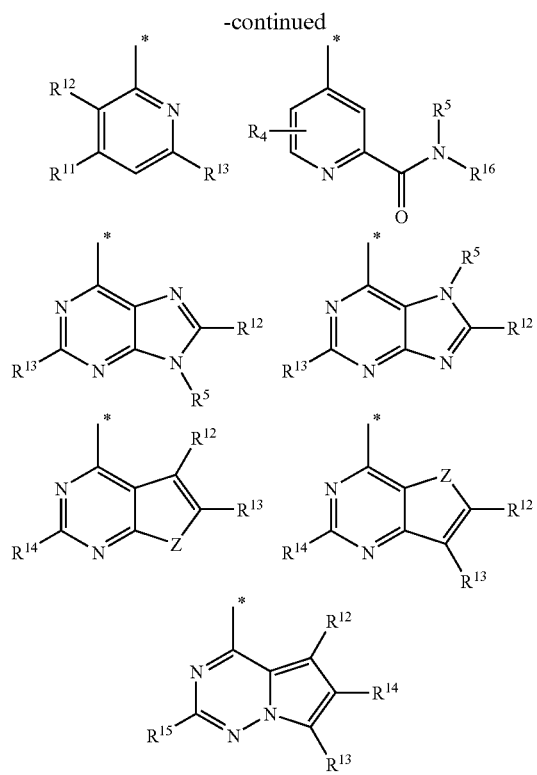

where * indicates the point of attachment
Z independently represents O, NR⁸, or S;
R¹¹ independently represents H, —NHR⁸, or one of the groups:

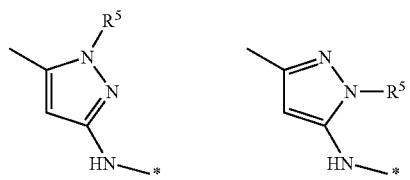

where * indicates the point of attachment;
R¹² independently represents H, halogen, nitro, trifluoromethyl, alkyl, aryl, heteroaryl, —NR⁸R⁹, or —X²R¹⁶;
R¹³ independently represents H, halogen, nitro, trifluoromethyl, alkyl, aryl, heteroaryl, —NR⁸R⁹, or —X²R¹⁶;
R¹⁴ independently represents H, halogen, nitro, trifluoromethyl, alkyl, aryl, heteroaryl, —NR⁸R⁹, or —X²R¹⁶;
R¹⁵ independently represents H, halogen, nitro, trifluoromethyl, alkyl, aryl, heteroaryl, —NR⁸R⁹, or —X²R¹⁶;
R¹⁷ independently represents H, halogen, nitro, trifluoromethyl, alkyl, aryl, heteroaryl, —NR⁸R⁹, or —X²R¹⁶;
X² independently represents a direct bond, —O—, —CH₂—, —OCO—, carbonyl, —S—, —SO—, —SO₂—, —NR⁸CO—, —CONR⁸—, SO₂NR⁸—, —NR⁸SO₂— or —NR⁸—;
R¹⁶ independently represents H, alkyl, cycloalkyl, —COR⁶, —SOR⁶, —SO₂R⁶, —OCH₃, —OCF₃, haloalkyl, haloalkyloxy, or one of the following groups:

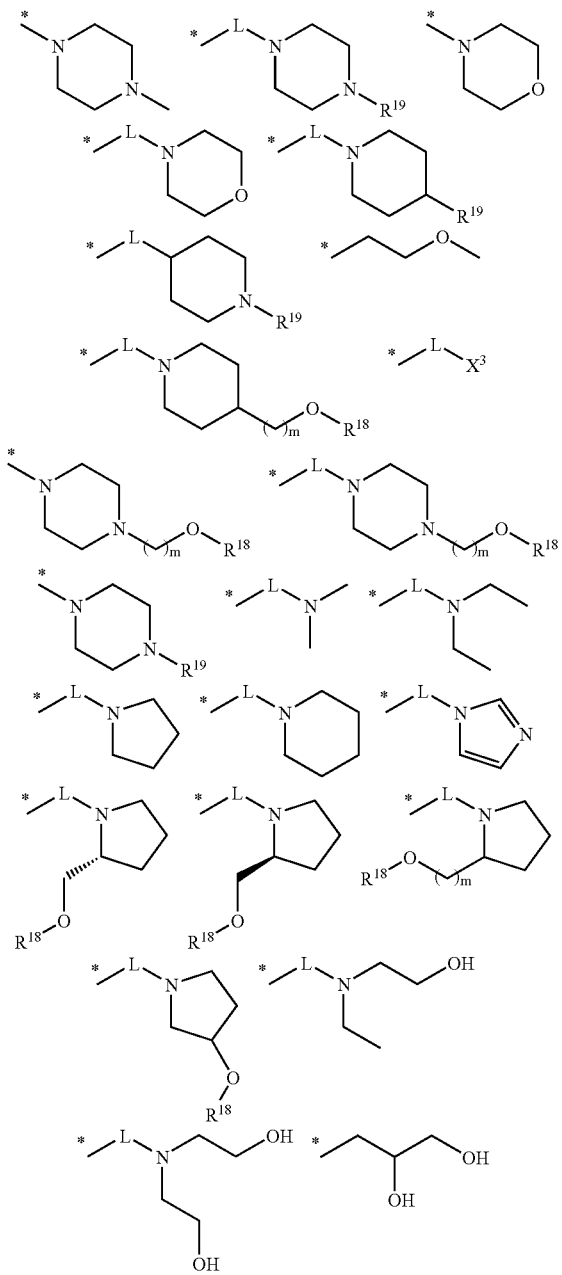

where * indicates the point of attachment
m independently represents an integer from 1-3;
L is absent or represents a divalent linkage group selected from alkylen, cycloalkylen, heterocyclylen, arylen, or heteroarylen, wherein one or more of the (—CH₂—) groups may be replaced by an oxygen or a NR⁸, and wherein one or more carbon atoms may be independently substituted by one or two substituents selected from halogen, hydroxy, alkoxy, haloalkyloxy, phoshonooxy, or phoshonooxyalkyl;
X³ independently represents —COOH, —COOalkyl, —CONR⁸R⁹, —OH, —NR⁸R⁹, —SH, —SO₃H, —SO₂NR⁸R⁹, alkyloxy, haloalkyloxy, or alkylamino;
R¹⁸ independently represents H, phosphonooxy, or phosphonooxy-alkyl;

$R^{19}$ independently represents H, alkyl, cycloalkyl, alkylamino, or alkoxy;

wherein an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkynyl group, which can be substituted by one or more substituents R';

wherein R' independently represents H, —CO$_2$R", —CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

wherein R" independently represents H, haloalkyl, hydroxyalkyl, alkyl, cycloalkyl, aryl, heteroaryl or aminoalkyl;

wherein a cycloalkyl group denotes a non-aromatic ring system containing three to eight carbon atoms, preferably four to eight carbon atoms, wherein one or more of the carbon atoms in the ring can be substituted by a group E, E being O, S, SO, SO$_2$, N, or NR", R" being as defined above;

wherein an alkoxy group denotes an O-alkyl group, the alkyl group being as defined above; the alkoxy group is preferably a methoxy, ethoxy, isopropoxy, t-butoxy or pentoxy group;

wherein an alkylthio group denotes an S-alkyl group, the alkyl group being as defined above;

wherein a haloalkyl group denotes an alkyl group which is substituted by one to five halogen atoms, the alkyl group being as defined above;

wherein a hydroxyalkyl group denotes an HO-alkyl group, the alkyl group being as defined above;

wherein a haloalkyloxy group denotes an alkoxy group which is substituted by one to five halogen atoms, the alkyl group being as defined above;

wherein a hydroxyalkylamino group denotes an (HO-alkyl)$_2$-N— group or HO-alkyl-NH— group, the alkyl group being as defined above;

wherein an alkylamino group denotes an HN-alkyl or N-dialkyl group, the alkyl group being as defined above;

wherein a halogen group is chlorine, bromine, fluorine or iodine;

wherein an aryl group denotes an aromatic group having five to fifteen carbon atoms, which can be substituted by one or more substituents R', where R' is as defined above;

wherein a heteroaryl group denotes a 5- or 6-membered heterocyclic group which contains at least one heteroatom like O, N, S, wherein the heterocyclic group can be fused to another ring and wherein the heterocyclic group can be substituted by one or more substituents R', wherein R' is as defined above;

wherein an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

wherein a cycloalkylene group denotes a divalent non-aromatic ring system containing three to eight carbon atoms, preferably four to eight carbon atoms, wherein one or more of the carbon atoms in the ring may be substituted by a group E, E being O, S, SO, SO$_2$, N, or NR", R" being as defined above;

wherein a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

wherein an arylene group denotes an aromatic divalent group having five to fifteen carbon atoms, which may be substituted by one or more substituents R', and may be fused to another aromatic ring, where R' is as defined above;

wherein a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

wherein a phosphonooxy group is —O—P(=O)(OH)$_2$ or a salt thereof;

wherein a phosphonooxyalkyl group denotes an -alkyl-O—P(=O)(OH)$_2$ group or a salt thereof, alkyl being as defined above.

2. A compound of the general formula (Ia), or a pharmaceutically acceptable salt thereof, formula (Ia)

$$R^3-A-N(R^5)-\text{[benzazole]}-X-Y-R^1 \quad (R^4)$$

wherein the substituent $$R^3-A-N(R^5)-$$

is attached to the 5- or 6-position of the benzazole;

X independently represents S, SO, or SO$_2$;

Y independently represents S, O, NR$^2$, SO, or SO$_2$;

A independently represents ←CO—, ←CS—, ←SO—, SO$_2$—, or ←CO$_2$—, where ← indicates the point of attachment to R$^3$;

R$^2$ independently represents H, alkyl, cycloalkyl, —COR$^6$, —SOR$^6$, —SO$_2$R$^6$, —CN, hydroxyalkyl, haloalkyl, haloalkyloxy, or alkylamino;

R$^3$ independently represents H, alkyl, cycloalkyl, aryl, or heteroaryl;

R$^4$ represents H, —COR$^6$, —CO$_2$R$^6$, —SOR$^6$, —SO$_2$R$^6$, —SO$_3$R$^6$, —NO$_2$, —CN, —CF$_3$, —OCH$_3$, —OCF$_3$, alkyl, cycloalkyl, alkoxy, —NH$_2$, alkylamino, —NR$^7$COR$^6$, halogen, —OH, —SH, alkylthio, haloalkyl, haloalkyloxy, aryl or heteroaryl;

R$^5$ independently represents H, alkyl, cycloalkyl, —COR$^6$, —SOR$^6$, —SO$_2$R$^6$, —CN, hydroxyalkyl, haloalkyl, haloalkyloxy, alkylamino, aryl, or heteroaryl;

R$^6$ independently represents H, cycloalkyl, —NR$^8$R$^9$, —NR$^2$NR$^8$R$^9$, —ONR$^8$R$^9$, —NR$^8$OR$^9$, aryl or heteroaryl;

R[7] independently represents H, alkyl, cycloalkyl, or alkoxy;

R[8] independently represents H, alkyl, cycloalkyl, —COR[6], —SOR[6], —SO$_2$R[6], haloalkyl, haloalkyloxy, aryl or heteroaryl;

R[9] independently represents H, alkyl, cycloalkyl, —COR[6], —SOR[6], —SO$_2$R[6], hydroxyalkyl, haloalkyl, haloalkyloxy, aryl or heteroaryl;

R[1] independently represents one of the following groups:

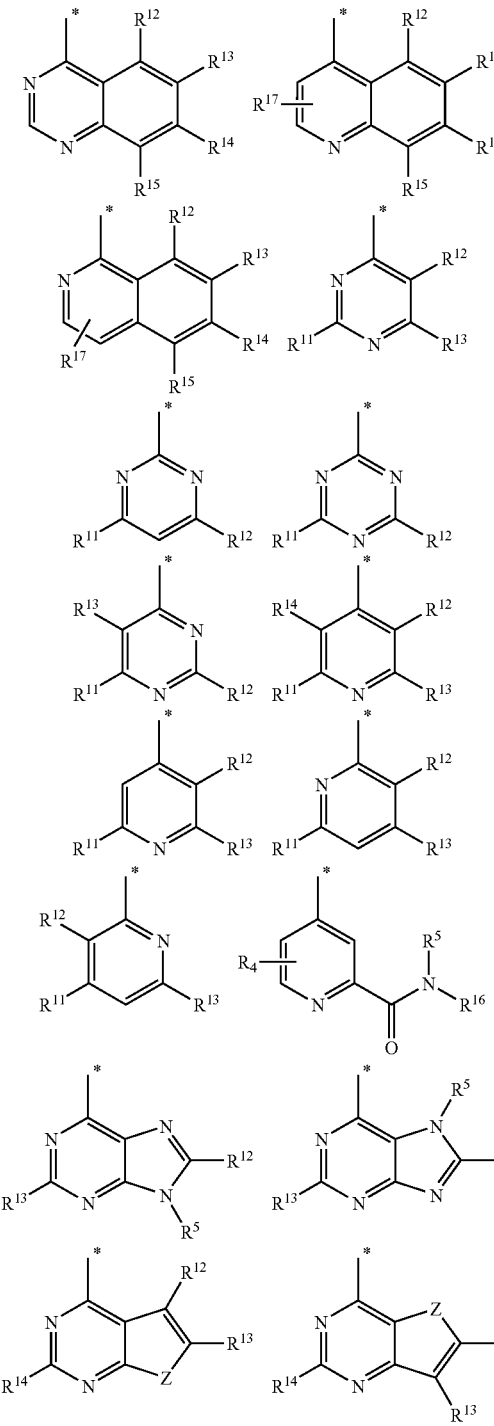

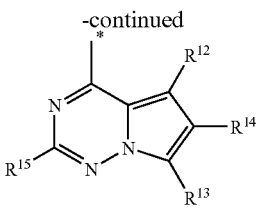

where * indicates the point of attachment

Z independently represents O, NR[8], or S;

R[11] independently represents H, —NHR[8], or one of the groups:

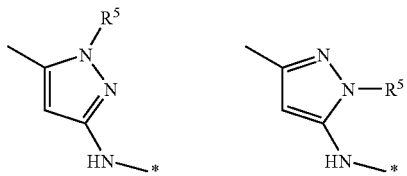

where * indicates the point of attachment;

R[12] independently represents H, halogen, nitro, trifluoromethyl, alkyl, aryl, heteroaryl, —NR[8]R[9], or —X$^2$R[16];

R[13] independently represents H, halogen, nitro, trifluoromethyl, alkyl, aryl, heteroaryl, —NR[8]R[9], or —X$^2$R[16];

R[13a] independently represents nitro, aryl, heteroaryl, —NR[8]R[9], or —X$^2$R[16a];

R[14a] independently represents nitro, aryl, heteroaryl, —NR[8]R[9], or —X$^2$R[16a];

R[14] independently represents H, halogen, nitro, trifluoromethyl, alkyl, aryl, heteroaryl, —NR[8]R[9], or —X$^2$R[16a];

R[15] independently represents H, halogen, nitro, trifluoromethyl, alkyl, aryl, heteroaryl, —NR[8]R[9], or —X$^2$R[16a];

R[17] independently represents H, halogen, nitro, trifluoromethyl, alkyl, aryl, heteroaryl, —NR[8]R[9], or —X$^2$R[16];

X$^2$ independently represents a direct bond, —O—, —CH$_2$—, —OCO—, carbonyl, —S—, —SO—, —SO$_2$—, —NR[8]CO—, —CONR[8]—, —SO$_2$NR[8]—, —NR[8]SO$_2$— or —NR[8]—;

R[16] independently represents H, alkyl cycloalkyl, —COR[6]—, —SOR[6], —SO$_2$R[6], —OCH$_3$, —OCF$_3$, haloalkyl, haloalkyloxy, or one of the following groups:

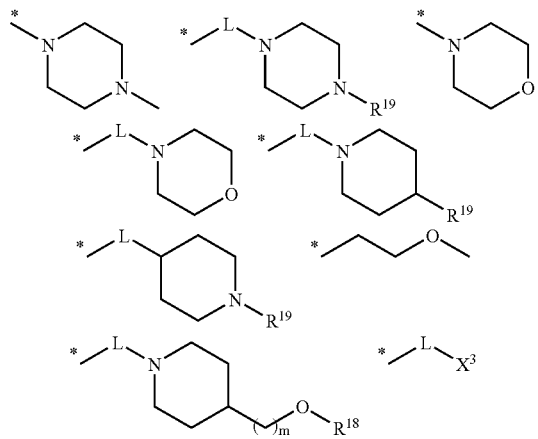

-continued

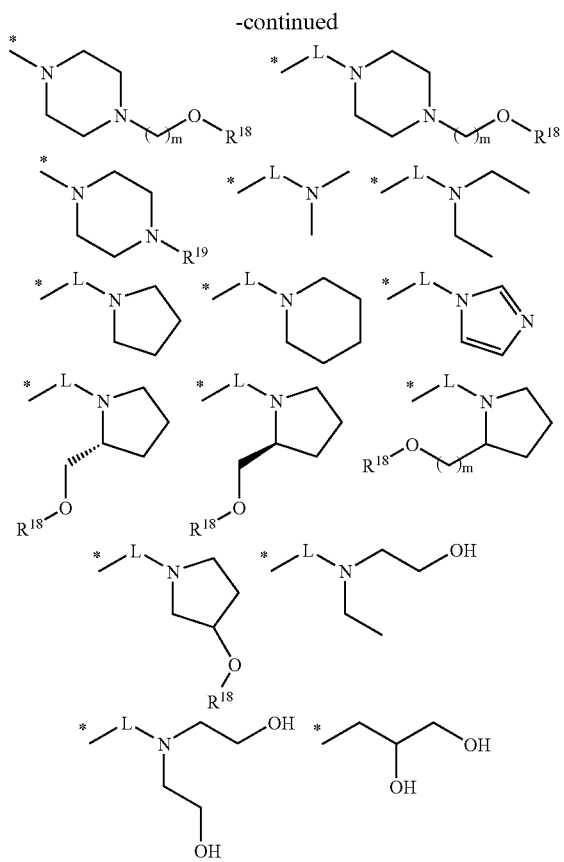

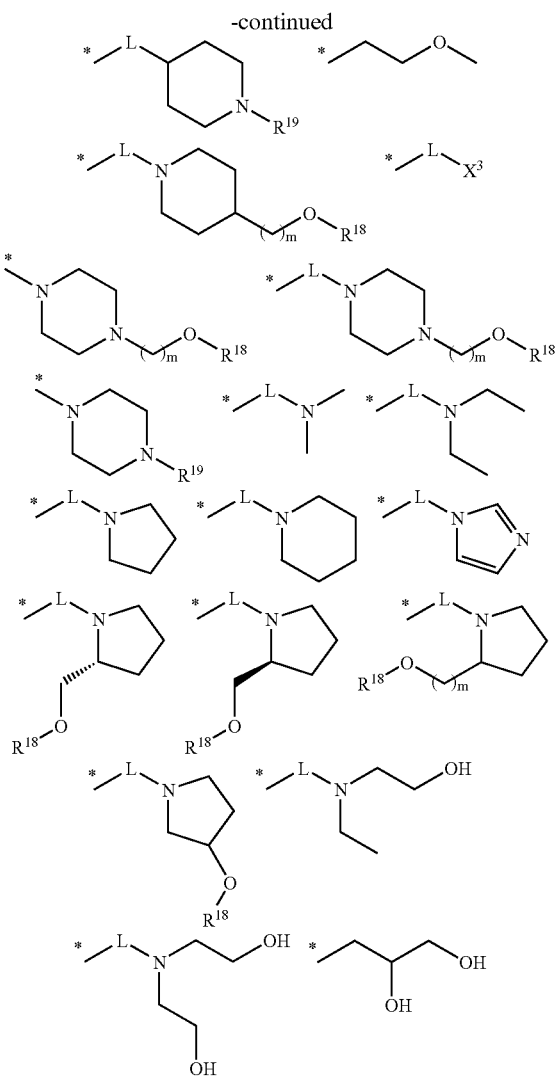

where * indicates the point of attachment
m independently represents an integer from 1-3;
L is absent or represents a divalent linkage group selected from alkylen, cycloalkylen, heterocyclylen, arylen, or heteroarylen, wherein one or more of the (—$CH_2$—) groups may be replaced by an oxygen or a $NR^8$, and wherein one or more carbon atoms may be independently substituted by one or two substituents selected from halogen, hydroxy, alkoxy, haloalkyloxy, phoshonooxy, or phoshonooxyalkyl;
$X^3$ independently represents —COOH, —COOalkyl, —$CONR^8R^9$, —OH, —SH, —$NR^8R^9$, —$SO_3H$, —$SO_2NR^8R^9$, alkyloxy, haloalkyloxy, or alkylamino;
$R^{18}$ independently represents H, phosphonooxy, or phosphonooxy-alkyl;
$R^{19}$ independently represents H, alkyl, cycloalkyl, alkylamino, or alkoxy;
$R^{16a}$ independently represents one of the following groups:

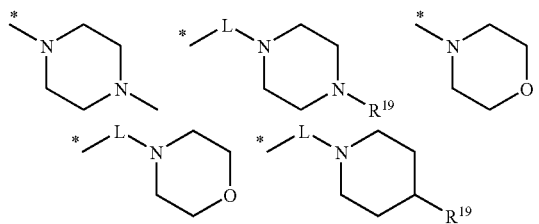

where * indicates the point of attachment
wherein an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkynyl group, which can be substituted by one or more substituents R';
wherein R' independently represents H, —$CO_2R''$, —CONHR'', —CR''O, —$SO_2NR''$, —NR''—CO-haloalkyl, —$NO_2$, —NR''—$SO_2$-haloalkyl, —NR''—$SO_2$-alkyl, —$SO_2$-alkyl, —NR''—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
wherein R'' independently represents H, haloalkyl, hydroxyalkyl, alkyl, cycloalkyl, aryl, heteroaryl or aminoalkyl;
wherein a cycloalkyl group denotes a non-aromatic ring system containing three to eight carbon atoms, preferably four to eight carbon atoms, wherein one or more of the carbon atoms in the ring can be substituted by a group E, E being O, S, SO, $SO_2$, N, or NR'', R'' being as defined above;

wherein an alkoxy group denotes an O-alkyl group, the alkyl group being as defined above; the alkoxy group is preferably a methoxy, ethoxy, isopropoxy, t-butoxy or pentoxy group;

wherein an alkylthio group denotes an S-alkyl group, the alkyl group being as defined above;

wherein a haloalkyl group denotes an alkyl group which is substituted by one to five halogen atoms, the alkyl group being as defined above;

wherein a hydroxyalkyl group denotes an HO-alkyl group, the alkyl group being as defined above;

wherein a haloalkyloxy group denotes an alkoxy group which is substituted by one to five halogen atoms, the alkyl group being as defined above;

wherein a hydroxyalkylamino group denotes an (HO-alkyl)$_2$-N— group or HO-alkyl-NH— group, the alkyl group being as defined above;

wherein an alkylamino group denotes an HN-alkyl or N-dialkyl group, the alkyl group being as defined above;

wherein a halogen group is chlorine, bromine, fluorine or iodine;

wherein an aryl group denotes an aromatic group having five to fifteen carbon atoms, which can be substituted by one or more substituents R', where R' is as defined above;

wherein a heteroaryl group denotes a 5- or 6-membered heterocyclic group which contains at least one heteroatom like O, N, S, wherein the heterocyclic group can be fused to another ring and wherein the heterocyclic group can be substituted by one or more substituents R', wherein R' is as defined above;

wherein an alkylene group denotes a divalent linear or branched $C_1$-$C_6$-alkylene, preferably a linear or branched chain of one to five carbon atoms, a linear or branched $C_2$-$C_6$-alkenylene or a linear or branched $C_2$-$C_6$-alkynylene group, which may be substituted by one or more substituents R';

wherein a cycloalkylene group denotes a divalent non-aromatic ring system containing three to eight carbon atoms, preferably four to eight carbon atoms, wherein one or more of the carbon atoms in the ring may be substituted by a group E, E being O, S, SO, SO$_2$, N, or NR", R" being as defined above;

wherein a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;

wherein an arylene group denotes an aromatic divalent group having five to fifteen carbon atoms, which may be substituted by one or more substituents R', and may be fused to another aromatic ring, where R' is as defined above;

wherein a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;

wherein a phosphonooxy group is —O—P(=O)(OH)$_2$ or a salt thereof;

wherein a phosphonooxyalkyl group denotes an -alkyl-O—P(=O)(OH)$_2$ group or a salt thereof, alkyl being as defined above.

3. A compound of the general formula (Ib), or a pharmaceutically acceptable salt thereof,

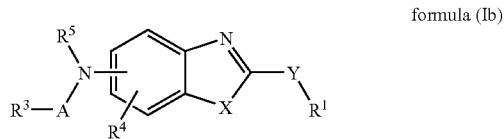

formula (Ib)

wherein the substituent

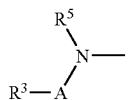

is attached to the 5- or 6-position of the benzazole;

X independently represents S, SO, or SO$_2$;

Y independently represents S, O, NR$^2$, SO, or SO$_2$;

A independently represents ←CO, ←CS—, ←SO—, ←SO$_2$—, or ←CO$_2$—, where ← indicates the point of attachment to R$^3$;

R$^2$ independently represents H, alkyl, cycloalkyl, —COR$^6$, —SOR$^6$, —SO$_2$R$^6$, —CN, hydroxyalkyl, haloalkyl, haloalkyloxy, or alkylamino;

R$^3$ independently represents aryl, or heteroaryl;

R$^4$ independently represents H, —COR$^6$, —CO$_2$R$^6$, —SOR$^6$, —SO$_2$R$^6$, —SO$_3$R$^6$, —NO$_2$, —CN, —CF$_3$, —OCH$_3$, —OCF$_3$, alkyl, cycloalkyl, alkoxy, —NH$_2$, alkylamino, —NR$^7$COR$^6$, halogen, —OH, —SH, alkylthio, haloalkyl, haloalkyloxy, aryl or heteroaryl;

R$^5$ independently represents H, alkyl, cycloalkyl, —COR$^6$, —SOR$^6$, —SO$_2$R$^6$, —CN, hydroxyalkyl, haloalkyl, haloalkyloxy, alkylamino, aryl, or heteroaryl;

R$^6$ independently represents H, alkyl, cycloalkyl, —NR$^8$R$^9$, —NR$^2$NR$^8$R$^9$, —ONR$^8$R$^9$, —NR$^8$OR$^9$, aryl or heteroaryl;

R$^7$ independently represents H, alkyl, cycloalkyl, or alkoxy;

R$^8$ independently represents H, alkyl, cycloalkyl, —COR$^6$, —SOR$^6$, —SO$_2$R$^6$, haloalkyl, haloalkyloxy, aryl or heteroaryl;

R$^9$ independently represents H, alkyl, cycloalkyl, —COR$^6$, —SOR$^6$, —SO$_2$R$^6$, hydroxyalkyl, haloalkyl, haloalkyloxy, aryl or heteroaryl;

R$^1$ independently represents one of the following groups:

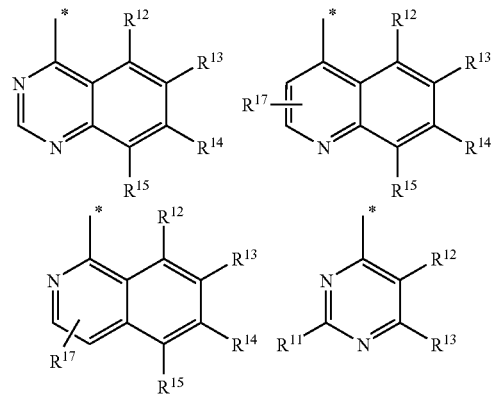

-continued

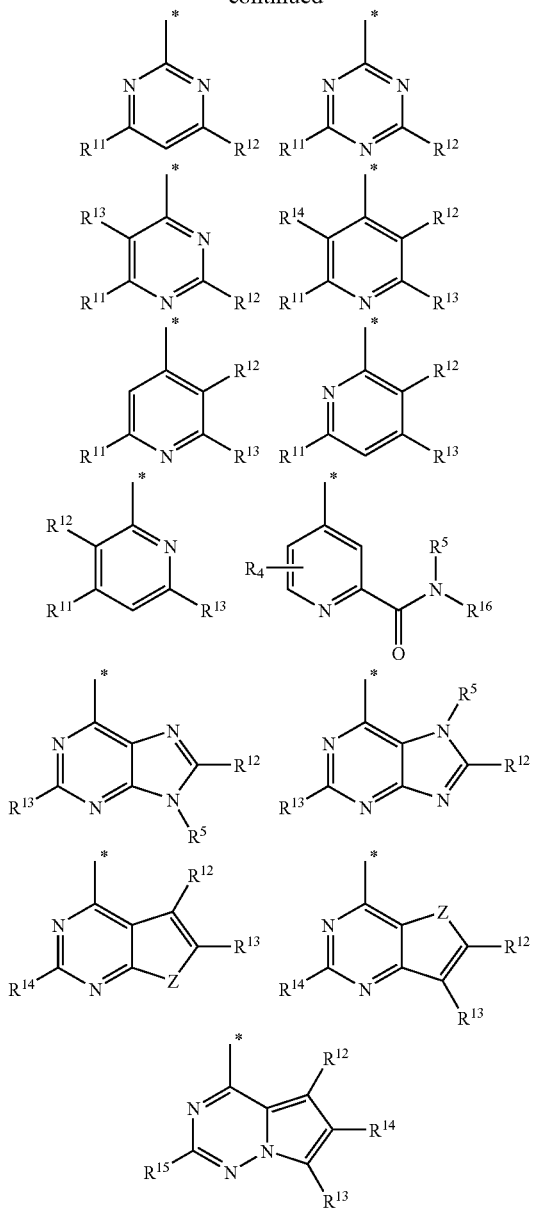

where * indicates the point of attachment
Z independently represents O, NR$^8$, or S;
R$^{11}$ independently represents H, —NHR$^8$, or one of the groups:

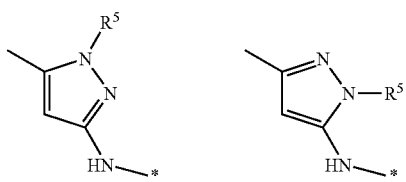

where * indicates the point of attachment;
R$^{12}$ independently represents H, halogen, nitro, trifluoromethyl, alkyl, aryl, heteroaryl, —NR$^8$R$^9$, or —X$^2$R$^{16}$;

R$^{13}$ independently represents H, halogen, nitro, trifluoromethyl, alkyl, aryl, heteroaryl, —NR$^8$R$^9$, or —X$^2$R$^{16}$;

R$^{14}$ independently represents H, halogen, nitro, trifluoromethyl, alkyl, aryl, heteroaryl, —NR$^8$R$^9$, or —X$^2$R$^{16}$;

R$^{13b}$ independently represents H, halogen, haloalkyloxy, alkyl, or alkoxy;

R$^{14b}$ independently represents H, halogen, haloalkyloxy, alkyl, or alkoxy;

R$^{15}$ independently represents H, halogen, nitro, trifluoromethyl, alkyl, aryl, heteroaryl, —NR$^8$R$^9$, or —X$^2$R$^{16}$;

R$^{17}$ independently represents H, halogen, nitro, trifluoromethyl, alkyl, aryl, heteroaryl, —NR$^8$R$^9$, or —X$^2$R$^{16}$;

X$^2$ independently represents a direct bond, —O—, —CH$_2$—, —OCO—, carbonyl, —S—, —SO—, —SO$_2$—, —NR$^8$CO—, —CONR$^8$—, —SO$_2$NR$^8$—, —NR$^8$SO$_2$— or —NR$^8$—;

R$^{16}$ independently represents H, alkyl, cycloalkyl, —COR$^6$, —SOR$^6$, —SO$_2$R$^6$, —OCH$_3$, —OCF$_3$, haloalkyl, haloalkyloxy, or one of the following groups:

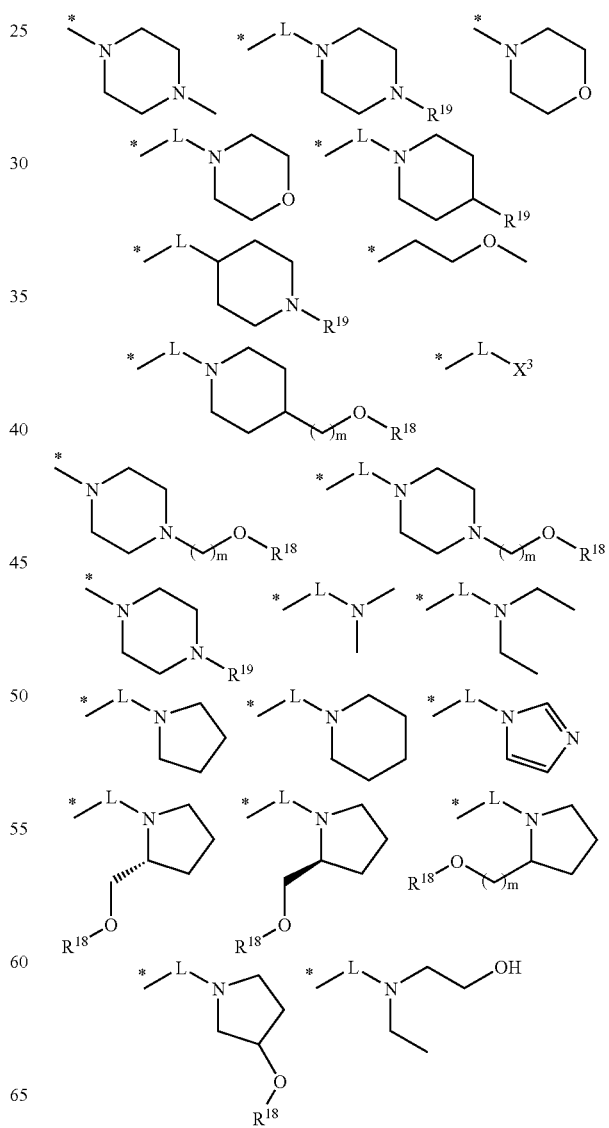

-continued

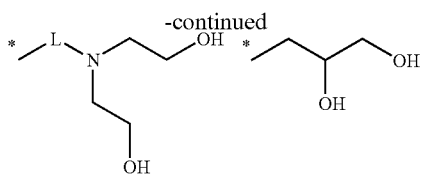

where * indicates the point of attachment
m independently represents an integer from 1-3;
L is absent or represents a divalent linkage group selected from alkylen, cycloalkylen, heterocyclylen, arylen, or heteroarylen, wherein one or more of the (—CH$_2$—) groups may be replaced by an oxygen or a NR$^8$, and wherein one or more carbon atoms may be independently substituted by one or two substituents selected from halogen, hydroxy, alkoxy, haloalkyloxy, phoshonooxy, or phoshonooxyalkyl;
X$^3$ independently represents —COOH, —COOalkyl, —CONR$^8$R$^9$, —OH, —SH, —NR$^8$R$^9$, —SO$_3$H, —SO$_2$NR$^8$R$^9$, alkyloxy, haloalkyloxy, or alkylamino;
R$^{18}$ independently represents H, phosphonooxy, or phosphonooxy-alkyl;
R$^{19}$ independently represents H, alkyl, cycloalkyl, alkylamino, or alkoxy;
wherein an alkyl group, if not stated otherwise, denotes a linear or branched C$_1$-C$_6$-alkyl, preferably a linear or branched chain of one to five carbon atoms, a linear or branched C$_2$-C$_6$-alkenyl or a linear or branched C$_2$-C$_6$-alkynyl group, which can be substituted by one or more substituents R';
wherein R' independently represents H, —CO$_2$R", —CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
wherein R" independently represents H, haloalkyl, hydroxyalkyl, alkyl, cycloalkyl, aryl, heteroaryl or aminoalkyl;
wherein a cycloalkyl group denotes a non-aromatic ring system containing three to eight carbon atoms, preferably four to eight carbon atoms, wherein one or more of the carbon atoms in the ring can be substituted by a group E, E being O, S, SO, SO$_2$, N, or NR", R" being as defined above;
wherein an alkoxy group denotes an O-alkyl group, the alkyl group being as defined above; the alkoxy group is preferably a methoxy, ethoxy, isopropoxy, t-butoxy or pentoxy group;
wherein an alkylthio group denotes an S-alkyl group, the alkyl group being as defined above;
wherein a haloalkyl group denotes an alkyl group which is substituted by one to five halogen atoms, the alkyl group being as defined above;
wherein a hydroxyalkyl group denotes an HO-alkyl group, the alkyl group being as defined above;
wherein a haloalkyloxy group denotes an alkoxy group which is substituted by one to five halogen atoms, the alkyl group being as defined above;
wherein a hydroxyalkylamino group denotes an (HO-alkyl)$_2$-N— group or HO-alkyl-NH— group, the alkyl group being as defined above;
wherein an alkylamino group denotes an HN-alkyl or N-di-alkyl group, the alkyl group being as defined above;
wherein a halogen group is chlorine, bromine, fluorine or iodine;
wherein an aryl group denotes an aromatic group having five to fifteen carbon atoms, which can be substituted by one or more substituents R', where R' is as defined above;
wherein a heteroaryl group denotes a 5- or 6-membered heterocyclic group which contains at least one heteroatom like O, N, S, wherein the heterocyclic group can be fused to another ring and wherein the heterocyclic group can be substituted by one or more substituents R', wherein R' is as defined above;
wherein an alkylene group denotes a divalent linear or branched C$_1$-C$_6$-alkylene, preferably a linear or branched chain of one to five carbon atoms, a linear or branched C$_2$-C$_6$-alkenylene or a linear or branched C$_2$-C$_6$-alkynylene group, which may be substituted by one or more substituents R';
wherein a cycloalkylene group denotes a divalent non-aromatic ring system containing three to eight carbon atoms, preferably four to eight carbon atoms, wherein one or more of the carbon atoms in the ring may be substituted by a group E, E being O, S, SO, SO$_2$, N, or NR", R" being as defined above;
wherein a heterocyclylene group denotes a 3 to 8-membered divalent heterocyclic non-aromatic group which contains at least one heteroatom selected from O, N, and S, wherein the heterocyclylene group may be fused to another non-aromatic ring and may be substituted by one or more substituents R', wherein R' is as defined above;
wherein an arylene group denotes an aromatic divalent group having five to fifteen carbon atoms, which may be substituted by one or more substituents R', and may be fused to another aromatic ring, where R' is as defined above;
wherein a heteroarylene group denotes a divalent 5- or 6-membered heterocyclic group which contains at least one heteroatom selected from O, N, and S, wherein the heterocyclylene group may be fused to another aromatic ring and may be substituted by one or more substituents R', wherein R' is as defined above;
wherein a phosphonooxy group is —O—P(=O)(OH)$_2$ or a salt thereof;
wherein a phosphonooxyalkyl group denotes an -alkyl-O—P(=O)(OH)$_2$ group or a salt thereof, alkyl being as defined above.

4. The compound of claim 1, wherein R$^1$ is

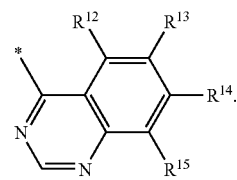

5. The compound according to claim 1, wherein X represents S; Y represents NH; A represents ←—NHCO—, where ←indicates the point of attachment to R$^3$; R$^5$ represents H.

6. The compound according to claim 4, wherein R$^3$ is an optionally substituted aryl group.

7. The compound according to claim 5, wherein R$^3$ is an optionally substituted aryl group.

8. The compound according to claim 1, wherein R$^3$ is an optionally substituted phenyl group.

9. The compound according to claim 1 wherein

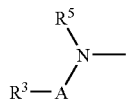

is attached to the 5-position of the benzazole.

10. The compound according to claim 2 wherein

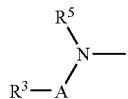

is attached to the 5-position of the benzazole.

11. The compound according to claim 3 wherein

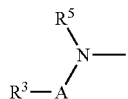

A is attached to the 5-position of the benzazole.

12. The compound according to claim 1 wherein

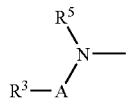

is attached to the 6-position of the benzazole.

13. The compound according to claim 2 wherein

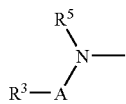

is attached to the 6-position of the benzazole.

14. The compound according to claim 3 wherein

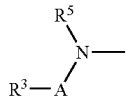

is attached to the 6-position of the benzazole.

15. A composition containing a compound according to claim 1 and a pharmaceutically acceptable carrier or diluent.

16. A composition containing a compound according to claim 2 and a pharmaceutically acceptable carrier or diluent.

17. A composition containing a compound according to claim 3 and a pharmaceutically acceptable carrier or diluent.

* * * * *